(12) United States Patent
Wan et al.

(10) Patent No.: US 7,713,958 B2
(45) Date of Patent: May 11, 2010

US007713958B2

(54) COMPOUNDS AND COMPOSITIONS AS PROTEIN KINASE INHIBITORS

(75) Inventors: Yongqin Wan, Irvine, CA (US); Nathanael S. Gray, Boston, MA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 12/187,289

(22) Filed: Aug. 6, 2008

(65) Prior Publication Data

US 2009/0137555 A1 May 28, 2009

Related U.S. Application Data

(63) Continuation of application No. 10/836,030, filed on Apr. 30, 2004, now Pat. No. 7,423,031.

(60) Provisional application No. 60/467,738, filed on May 1, 2003.

(51) Int. Cl.
*C07D 487/04* (2006.01)
*C07D 223/00* (2006.01)
*C07D 209/00* (2006.01)
*A61K 31/55* (2006.01)

(52) U.S. Cl. .................................. 514/212.06; 540/521
(58) Field of Classification Search ................. 540/521; 514/212.06

See application file for complete search history.

*Primary Examiner*—Bruck Kifle
(74) *Attorney, Agent, or Firm*—Scott W. Reid; Genomics Institute of the Novartis Research Foundation

(57) ABSTRACT

The invention provides a novel class of compounds, pharmaceutical compositions comprising such compounds and methods of using such compounds to treat or prevent diseases and disorders associated with kinase activity, particularly diseases associated with the activity of CDK1, CDK2, CDK4, CDK5, GSK3β, Bcr-abl, Flt-3, c-Kit, PDGFRβ, Src, Mek1 and CK1.

10 Claims, No Drawings

COMPOUNDS AND COMPOSITIONS AS PROTEIN KINASE INHIBITORS

CROSS-REFERENCE TO RELATED APPLICATIONS

The present application claims the benefit of priority to U.S. Nonprovisional application Ser. No. 10/836,030, filed Apr. 30, 2004 and U.S. Provisional Patent Application No. 60/467,738, filed May 1, 2003. The full disclosure of this application is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases and disorders associated with kinase activity, particularly diseases associated with the activity of CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met kinases.

2. Background

Kinases are involved in many aspects of cellular metabolism, proliferation, differentiation and development. A partial, non-limiting list of kinases include CDK1, CD 2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met kinases. Many diseases are associated with abnormal cellular responses triggered by protein kinase-mediated events. Disease areas include autoimmune diseases, inflammatory diseases, neurological and neurodegenerative diseases, cancer, cardiovascular diseases, allergies and hormone-related diseases. In particular, kinases have been implicated in various diseases including: diabetes; Alzheimer's disease and mood disorders such as bipolar disorder; CNS disorders such as manic-depressive disorder and neurodegenerative diseases; cardiomyocyte hypertrophy; and development and regulation of sperm motility. Further, kinases been implicated in hair loss, schizophrenia and neurotrauma, for example, stroke, traumatic brain surgery and spinal cord trauma. These diseases may be caused by, or result in, the abnormal operation of certain cell signaling pathways, for example, those signaling pathways in which CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met kinases play a role. Accordingly, molecules that modulate the activity of kinase-mediated signaling are useful as therapeutic agents in the treatment of such diseases.

SUMMARY OF THE INVENTION

In one aspect, this invention provides compounds of Formula I:

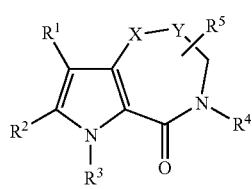

in which:

$R^1$ and $R^2$ are independently selected from hydrogen, halo, cyano, nitro, amino, phenyl, $C_{1-6}$alkyl, $C_{1-6}$alkoxy, halo-substituted-$C_{1-6}$alkyl and halo-substituted-$C_{1-6}$alkoxy; or $R^1$ and $R^2$ taken together with the carbon atoms to which $R^1$ and $R^2$ are attached form a phenyl ring optionally substituted by 1 to 3 substituents selected from halo, cyano, nitro, amino, methanesulfonyl, $C_{1-6}$alkyl, $C_{1-6}$alkoxy, halo-substituted-$C_{1-6}$alkyl and halo-substituted-$C_{1-6}$alkoxy;

$R^3$, $R^4$ and $R^5$ are independently selected from hydrogen, $C_{1-6}$alkyl, $C_{1-6}$alkoxy, halo-substituted-$C_{1-6}$alkyl and halo-substituted-$C_{1-6}$alkoxy; and —X—Y— is selected from —CHZ—CH$_2$—, —C(=Z)—CH$_2$— and —CZ=CH—; wherein =Z is selected from formula (a) and (b) and —Z is selected from formula (c), (d) and (e):

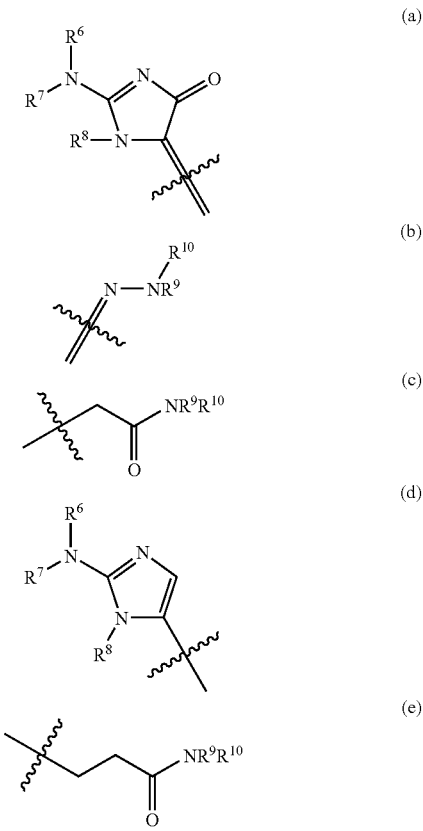

wherein $R^6$, $R^8$ and $R^9$ are independently selected from hydrogen, $C_{1-6}$alkyl, $C_{1-6}$alkoxy, halo-substituted-$C_{1-6}$alkyl and halo-substituted-$C_{1-6}$alkoxy;

$R^7$ is selected from hydrogen, $C_{1-6}$alkyl, $C_{1-6}$alkoxy, halo-substituted-$C_{1-6}$alkyl, halo-substituted-$C_{1-6}$alkoxy, —C(O)OR$^{11}$ and —C(O)R$^{11}$; wherein R$^{11}$ is hydrogen or $C_{1-6}$alkyl;

$R^{10}$ is selected from $C_{1-6}$alkyl, —NR$^{11}$R$^{12}$, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; wherein any alkyl is optionally substituted with —NR$^{11}$R$^{11}$, $C_{1-6}$alkoxy or hydroxy; and wherein any cycloalkyl, heterocycloalkyl, aryl or heteroaryl is optionally substituted by 1 to 3 substituents selected from halo, hydroxy, cyano, amino, nitro, —C(O)OR$^{11}$, —C(O)NR$^{11}$R$^{11}$, —SNR$^{11}$R$^{11}$, —S(O)NR$^{11}$R$^{11}$, —S(O)$_2$NR$^{11}$R$^{11}$, $C_{1-6}$alkyl, $C_{1-6}$alkoxy, halo-substituted- $C_{1-6}$alkyl and halo-substituted-$C_{1-6}$alkoxy; wherein $R^{11}$ is hydrogen or $C_{1-6}$alkyl; $R^{12}$ is $C_{3-12}$cycloalkyl optionally substituted with amino; or $R^9$ and $R^{10}$ together with the nitrogen to which $R^9$ and $R^{10}$ are attached form $C_{3-10}$heterocycloalkyl; and the N-oxide derivatives, prodrug derivatives, protected derivatives, individual isomers and mixtures of isomers thereof; and the pharmaceutically acceptable salts and solvates (e.g. hydrates) of such compounds.

In a second aspect, this invention provides a pharmaceutical composition which contains a compound of Formula I or an N-oxide derivative, individual isomer or mixture of isomers thereof, or a pharmaceutically acceptable salt thereof, in admixture with one or more suitable excipients.

In a third aspect, this invention provides a method for treating a disease in an animal in which inhibition of CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and/or c-Met kinases activity can prevent, inhibit or ameliorate the pathology and/or symptomology of the disease, which method comprises administering to the animal a therapeutically effective amount of a compound of Formula I or a N-oxide derivative, individual isomer or mixture of isomers thereof; or a pharmaceutically acceptable salt thereof.

In a fourth aspect, this invention provides the use of a compound of Formula I in the manufacture of a medicament for treating a disease in an animal in which CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and/or c-Met kinases activity contributes to the pathology and/or symptomology of the disease.

In a fifth aspect, this invention provides a process for preparing compounds of Formula I and the N-oxide derivatives, prodrug derivatives, protected derivatives, individual isomers and mixtures of isomers thereof; and the pharmaceutically acceptable salts thereof.

DESCRIPTION OF THE PREFERRED EMBODIMENTS

The invention provides compounds that are useful in the treatment and/or prevention of diseases or disorders mediated by kinase activity. Also provided are methods for treating such diseases or disorders.

Definitions

In this specification, unless otherwise defined:

"Alkyl" as a group and as a structural element of other groups, for example halo-substituted-alkyl, alkoxy, acyl, alkylthio, alkylsulfonyl and alkylsulfinyl, can be either straight-chained or branched. "Alkenyl" as a group and as a structural element of other groups contains one or more carbon-carbon double bonds, and can be either straight-chain, or branched. Any double bonds can be in the cis- or trans-configuration. A preferred alkenyl group is vinyl. "Alkynyl" as a group and as structural element of other groups and compounds contains at least one C≡C triple bond and can also contain one or more C═C double bonds, and can, so far as possible, be either straight-chain or branched. A preferred alkynyl group is propargyl. Any cycloalkyl group, alone or as a structural element of other groups can contain from 3 to 8 carbon atoms, preferably from 3 to 6 carbon atoms.

"Aryl" means a monocyclic or fused bicyclic aromatic ring assembly containing six to ten ring carbon atoms. For example, aryl can be phenyl or naphthyl, preferably phenyl.

"Arylene" means a divalent radical derived from an aryl group. For example, arylene as used in this application can be phenylene or naphthylene.

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl.

"Heteroaryl" means aryl, as defined in this application, provided that one or more of the ring carbon atoms indicated are replaced by a hetero atom moiety selected from N, O or S, and each ring is comprised of 5 to 6 ring atoms, unless otherwise stated. For example, heteroaryl as used in this application includes thiazolyl, thiophenyl, quinolinyl, pyrimidinyl, pyrazolyl, pyridinyl, furanyl, isoxazolyl, benzoxazolyl or benzo[1,3]dioxolyl, preferably pyrimidinyl, quinolinyl or pyridinyl. "Heteroarylene" means heteroaryl, as defined in this application, provided that the ring assembly comprises a divalent radical.

DETAILED DESCRIPTION OF THE INVENTION

The invention provides compounds that are useful for treating or preventing diseases or disorders that are mediated by kinase activity.

In some embodiments compounds of the invention are of Formula Ia:

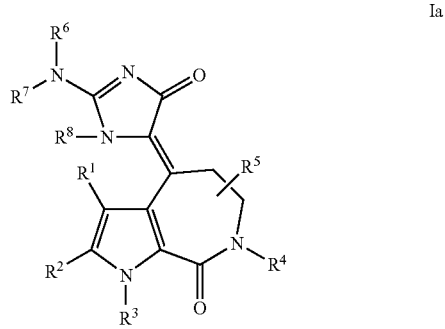

Ia in which $R^1$ and $R^2$ are independently selected from hydrogen and halo; or $R^1$ and $R^2$ taken together with the carbon atoms to which $R^1$ and $R^2$ are attached form a phenyl ring optionally substituted by 1 to 3 substituents selected from halo, methanesulfonyl, nitro and amino; $R^3$, $R^4$, $R^5$, $R^6$, $R^8$ and $R^9$ are independently selected from hydrogen and $C_{1-6}$alkyl; and $R^7$ is selected from hydrogen, $C_{1-6}$alkyl and —C(O)$R^{11}$; wherein $R^{11}$ is hydrogen or $C_{1-6}$alkyl.

In a further embodiment, in relation to compounds of formula Ia, $R^1$ and $R^2$ are independently selected from hydrogen and halo; $R^3$, $R^4$, $R^5$, $R^6$, $R^8$ and $R^9$ are hydrogen; and $R^7$ is selected from hydrogen, ethyl and —C(O)CH$_3$.

Preferred compounds of formula Ia are: 4-(2-amino-5-oxo-3,5-dihydro-imidazol-4-ylidene)-2,3-dichloro-4,5,6,7-tetrahydro-1H-pyrrolo[2,3-c]azepin-8-one; N-[5-(2,3-dibromo-8-oxo-5,6,7,8-tetrahydro-1H-pyrrolo[2,3-c]azepin-4-ylidene)-4-oxo-4,5-dihydro-1H-imidazol-2-yl]-acetamide; 2,3-dibromo-4-(2-ethylamino-5-oxo-3,5-dihydro-imidazol-4-ylidene)-4,5,6,7-tetrahydro-1H-pyrrolo [2,3-c]azepin-8-one; and 4-(2-amino-5-oxo-3,5-dihydro-imidazol-4-ylidene)-2,3-dibromo-6-methyl-4,5,6,7-tetrahydro-1H-pyrrolo[2,3-c]azepin-8-one;

In another embodiment, in relation to compounds of formula Ia, $R^1$ and $R^2$ taken together with the carbon atoms to which $R^1$ and $R^2$ are attached form a phenyl ring optionally substituted by 1 to 3 substituents selected from halo, methanesulfonyl, nitro and amino; $R^3$, $R^4$, $R^6$, $R^8$ and $R^9$ are hydrogen; $R^5$ is $C_{1-6}$alkyl; and $R^7$ is selected from hydrogen and —C(O)$R^{11}$; wherein $R^{11}$ is $C_{1-6}$alkyl. Preferably, $R^5$ is methyl and $R^7$ is hydrogen or —C(O)CH$_3$.

Further preferred compounds of formula Ia are: 5-(2-amino-5-oxo-3,5-dihydro-imidazol-4-ylidene)-3,4,5,10-tetrahydro-2H-azepino[3,4-b]indol-1-one; 5-(2-amino-5-oxo-3,5-dihydro-imidazol-4-ylidene)-7-bromo-3,4,5,10-tetrahydro-2H-azepino[3,4-b]indol-1-one; 5-(2-amino-5-oxo-3,5-dihydro-imidazol-4-ylidene)-7-chloro-3,4,5,10-tetrahydro-2H-azepino[3,4-b]indol-1-one; 5-(2-amino-5-oxo-3,5-dihydro-imidazol-4-ylidene)-7-fluoro-3,4,5,10-tetrahydro-2H-azepino[3,4-b]indol-1-one; 5-(2-amino-5-oxo-3,5-dihydro-imidazol-4-ylidene)-9-nitro-3,4,5,10-tetrahydro-2H-azepino[3,4-b]indol-1-one; 5-(2-amino-5-oxo-3,5-dihydro-imidazol-4-ylidene)-7-nitro-3,4,5,10-tetrahydro-2H-azepino[3,4-b]indol-1-one; 7-amino-5-(2-amino-5-oxo-3,5-dihydro-imidazol-4-ylidene)-3,4,5,10-tetrahydro-2H-azepino[3,4-b]indol-1-one; 5-(2-Amino-5-oxo-3,5-dihydro-imidazol-4-ylidene)-7-methanesulfonyl-3,4,5,10-tetrahydro-2H-azepino[3,4-b]indol-1-one; 9-amino-5-(2-amino-5-oxo-3,5-dihydro-imidazol-4-ylidene)-3,4,5,10-tetrahydro-2H-azepino[3,4-b]indol-1-one; N-[5-(7-bromo-1-oxo-1,3,4,10-tetrahydro-2H-azepino[3,4-b]indol-5-ylidene)-4-oxo-4,5-dihydro-1H-imidazol-2-yl]-acetamide; and 5-(2-amino-5-oxo-3,5-dihydro-imidazol-4-ylidene)-7-bromo-3-methyl-3,4,5,10-tetrahydro-2H-azepino[3,4-b]indol-1-one.

In another embodiment, compounds of the invention are of Formula Ib:

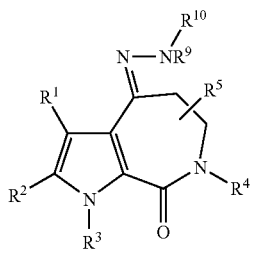

Ib in which $R^1$ and $R^2$ are independently selected from hydrogen, halo and phenyl; or $R^1$ and $R^2$ taken together with the carbon atoms to which $R^1$ and $R^2$ are attached form a phenyl ring optionally substituted by 1 to 3 substituents selected from halo and amino; $R^3$, $R^4$ and $R^5$ are independently selected from hydrogen and $C_{1-6}$alkyl; $R^9$ is hydrogen; and $R^{10}$ is selected from $C_{1-6}$alkyl, $C_{6-10}$aryl-$C_{0-4}$alkyl and $C_{5-10}$heteroaryl-$C_{0-4}$alkyl; wherein any aryl or heteroaryl is optionally substituted by 1 to 3 substituents selected from halo, nitro, —C(O)OH, —S(O)$_2$NH$_2$, $C_{1-6}$alkoxy and halo-substituted-$C_{1-6}$alkyl.

In a further embodiment, $R^1$ and $R^2$ are independently selected from halo and phenyl; $R^3$ and $R^4$ are hydrogen and $R^5$ is methyl; $R^9$ is hydrogen; $R^{10}$ is selected from $C_{6-10}$aryl-$C_{0-4}$alkyl and $C_{5-10}$heteroaryl-$C_{0-4}$alkyl; wherein any aryl or heteroaryl is optionally substituted by halo, nitro, —C(O)OH and halo-substituted-$C_{1-6}$alkyl.

Preferred compounds of formula Ib are: 2-[N'-(2,3-dibromo-8-oxo-5,6,7,8-tetrahydro-1H-pyrrolo[2,3-c]azepin-4-ylidene)-hydrazino]-benzoic acid; 4-[N'-(2,3-dibromo-8-oxo-5,6,7,8-tetrahydro-1H-pyrrolo[2,3-c]azepin-4-ylidene)-hydrazino]-benzoic acid; 2,3-dibromo-4-(pyridin-2-yl-hydrazono)-4,5,6,7-tetrahydro-1H-pyrrolo[2,3-c]azepin-8-one; 2,3-dibromo-4-[(4-nitro-phenyl)-hydrazono]-4,5,6,7-tetrahydro-1H-pyrrolo[2,3-c]azepin-8-one; 4-[N'-(2,3-dibromo-8-oxo-5,6,7,8-tetrahydro-1H-pyrrolo[2,3-c]azepin-4-ylidene)-hydrazino]-benzenesulfonamide; 2,3-dibromo-4-[(7-chloro-quinolin-4-yl)-hydrazono]-4,5,6,7-tetrahydro-1H-pyrrolo[2,3-c]azepin-8-one; 2,3-dibromo-4-[(5-trifluoromethyl-pyrimidin-2-yl)-hydrazono]-4,5,6,7-tetrahydro-1H-pyrrolo[2,3-c]azepin-8-one; 2,3-dibromo-4-(pyridin-3-yl-hydrazono)-4,5,6,7-tetrahydro-1H-pyrrolo[2,3-c]azepin-8-one; 2,3-dibromo-4-(pyridin-4-yl-hydrazono)-4,5,6,7-tetrahydro-1H-pyrrolo[2,3-c]azepin-8-one; 2-phenyl-4-(pyridin-2-yl-hydrazono)-4,5,6,7-tetrahydro-1H-pyrrolo[2,3-c]azepin-8-one; 6-methyl-4-(pyridin-2-yl-hydrazono)-4,5,6,7-tetrahydro-1H-pyrrolo[2,3-c]azepin-8-one; and 2,3-dichloro-4-(pyridin-2-yl-hydrazono)-4,5,6,7-tetrahydro-1H-pyrrolo[2,3-c]azepin-8-one.

In yet a further embodiment, $R^1$ and $R^2$ taken together with the carbon atoms to which $R^1$ and $R^2$ are attached form a phenyl ring optionally substituted by 1 to 3 substituents selected from halo and amino; $R^3$, $R^4$ and $R^5$ are independently selected from hydrogen and $C_{1-6}$alkyl; $R^9$ is hydrogen; and $R^{10}$ is selected from $C_{6-10}$aryl-$C_{0-4}$alkyl and $C_{5-10}$heteroaryl-$C_{0-4}$alkyl; wherein any aryl or heteroaryl is optionally substituted by 1 to 3 substituents selected from halo, nitro, —C(O)OH, —S(O)$_2$NH$_2$, $C_{1-6}$alkoxy and halo-substituted-$C_{1-6}$alkyl.

Further preferred compounds of formula Ib are: 5-(pyridin-2-yl-hydrazono)-3,4,5,10-tetrahydro-2H-azepino[3,4-b]indol-1-one; 7-chloro-5-(pyridin-2-yl-hydrazono)-3,4,5,10-tetrahydro-2H-azepino[3,4-b]indol-1-one; 7-bromo-5-(pyridin-2-yl-hydrazono)-3,4,5,10-tetrahydro-2H-azepino[3,4-b]indol-1-one; 9-amino-5-(pyridin-2-yl-hydrazono)-3,4,5,10-tetrahydro-2H-azepino[3,4-b]indol-1-one; 4-[N'-(7-chloro-1-oxo-1,3,4,10-tetrahydro-2H-azepino[3,4-b]indol-5-ylidene)-hydrazino]-benzenesulfonamide; 7-chloro-5-(pyridin-4-yl-hydrazono)-3,4,5,10-tetrahydro-2H-azepino[3,4-b]indol-1-one; 7-chloro-5-(pyridin-3-yl-hydrazono)-3,4,5,10-tetrahydro-2H-azepino[3,4-b]indol-1-one; 7-fluoro-5-(pyridin-2-yl-hydrazono)-3,4,5,10-tetrahydro-2H-azepino[3,4-b]indol-1-one; 7-bromo-3-methyl-5-(pyridin-2-yl-hydrazono)-3,4,5,10-tetrahydro-2H-azepino[3,4-b]indol-1-one; 4-[N'-(7-fluoro-1-oxo-1,3,4,10-tetrahydro-2H-azepino[3,4-b]indol-5-ylidene)-hydrazino]-benzenesulfonamide; 7-fluoro-5-(pyridin-3-yl-hydrazono)-3,4,5,10-tetrahydro-2H-azepino[3,4-b]indol-1-one; 7-fluoro-5-[(6-methoxy-pyridin-3-yl)-hydrazono]-3,4,5,10-tetrahydro-2H-azepino[3,4-b]indol-1-one; 7-chloro-5-[(6-methoxy-pyridin-3-yl)-hydrazono]-3,4,5,10-tetrahydro-2H-azepino[3,4-b]indol-1-one; 5-[(2-chloro-pyridin-3-yl)-hydrazono]-7-fluoro-3,4,5,10-tetrahydro-2H-azepino[3,4-b]indol-1-one; 7-chloro-5-[(2-chloro-pyridin-3-yl)-hydrazono]-3,4,5,10-tetrahydro-2H-azepino[3,4-b]indol-1-one; 7-chloro-5-[(5-chloro-pyridin-2-yl)-hydrazono]-3,4,5,10-tetrahydro-2H-azepino[3,4-b]indol-1-one; 5-[(5-chloro-pyridin-2-yl)-hydrazono]-7-fluoro-3,4,5,10-tetrahydro-2H-azepino[3,4-b]indol-1-one; 6-[N'-(7-chloro-1-oxo-1,3,4,10-tetrahydro-2H-azepino[3,4-b]indol-5-ylidene)-hydrazino]-pyridine-3-sulfonic acid amide; 6-[N'-(7-fluoro-1-oxo-1,3,4,10-tetrahydro-2H-azepino[3,4-b]indol-5-ylidene)-hydrazino]-pyridine-3-sulfonic acid amide; 7-fluoro-5-[(5-trifluoromethyl-pyridin-2-yl)-hydrazono]-3,4,5,10-tetrahydro-2H-azepino[3,4-b]indol-1-one; 7-chloro-5-[(5-trifluoromethyl-pyridin-2-yl)-hydrazono]-3,4,5,10-tetrahydro-2H-azepino[3,4-b]indol-1-one;

7-chloro-5-[(5-nitro-pyridin-2-yl)-hydrazono]-3,4,5,10-tetrahydro-2H-azepino[3,4-b]indol-1-one; and 7-chloro-5-[(6-chloro-pyridin-3-yl)-hydrazono]-3,4,5,10-tetrahydro-2H-azepino[3,4-b]indol-1-one.

In a further embodiment, compounds of the invention are selected from Formula Ic$_1$ and Ic$_2$:

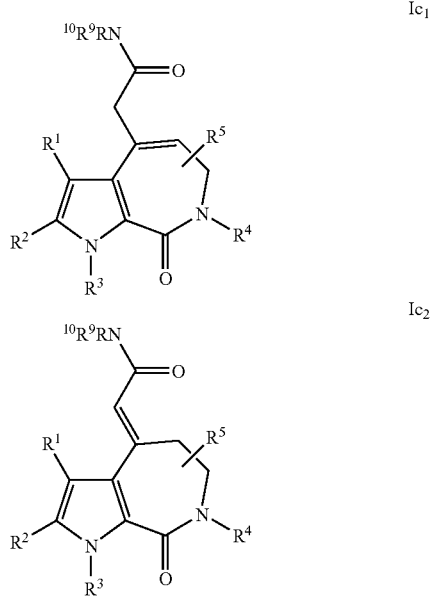

in which R$^1$ and R$^2$ taken together with the carbon atoms to which R$^1$ and R$^2$ are attached form a phenyl ring optionally substituted by 1 to 3 substituents selected from halo, cyano, nitro, amino, C$_{1-6}$alkyl, C$_{1-6}$alkoxy, halo-substituted-C$_{1-6}$alkyl and halo-substituted-C$_{1-6}$alkoxy; R$^3$, R$^4$ and R$^5$ are hydrogen; R$^9$ is selected from hydrogen and C$_{1-6}$alkyl; and R$^{10}$ is selected from C$_{1-6}$alkyl, —NR$^{11}$R$^{12}$, C$_{6-10}$aryl-C$_{0-4}$alkyl and C$_{5-10}$heteroaryl-C$_{0-4}$alkyl; wherein any alkyl is optionally substituted with —NR$^{11}$R$^{11}$, C$_{1-6}$alkoxy or hydroxy; and wherein any aryl or heteroaryl is optionally substituted by 1 to 3 substituents selected from halo, —C(O)NR$^{11}$R$^{11}$ and —S(O)$_2$NR$^{11}$R$^{11}$; wherein R$^{11}$ is hydrogen or C$_{1-6}$alkyl; R$^{12}$ is C$_{3-12}$cycloalkyl optionally substituted with amino; or R$^9$ and R$^{10}$ together with the nitrogen to which R$^9$ and R$^{10}$ are attached form C$_{3-10}$heterocycloalkyl.

In a further embodiment, R$^1$ and R$^2$ taken together with the carbon atoms to which R$^1$ and R$^2$ are attached form a phenyl ring optionally substituted by 1 to 3 halo substituents; R$^9$ is hydrogen or methyl; and R$^{10}$ is selected from methyl, ethyl, propyl, pyridinyl, pyridinyl-methyl, 2-amino-ethyl, 2-hydroxyethyl, 2-amino-propyl, 2-dimethylamino-ethyl, 2-methoxy-ethyl; and wherein any heteroaryl is optionally substituted by 1 to 3 substituents selected from halo, —C(O)NH$_2$ and —S(O)$_2$NH$_2$; or R$^9$ and R$^{10}$ together with the nitrogen to which R$^9$ and R$^{10}$ are attached form morpholino or piperazinyl.

Preferred compounds of formula Ic are: 2-(1-oxo-1,2,3,10-tetrahydro-2H-azepino[3,4-b]indol-5-ylidene)-N-pyridin-3-yl-acetamide; 2-(1-oxo-1,2,3,10-tetrahydro-2H-azepino[3,4-b]indol-5-ylidene)-N-pyridin-4-yl-acetamide; 4-[2-(1-oxo-1,2,3,10-tetrahydro-2H-azepino[3,4-b]indol-5-ylidene)-acetylamino]-benzamide; 2-(1-oxo-1,2,3,10-tetrahydro-2H-azepino[3,4-b]indol-5-ylidene)-N-(4-sulfamoyl-phenyl)-acetamide; 2-(1-oxo-1,2,3,10-tetrahydro-2H-azepino[3,4-b]indol-5-ylidene)-N-(3-sulfamoyl-phenyl)-acetamide; 2-(1-oxo-1,2,3,10-tetrahydro-2H-azepino[3,4-b]indol-5-ylidene)-N-(2-sulfamoyl-phenyl)-acetamide; N-(2-amino-cyclohexyl)-2-(1-oxo-1,2,3,10-tetrahydro-2H-azepino[3,4-b]indol-5-ylidene)-acetamide; N-(4-amino-cyclohexyl)-2-(1-oxo-1,2,3,10-tetrahydro-2H-azepino[3,4-b]indol-5-ylidene)-acetamide; N-(4-hydroxy-cyclohexyl)-2-(1-oxo-1,3,4,10-tetrahydro-2H-azepino[3,4-b]indol-5-ylidene)-acetamide; 2-(1-oxo-1,2,3,10-tetrahydro-2H-azepino[3,4-b]indol-5-ylidene)-N-pyridin-4-ylmethyl-acetamide; N-(2-chloro-pyridin-3-yl)-2-(1-oxo-1,2,3,10-tetrahydro-2H-azepino[3,4-b]indol-5-ylidene)-acetamide; N-(6-chloro-pyridin-3-yl)-2-(1-oxo-1,3,4,10-tetrahydro-2H-azepino[3,4-b]indol-5-ylidene)-acetamide; N-(6-chloro-pyridin-3-yl)-2-(7-fluoro-1-oxo-1,2,3,10-tetrahydro-azepino[3,4-b]indol-5-yl)-acetamide; N-(2-chloro-pyridin-3-yl)-2-(7-fluoro-1-oxo-1,2,3,10-tetrahydro-azepino[3,4-b]indol-5-yl)-acetamide; 2-(7-fluoro-1-oxo-1,2,3,10-tetrahydro-azepino[3,4-b]indol-5-yl)-N-(3-sulfamoyl-phenyl)-acetamide; 2-(7-fluoro-1-oxo-1,2,3,10-tetrahydro-azepino[3,4-b]indol-5-yl)-N-pyridin-4-ylmethyl-acetamide; 2-(7-fluoro-1-oxo-1,2,3,10-tetrahydro-azepino[3,4-b]indol-5-yl)-N-pyridin-4-yl-acetamide; 2-(7-fluoro-1-oxo-1,2,3,10-tetrahydro-azepino[3,4-b]indol-5-yl)-N-propyl-acetamide; N-(2-amino-ethyl)-2-(7-fluoro-1-oxo-1,2,3,10-tetrahydro-azepino[3,4-b]indol-5-yl)-acetamide; 2-(7-fluoro-1-oxo-1,2,3,10-tetrahydro-azepino[3,4-b]indol-5-yl)-N-(2-hydroxy-ethyl)-acetamide; N-(3-amino-propyl)-2-(7-fluoro-1-oxo-1,2,3,10-tetrahydro-azepino[3,4-b]indol-5-yl)-acetamide; N-(2-dimethylamino-ethyl)-2-(7-fluoro-1-oxo-1,2,3,10-tetrahydro-azepino[3,4-b]indol-5-yl)-acetamide; 2-(7-fluoro-1-oxo-1,2,3,10-tetrahydro-azepino[3,4-b]indol-5-yl)-N-(2-methoxy-ethyl)-N-methyl-acetamide; 7-fluoro-5-(2-morpholin-4-yl-2-oxo-ethyl)-3,10-dihydro-2H-azepino[3,4-b]indol-1-one; 2-(7-fluoro-1-oxo-1,2,3,10-tetrahydro-azepino[3,4-b]indol-5-yl)-N-(2-sulfamoyl-phenyl)-acetamide; 7-fluoro-5-(2-oxo-2-piperazin-1-yl-ethyl)-3,10-dihydro-2H-azepino[3,4-b]indol-1-one; 2-(7-fluoro-1-oxo-1,2,3,10-tetrahydro-azepino[3,4-b]indol-5-yl)-N-(4-sulfamoyl-phenyl)-acetamide; 2-(7-fluoro-1-oxo-1,2,3,10-tetrahydro-azepino[3,4-b]indol-5-yl)-N-pyridin-2-yl-acetamide; 2-(7-fluoro-1-oxo-1,2,3,10-tetrahydro-azepino[3,4-b]indol-5-yl)-N-pyridin-3-yl-acetamide; 4-[2-(7-fluoro-1-oxo-1,2,3,10-tetrahydro-azepino[3,4-b]indol-5-yl)-acetylamino]-benzamide; N-(2-Amino-cyclohexyl)-2-(7-fluoro-1-oxo-1,2,3,10-tetrahydro-azepino[3,4-b]indol-5-yl)-acetamide; N-(2-Dimethylamino-ethyl)-2-(7-fluoro-1-oxo-1,3,4,10-tetrahydro-2H-azepino[3,4-b]indol-5-ylidene)-acetamide; 2-(7-Fluoro-1-oxo-1,3,4,10-tetrahydro-2H-azepino[3,4-b]indol-5-ylidene)-N-(3-hydroxy-propyl)-acetamide; 2-(7-Fluoro-1-oxo-1,3,4,10-tetrahydro-2H-azepino[3,4-b]indol-5-ylidene)-N-(2-hydroxy-ethyl)-acetamide; N-(2-Amino-ethyl)-2-(7-fluoro-1-oxo-1,3,4,10-tetrahydro-2H-azepino[3,4-b]indol-5-ylidene)-acetamide; 2-(7-Fluoro-1-oxo-1,3,4,10-tetrahydro-2H-azepino[3,4-b]indol-5-ylidene)-N-(2-pyridin-3-yl-ethyl)-acetamide; 2-(7-Fluoro-1-oxo-1,3,4,10-tetrahydro-2H-azepino[3,4-b]indol-5-ylidene)-N-(2-pyridin-2-yl-ethyl)-acetamide; N-(4-Amino-cyclohexyl)-2-(7-fluoro-1-oxo-1,3,4,10-tetrahydro-2H-azepino[3,4-b]indol-5-ylidene)-acetamide; N-(2-Amino-cyclohexyl)-2-(7-fluoro-1-oxo-1,3,4,10-tetrahydro-2H-azepino[3,4-b]indol-5-ylidene)-acetamide; and 7-Fluoro-5-(2-oxo-2-piperazin-1-yl-ethylidene)-3,4,5,10-tetrahydro-2H-azepino[3,4-b]indol-1-one.

In a further embodiment, compounds of the invention are of Formula Id:

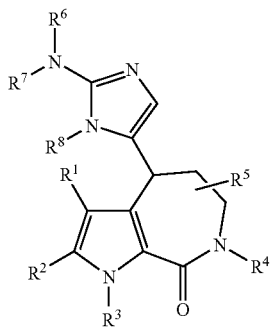

in which $R^1$ and $R^2$ are independently halo; or $R^1$ and $R^2$ taken together with the carbon atoms to which $R^1$ and $R^2$ are attached form a phenyl ring optionally substituted by 1 to 3 substituents selected from halo and nitro; $R^3$, $R^4$, $R^5$, $R^6$ and $R^8$ are hydrogen; and $R^7$ is hydrogen or $C_{1-6}$alkyl.

Preferred compounds of formula Id are: 2,3-dibromo-4-(2-ethylamino-3H-imidazol-4-yl)-4,5,6,7-tetrahydro-1H-pyrrolo[2,3-c]azepin-8-one; 5-(2-amino-3H-imidazol-4-yl)-7-bromo-3,4,5,10-tetrahydro-2H-azepino[3,4-b]indol-1-one; 5-(2-amino-3H-imidazol-4-yl)-7-chloro-3,4,5,10-tetrahydro-2H-azepino[3,4-b]indol-1-one; and 5-(2-amino-3H-imidazol-4-yl)-9-nitro-3,4,5,10-tetrahydro-2H-azepino[3,4-b]indol-1-one.

In a further embodiment, compounds of the invention are of Formula Ie:

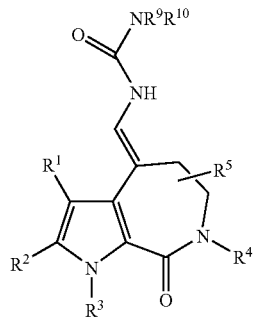

in which $R^1$ and $R^2$ taken together with the carbon atoms to which $R^1$ and $R^2$ are attached form a phenyl ring optionally substituted by 1 to 3 substituents selected from halo, cyano, nitro, amino, $C_{1-6}$alkyl, $C_{1-6}$alkoxy, halo-substituted-$C_{1-6}$alkyl and halo-substituted-$C_{1-6}$alkoxy; $R^3$, $R^4$ and $R^5$ are hydrogen; $R^9$ is selected from hydrogen and $C_{1-6}$alkyl; and $R^{10}$ is selected from $C_{1-6}$alkyl, $C_{6-10}$aryl-$C_{0-4}$alkyl and $C_{5-10}$heteroaryl-$C_{0-4}$alkyl; wherein any alkyl is optionally substituted with —$NR^{11}R^{11}$, $C_{1-6}$alkoxy or hydroxy; and wherein any aryl or heteroaryl is optionally substituted by 1 to 3 substituents selected from halo, —C(O)$NR^{11}R^{11}$ and —S(O)$_2NR^{11}R^{11}$; wherein $R^{11}$ is hydrogen or $C_{1-6}$alkyl; or $R^9$ and $R^{10}$ together with the nitrogen to which $R^9$ and $R^{10}$ are attached form $C_{3-10}$heterocycloalkyl.

In a further embodiment, $R^1$ and $R^2$ taken together with the carbon atoms to which $R^1$ and $R^2$ are attached form a phenyl ring optionally substituted by 1 to 3 halo substituents; $R^9$ is hydrogen or methyl; and $R^{10}$ is selected from methyl, ethyl, propyl, pyridinyl, pyridinyl-methyl, 2-amino-ethyl, 2-hydroxyethyl, 2-amino-propyl, 2-dimethylamino-ethyl, 2-methoxy-ethyl; and wherein any heteroaryl is optionally substituted by 1 to 3 substituents selected from halo, —C(O)$NH_2$ and —S(O)$_2NH_2$; or $R^9$ and $R^{10}$ together with the nitrogen to which $R^9$ and $R^{10}$ are attached form morpholino or piperazinyl.

Preferred compounds of formula Ie are: 1-(7-Fluoro-1-oxo-1,3,4,10-tetrahydro-2H-azepino[3,4-b]indol-5-ylidenemethyl)-3-pyridin-3-yl-urea; 4-[3-(7-Fluoro-1-oxo-1,3,4,10-tetrahydro-2H-azepino[3,4-b]indol-5-ylidenemethyl)-ureido]-benzenesulfonamide; 3-[3-(7-Fluoro-1-oxo-1,3,4,10-tetrahydro-2H-azepino[3,4-b]indol-5-ylidenemethyl)-ureido]-benzenesulfonamide; 1-(7-Fluoro-1-oxo-1,3,4,10-tetrahydro-2H-azepino[3,4-b]indol-5-ylidenemethyl)-3-propyl-urea; 1-(7-Fluoro-1-oxo-1,3,4,10-tetrahydro-2H-azepino[3,4-b]indol-5-ylidenemethyl)-3-pyridin-4-yl-urea; 1-(2-Chloro-pyridin-4-yl)-3-(7-fluoro-1-oxo-1,3,4,10-tetrahydro-2H-azepino[3,4-b]indol-5-ylidenemethyl)-urea; 1-(7-Fluoro-1-oxo-1,3,4,10-tetrahydro-2H-azepino[3,4-b]indol-5-ylidenemethyl)-3-pyridin-2-yl-urea; 1-(7-Fluoro-1-oxo-1,3,4,10-tetrahydro-2H-azepino[3,4-b]indol-5-ylidenemethyl)-3-isoxazol-3-yl-urea; 1-(7-Fluoro-1-oxo-1,3,4,10-tetrahydro-2H-azepino[3,4-b]indol-5-ylidenemethyl)-3-thiazol-2-yl-urea; 1-(4-Amino-cyclohexyl)-3-(7-fluoro-1-oxo-1,3,4,10-tetrahydro-2H-azepino[3,4-b]indol-5-ylidenemethyl)-urea; 1-(7-Fluoro-1-oxo-1,3,4,10-tetrahydro-2H-azepino[3,4-b]indol-5-ylidenemethyl)-3-(3-hydroxy-propyl)-urea; 1-(2-Dimethylamino-ethyl)-3-(7-fluoro-1-oxo-1,3,4,10-tetrahydro-2H-azepino[3,4-b]indol-5-ylidenemethyl)-urea; 1-(7-Fluoro-1-oxo-1,3,4,10-tetrahydro-2H-azepino[3,4-b]indol-5-ylidenemethyl)-3-(2-hydroxy-ethyl)-urea; 1-(2-Amino-ethyl)-3-(7-fluoro-1-oxo-1,3,4,10-tetrahydro-2H-azepino[3,4-b]indol-5-ylidenemethyl)-urea; 1-(7-Fluoro-1-oxo-1,3,4,10-tetrahydro-2H-azepino[3,4-b]indol-5-ylidenemethyl)-3-pyridin-4-ylmethyl-urea; 1-(7-Fluoro-1-oxo-1,3,4,10-tetrahydro-2H-azepino[3,4-b]indol-5-ylidenemethyl)-3-(2-pyridin-3-yl-ethyl)-urea; 1-(7-Fluoro-1-oxo-1,3,4,10-tetrahydro-2H-azepino[3,4-b]indol-5-ylidenemethyl)-3-(2-pyridin-2-yl-ethyl)-urea; and 1-(2-Amino-cyclohexyl)-3-(7-fluoro-1-oxo-1,3,4,10-tetrahydro-2H-azepino[3,4-b]indol-5-ylidenemethyl)-urea.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes. The present invention also includes both the enzymatically phosphorylated or dephosphorylated compounds of Formula I, optionally in equilibrium.

Compounds of Formula I can exist in free form or in salt form, e.g. addition salts with inorganic or organic acids, e.g. an ammonium salt or salts with metals such as lithium, sodium, potassium, calcium, zinc or magnesium, or a mixture thereof. Compounds of Formula I and their salts in hydrate or solvate form are also part of the invention.

When the compounds of Formula I have asymmetric centers in the molecule, various optical isomers are obtained. The present invention also encompasses enantiomers, racemates, diastereoisomers and mixtures thereof. Moreover, when the compounds of Formula I include geometric isomers, the present invention embraces cis-compounds, trans-compounds and mixtures thereof. Similar considerations apply in relation to starting materials exhibiting asymmetric carbon atoms or unsaturated bonds as mentioned above.

Methods for Preparing Kinase Inhibitors

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula Ia and Id can be prepared by proceeding as in the following Reaction scheme 1:

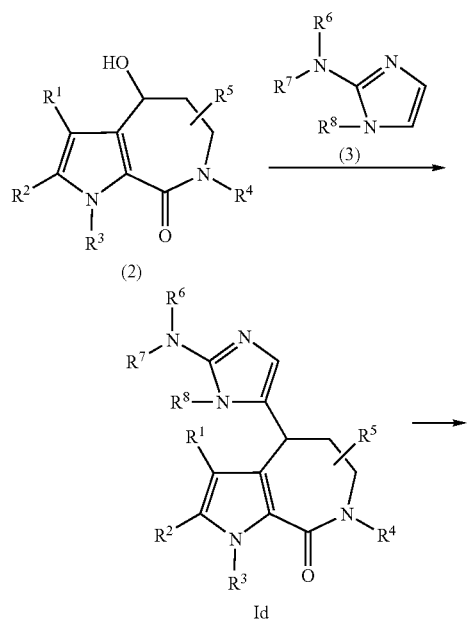

in which $R^1$, $R^2$, $R^3$, $R^5$, $R^6$, $R^7$ and $R^8$ are as defined for Formula I above.

Compounds of Formula Id can be prepared by reacting a compound of formula 2 with a compound of formula 3. The reaction can be effected in the presence of methanesulfonic acid at a temperature of 45 to 50° C. and requires 1 to 24 hours to complete. Compounds of Formula Ia can be prepared from compounds of Formula Id by reacting with $Br_2$ and NaOAc in acetic acid.

Compounds of Formula Ib can be prepared by proceeding as in the following Reaction scheme 2:

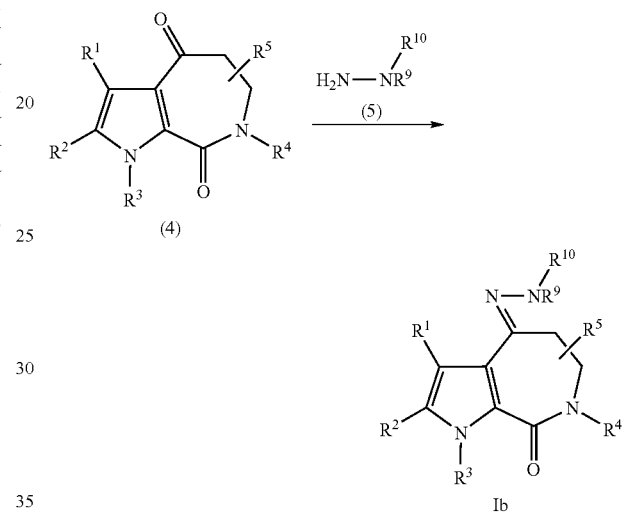

in which $R^1$, $R^2$, $R^3$, $R^5$, $R^9$ and $R^{10}$ are as defined for Formula I above.

Compounds of Formula Ib can be prepared by reacting a compound of formula 4 with a compound of formula 5. The reaction can be effected in the presence of a suitable acid (e.g. HCl, and the like), a suitable alcohol (e.g., ethanol, and the like) at a temperature of 80 to 90° C. and requires 1 to 5 hours to complete.

Compounds of Formula Ic can be prepared by proceeding as in the following Reaction scheme 3:

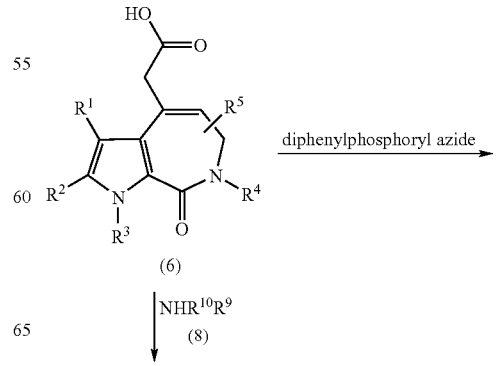

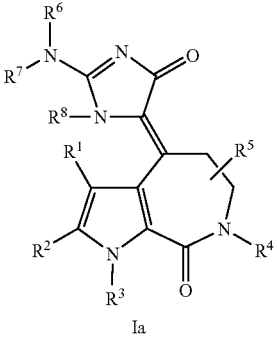

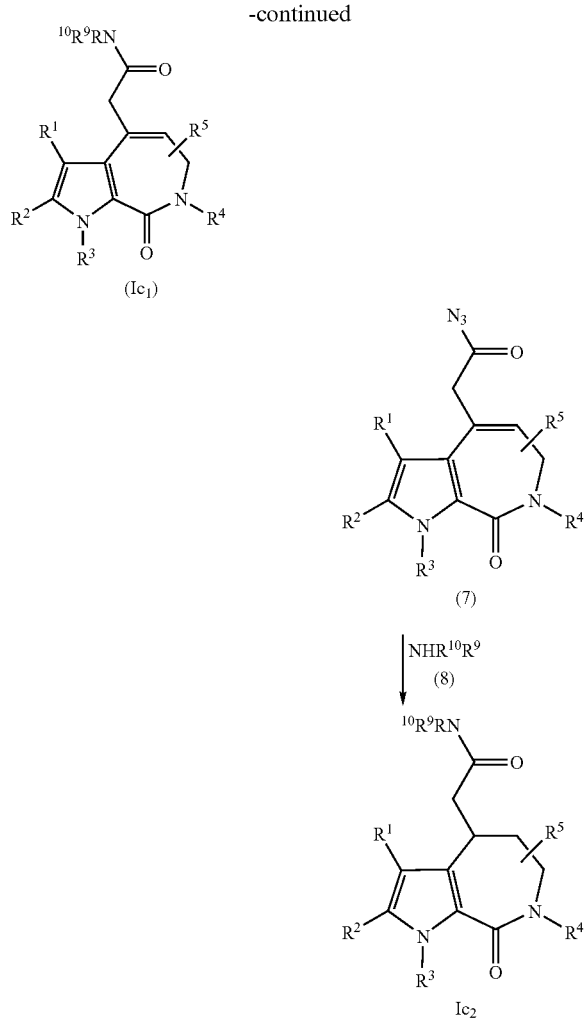

in which $R^1$, $R^2$, $R^3$, $R^5$, $R^9$ and $R^{10}$ are as defined for Formula I above.

Compounds of Formula $Ic_1$ can be prepared by reacting a compound of formula 6 with a compound of formula 8. The reaction can be effected in the presence of HATU, a suitable solvent (e.g., DMF, and the like) at a temperature of 15 to 20° C. and requires 0.5 to 2 hours to complete. A compound of formula 7 can be prepared by reacting a compound of formula 6 with diphenylphosphoryl azide. The reaction can be effected in the presence of triethylamine, a suitable solvent (e.g., DMF, and the like) at a temperature of 15 to 20° C. and requires 0.5 to 12 hours to complete. Compounds of Formula $Ic_2$ can be prepared by reacting a compound of formula 7 with a compound of formula 8. The reaction can be effected in a suitable solvent (e.g., toluene, and the like) at a temperature of 100 to 120° C. and requires 0.5 to 2 hours to complete.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamoylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) reacting a compound of formula 2 with formula 3; reacting a compound of formula 4 with formula 5, reacting a compound of formula 6 with formula 7; or converting a compound of formula Id to formula Ia; and for each of these:

(b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

Methods and Pharmaceutical Compositions for Treating CDK Related Conditions

The compounds of Formula I in free form or in pharmaceutically acceptable salt form, exhibit valuable pharmacological properties, for example, as indicated by the in vitro tests of Example 8 and are therefore indicated for therapy of diseases and disorders associated with altered CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met activity. A 10 µM concentration of a compound of Formula I preferable inhibits activity of one or more kinases selected from CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met by more than 70% (For examples, see Table 2). Further, compounds of Formula I preferably show an $IC_{50}$ against one or more of CDK5, CDK1 and GSK3β kinases in the range of $1 \times 10^{-9}$ to $1 \times 10^{-5}$ M, preferably less than 500 nM, more preferably less than 250 nM.

This invention also provides a method for preventing or treating diseases or conditions comprising abnormal cell growth in a mammal, including a human, comprising administering to the mammal a compound of Formula I in an amount effective to inhibit CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met kinase activity. Such diseases or conditions include, for example, cancer. The cancer may be a carcinoma, for example carcinoma of the bladder, breast, colon, kidney, liver, lung, for example small cell lung cancer, esophagus, gall bladder, ovary, pancreas, stomach, cervix, thyroid, prostate, or skin, for example squamous cell carcinoma; a hematopoietic tumor of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; a tumor of mesenchymal origin, for example fibrosarcoma or rhabdomyosarcoma; a tumor of the central or peripheral nervous system, for example astrocytoma, neuroblastomas, glioma or schwannoma; melanoma; seminoma; teratocarcinoma; osteosarcoma; xenoderoma pigmentosum; keratoctanthoma; thyroid follicular cancer; or Kaposi's sarcoma. Diseases or conditions comprising benign abnormal cell growth include benign prostate hyperplasia, familial adenomatosis polyposis, neuro-fibromatosis, atherosclerosis, pulmonary fibrosis, arthritis, psoriasis, glomerulonephritis, restenosis, hypertrophic scar formation, inflammatory bowel disease, transplantation rejection, fungal infection, and endotoxic shock.

This invention also provides a method for treating a neurodegenerative disease or condition in a mammal, including a human, comprising administering to the mammal a compound of formula 1 in an amount effective in treating said disease or condition. Such neurodegenerative diseases or conditions include, for example, Huntington's disease, stroke, spinal cord trauma, traumatic brain injury, multiinfarct dementia, epilepsy, amyotrophic lateral sclerosis, pain, viral induced dementia for example AIDS induced dementia, neurodegeneration associated with bacterial infection, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progressive supranuclear palsy, lower lateral sclerosis, and subacute sclerosing panencephalistis.

This invention also provides a method for treating a disease or condition the treatment of which can be effected or facilitated by altering dopamine mediated neurotransmission in a mammal, including a human, comprising administering to the mammal a compound of formula 1 in an amount effective in treating said disease or condition. Such diseases or conditions include, for example, Parkinson's disease; schizophrenia; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; drug addiction, including narcotic (e.g. heroin, opium, and morphine), cocaine and alcohol addiction; drug withdrawal, including narcotic, cocaine and alcohol withdrawal; obsessive compulsive disorder; Tourette's syndrome; depression; a major depressive episode, a manic or mixed mood episode, a hypomanic mood episode, a depressive episode with atypical features or with melancholic features or catatonic features, a mood episode with postpartum onset; post-stroke depression, major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example bipolar I disorder, bipolar II disorder, cyclothymic disorder; anxiety; attention deficit and hyperactivity disorder; and attention deficit disorder.

The required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of Formula I can be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of Formula I in free form or in pharmaceutically acceptable salt form in association with at least one pharmaceutical acceptable carrier or diluent can be manufactured in conventional manner by mixing with a pharmaceutically acceptable carrier or diluent.

The compounds of Formula I can be administered in free form or in pharmaceutically acceptable salt form, for example, as indicated above. Such salts can be prepared in a conventional manner and exhibit the same order of activity as the free compounds.

Also provided by the invention are compounds of Formula I, in free form or in a pharmaceutically acceptable salt form for use in treatment of conditions such as those described above. Pharmaceutical compositions, that includes a compound of Formula I in free form or pharmaceutically acceptable salt form, in association with a pharmaceutically acceptable diluent or carrier thereof are also provided by the invention.

Also provided by the invention are methods involving co-administration, e.g. concomitantly or in sequence, of a therapeutically effective non-toxic amount of a compound of Formula I and at least a second drug substance. For example, the compounds of Formula I can be administered as the sole active ingredient or in conjunction with, e.g. as an adjuvant to, other drugs e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator.

Where the compounds of Formula I are administered in conjunction with other therapies, dosages of the co-administered compounds will of course vary depending on the type of co-drug employed, on the specific drug employed, on the condition being treated and so forth.

Also provided by the invention are pharmaceutical combinations, e.g. a kit, comprising a) a first agent which is a compound of Formula I as disclosed herein, in free form or in pharmaceutically acceptable salt form, and b) at least one co-agent, e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

EXAMPLES

The present invention is further exemplified, but not limited by, the following examples that illustrate the preparation of compounds of formula I (examples), and their intermediates (References), according to the invention.

Reference 1

2,3-Dibromo-4-hydroxy-4,5,6,7-tetrahydro-1H-pyrrolo[2,3-c]azepin-8-one

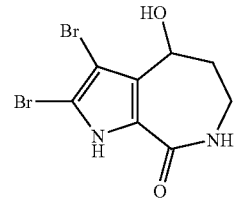

To a solution of 3-[(4,5-dibromo-1H-pyrrole-2-carbonyl)-amino]-propionic acid ethyl ester (7.80 g, 21.1 mmol) in 160 mL of 1:1 mixture of dioxane-$H_2O$ is added KOH (4.72 g, 84.2 mmol). The mixture is stirred at room temperature overnight. The solution is extracted with $Et_2O$ (100 mL) and the aqueous layer is then acidified with HCl to a pH of less than 2 followed by extraction with EtOAc (80 mL×3). The EtOAc layers are combined, washed with brine, and dried with $Na_2SO_4$. After removal of solvent, 3-[(4,5-dibromo-1H-pyrrole-2-carbonyl)-amino]-propionic acid is obtained. It was used without further purification; $^1$H NMR (DMSO-$d_6$) δ 2.47 (t, 2H, J=7.2 Hz), 3.39 (q, 2H, J=6.0 Hz), 6.90 (s, 1H), 8.17 (t, 1H, J=4.8 Hz); m/z [M$^+$+1] 340.9.

A mixture of $P_2O_5$ (100 mg) in PPA (2 g) is stirred and heated at 120° C. for 1 hour. After cooling to 100° C., 3-[(4,5-dibromo-1H-pyrrole-2-carbonyl)-amino]-propionic acid (100 mg) is added. The mixture is stirred vigorously for 2.5 hours and then cooled to room temperature. Ice-water is added and the solution is neutralized to pH4 by adding NaOH. 2,3-Dibromo-6,7-dihydro-1H,5H-pyrrolo[2,3-c]azepine-4,8-dione is collected, as precipitate, by filtration; $^1$H NMR (DMSO-$d_6$) δ 2.71-2.78 (m, 2H), 3.32-3.40 (m, 2H), 8.50 (s, 1H); m/z [M$^+$+1] 322.9.

To a solution of 2,3-dibromo-6,7-dihydro-1H,5H-pyrrolo[2,3-c]azepine-4,8-dione (2.5 g, 7.74 mmol) in a mixture of DMF-MeOH (6 mL) is added $NaBH_4$ (1.47 g, 38.7 mmol). The mixture is stirred at room temperature overnight. It is concentrated and water is added. The mixture is extracted with EtOAc, washed with brine and dried. After the solvent is removed, the residue is subjected to silica gel column chromatography and eluted with $CH_2Cl_2$-MeOH to give 2,3-dibromo-4-hydroxy-4,5,6,7-tetrahydro-1H-pyrrolo[2,3-c]azepin-8-one; $^1$H NMR (DMSO-$d_6$) δ 1.74-1.84 (m, 1H), 2.01-2.10 (m, 1H), 3.00-3.10 (m, 1H), 3.42-3.50 (m, 1H), 4.63-4.68 (m, 1H), 5.06 (d, 1H, J=6.4 Hz), 7.92 (d, 1H, J=4.4 Hz); m/z [M$^+$+1] 324.9.

The following reference compounds are synthesized by a similar procedure as outlined in reference 1 using appropriate starting materials:

Reference 2

2,3-Dichloro-4-hydroxy-4,5,6,7-tetrahydro-1H-pyrrolo[2,3-c]azepin-8-one

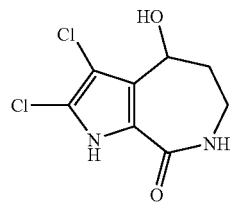

3-[(4,5-Dichloro-1H-pyrrole-2-carbonyl)-amino]-propionic acid; $^1$H NMR (DMSO-d$_6$) δ 2.50 (t, 2H, J=6.8 Hz), 3.43 (q, 2H, J=6.8 Hz), 6.90 (s, 1H), 8.23 (t, 1H, J=4.4 Hz), 12.20 (bs, 1H), 12.72 (s, 1H); m/z [M$^+$+1] 250.9.

2,3-Dichloro-6,7-dihydro-1H,5H-pyrrolo[2,3-c]azepine-4,8-dione: $^1$H NMR (DMSO-d$_6$) δ 2.72-2.78 (m, 2H), 3.38-3.42 (m, 2H), 8.54 (t, 1H, J=4.8 Hz), 13.52 (bs, 1H); m/z [M$^+$+1] 232.9.

2,3-Dichloro-4-hydroxy-4,5,6,7-tetrahydro-1H-pyrrolo[2,3-c]azepin-8-one: $^1$H NMR (DMSO-d$_6$) δ 1.75-1.84 (m, 1H), 2.00-2.10 (m, 1H), 3.00-3.08 (m, 1H), 3.42-3.50 (m, 1H), 4.68-4.72 (m, 1H), 5.13 (d, 1H, J=5.6 Hz), 7.93 (t, 1H, J=4.4 Hz), 12.43 (bs, 1H); m/z [M$^+$+1] 235.0.

Reference 3

4-Hydroxy-6-methyl-4,5,6,7-tetrahydro-1H-pyrrolo[2,3-c]azepin-8-one

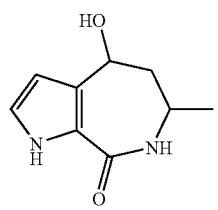

6-Methyl-6,7-dihydro-1H,5H-pyrrolo[2,3-c]azepine-4,8-dione: $^1$H NMR (DMSO-d$_6$) δ 1.21 (d, 3H, J=6.8 Hz), 2.62 (d, 1H, J=16.8 Hz), 2.78 (dd, 1H, J$_1$=6.0 Hz, J$_2$=16.8 Hz), 3.76-3.84 (m, 1H), 6.54 (d, 1H, J=2.4 Hz), 6.97 (d, 1H, J=5.6 Hz), 8.13 (d, 1H, J=2.4 Hz), 12.12 (s, 1H); m/z [M$^+$+1] 179.0.

4-Hydroxy-6-methyl-4,5,6,7-tetrahydro-1H-pyrrolo[2,3-c]azepin-8-one: $^1$H NMR (DMSO-d$_6$) δ 1.19 (d, 3H, J=6.8 Hz), 1.68-1.78 (m, 1H), 1.96-2.08 (m, 1H), 3.44-3.56 (m, 1H), 4.66-4.72 (m, 1H), 5.02 (d, 1H, J=6.8 Hz), 6.19 (t, 1H, J=3.2 Hz), 6.81 (d, 1H, J=3.2 Hz), 7.18 (s, 1H), 11.06 (s, 1H); m/z [M$^+$+1] 181.1.

Reference 4

2,3-Dibromo-4-hydroxy-6-methyl-4,5,6,7-tetrahydro-1H-pyrrolo[2,3-c]azepin-8-one

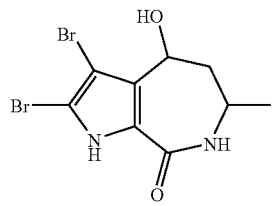

To a solution of 4-hydroxy-6-methyl-4,5,6,7-tetrahydro-1H-pyrrolo[2,3-c]azepin-8-one (18 mg, 0.1 mmol) in THF (5 mL) is added NBS (35.6 g, 0.2 mmol) at room temperature. It is stirred for 1 hour and concentrated. Sodium thiosulfate aqueous solution is added to the residue. The mixture is extracted with EtOAc twice. The organic layers are combined and dried to give 2,3-dibromo-4-hydroxy-6-methyl-4,5,6,7-tetrahydro-1H-pyrrolo[2,3-c]azepin-8-one; $^1$H NMR (DMSO-d$_6$) δ 1.16 (d, 3H, J=7.2 Hz), 1.79-1.85 (m, 1H), 2.12-2.19 (m, 1H), 3.39-3.43 (m, 1H), 4.65-4.72 (m, 1H), 4.91 (d, 1H, J=6.8 Hz), 7.67 (s, 1H), 11.04 (s, 1H); m/z [M$^+$+1] 338.9.

Reference 6

7-Bromo-5-hydroxy-3,4,5,10-tetrahydro-2H-azepino[3,4-b]indol-1-one

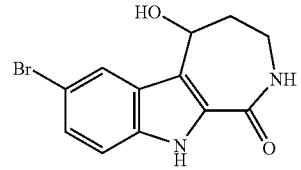

7-Bromo-3,4-dihydro-2H,10H-azepino[3,4-b]indole-1,5-dione: $^1$H NMR (DMSO-d$_6$) δ2.82-2.88 (m, 2H), 3.43-3.51 (m, 2H), 7.45-7.51 (m, 2H), 8.44 (s, 1H), 8.81 (s, 1H), 12.66 (s, 1H); m/z [M$^+$+1] 293.0.

7-Bromo-5-hydroxy-3,4,5,10-tetrahydro-2H-azepino[3,4-b]indol-1-one: $^1$H NMR (DMSO-d$_6$) δ 1.97-2.06 (m, 1H), 2.08-2.16 (m, 1H), 3.10-3.21 (m, 1H), 3.43-3.52 (m, 1H), 5.09-5.13 (m, 1H), 5.32 (d, 1H, J=6.4 Hz), 7.31 (d, 1H, J=8.0 Hz), 7.37 (d, 1H, J=8.0 Hz), 7.94 (s, 1H), 8.20 (s, 1H), 11.48 (s, 1H); m/z [M$^+$+1] 295.0.

Reference 7

5-Hydroxy-3,4,5,10-tetrahydro-2H-azepino[3,4-b]indol-1-one

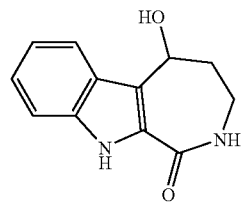

3,4-Dihydro-2H,10H-azepino[3,4-b]indole-1,5-dione: $^1$H NMR (DMSO-d$_6$) δ 2.82-2.86 (m, 2H), 3.44-3.50 (m, 2H), 7.25 (t, 1H, J=7.2 Hz), 7.32 (d, 1H, J=7.2 Hz), 7.53 (d, 1H, J=8.0 Hz), 8.30 (d, 1H, J=8.0 Hz), 8.74 (t, 1H, J=5.2 Hz), 12.46 (s, 1H); m/z [M$^+$+1] 215.0.

5-Hydroxy-3,4,5,10-tetrahydro-2H-azepino[3,4-b]indol-1-one: $^1$H NMR (DMSO-d$_6$) δ 1.96-2.06 (m, 1H), 2.10-2.20 (m, 1H), 3.10-3.20 (m, 1H), 3.46-3.56 (m, 1H), 5.10-5.17 (m, 1H), 5.20 (d, 1H, J=6.8 Hz), 7.04 (t, 1H, J=7.2 Hz), 7.19 (t, 1H, J=6.8 Hz), 7.41 (d, 1H, J=7.2 Hz), 7.78 (d, 1H, J=6.8 Hz), 8.13 (s, 1H), 11.25 (s, 1H); m/z [M$^+$+1] 217.1.

Reference 8

7-Bromo-3-methyl-3,4-dihydro-2H,10H-azepino[3,4-b]indole-1,5-dione

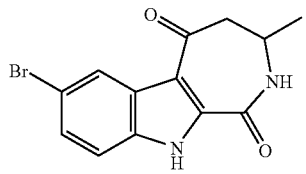

$^1$H NMR (DMSO-d$_6$) δ 1.24 (d, 3H, J=6.8 Hz), 2.73 (d, 1H, J=16.4 Hz), 2.92 (dd, 1H, J$_1$=10.4 Hz, J$_2$=16.4 Hz), 3.90-4.00 (m, 1H), 7.43-7.50 (m, 2H), 8.41 (d, 1H, J=1.0 Hz), 8.66 (d, 1H, J=3.6 Hz); m/z [M$^+$+1] 309.0.

Reference 9

7-Chloro-5-hydroxy-3,4,5,10-tetrahydro-2H-azepino[3,4-b]indol-1-one

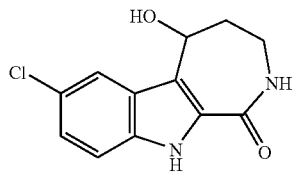

$^1$H NMR (DMSO-d$_6$) δ 1.96-2.04 (m, 1H), 2.08-2.16 (m, 1H), 3.10-3.18 (m, 1H), 3.42-3.50 (m, 1H), 5.09 (q, 1H, J=5.2 Hz), 5.28 (d, 1H, J=7.2 Hz), 7.18 (dd, 1H, J$_1$=1.6 Hz, J$_2$=8.8 Hz), 7.39 (d, 1H, J=8.8 Hz), 7.77 (d, 1H, J=1.6 Hz), 8.18 (t, 1H, J=4.8 Hz), 11.45 (s, 1H); m/z [M$^+$+1] 251.0.

Reference 10

(1-Oxo-1,2,3,10-tetrahydro-azepino[3,4-b]indol-5-yl)-acetic acid

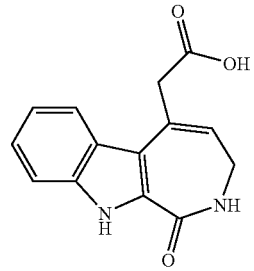

A solution of 5-ethoxycarbonylmethylene-1-oxo-1,3,4,5-tetrahydro-azepino[3,4-b]indole-2,10-dicarboxylic acid di-tert-butyl ester, (0.496 g, 1.02 mmol) and LiOH (0.246 g, 10.2 mmol) in MeOH—H$_2$O (1:1 mixture, 50 mL) is stirred at room temperature for 2 days before it is concentrated. Water is added to the residue and it is acidified with NaHSO$_4$ (2M). The solid that is precipitated is collected by vacuum filtration and dried to yield (1-oxo-1,2,3,10-tetrahydro-azepino[3,4-b]indol-5-yl)-acetic acid; $^1$H NMR (DMSO-d$_6$) δ 2.50 (t, 2H, J=5.6 Hz), 2.82 (s, 1H), 5.00 (t, 1H, J=6.4 Hz), 6.18 (t, 1H, J=7.2 Hz), 6.34 (t, 1H, J=7.2 Hz), 6.56 (d, 1H, J=8.8 Hz), 6.90 (d, 1H, J=8.8 Hz), 7.21 (t, 1H, J=4.4 Hz), 10.98 (s, 1H); m/z [M$^+$+1] 257.0.

Reference 11

5-Fluoro-1H-indole-2-carboxylic acid (3-hydroxy-propyl)-amide

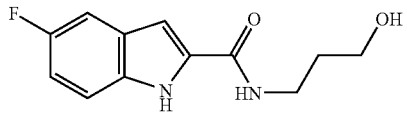

To a solution of 5-fluoro-1H-indole-2-carboxylic acid (2.27 g, 12.7 mmol) in CH$_2$Cl$_2$ (100 mL) is added DMAP (4.64 g, 38 mmol), EDCI (3.64 g, 19 mmol), 3-amino-propan-1-ol (1.90 g, 25 mmol). The mixture is stirred at room temperature for 24 hours. After the solvent is removed under vacuum, 5% HCl (100 mL) is added to the mixture. It is extracted with EtOAc (100 mL×3). The combined organic layers are washed with saturated aqueous NaHCO$_3$ (100 mL), brine (100 mL) and dried with Na$_2$SO$_4$. Solvent is removed to give 5-fluoro-1H-indole-2-carboxylic acid (3-hydroxy-propyl)-amide; $^1$H NMR (DMSO-d$_6$) δ 1.69 (quint, 2H, J=6.4 Hz), 3.34 (q, 2H, J=6.0 Hz), 3.48 (t, 2H, J=6.4 Hz), 4.48 (bs, 1H), 6.99-7.10 (m, 2H), 7.36-7.44 (m, 2H), 8.47 (t, 1H, J=5.6 Hz), 11.63 (s, 1H); m/z [M$^+$+1] 237.1.

Reference 12

5-Fluoro-3-iodo-1H-indole-2-carboxylic acid (3-hydroxy-propyl)-amide

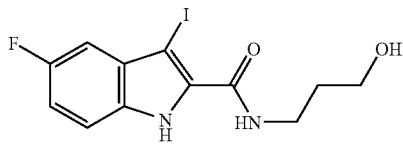

To a solution of 5-fluoro-1H-indole-2-carboxylic acid (3-hydroxy-propyl)-amide, prepared as in reference 11, (4.89 g, 20.7 mmol) in DMF (100 mL) is added KOH (3.48 g, 62 mmol) and $I_2$ (5.78 g, 22.8 mmol). It is stirred at room temperature for 1 hour and concentrated. Water is added to the residue and the mixture is acidified with HCl. The mixture is extracted with EtOAc (100 mL×2). The combined organic layers are washed with $Na_2S_2O_3$ (1M, 50 mL), brine (100 mL), and dried with $Na_2SO_4$. Solvent is removed to give 5-fluoro-3-iodo-1H-indole-2-carboxylic acid (3-hydroxy-propyl)-amide; $^1$H NMR (DMSO-$d_6$) δ 1.73 (quint, 2H, J=6.0 Hz), 3.39 (q, 2H, J=6.0 Hz), 3.54 (t, 2H, J=6.0 Hz), 4.54 (bs, 1H), 7.06-7.16 (m, 2H), 7.46 (dd, 1H, $J_1$=4.4 Hz, $J_2$=8.8 Hz), 8.00 (t, 1H, J=6.0 Hz), 12.10 (s, 1H); m/z [M$^+$+1] 363.0.

Reference 13

5-Fluoro-3-iodo-1H-indole-2-carboxylic acid (3-oxo-propyl)-amide

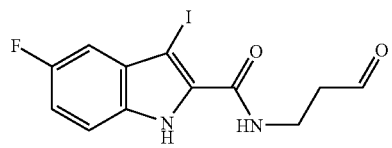

To a solution of oxalyl chloride (3.68 g, 30 mmol) in anhydrous $CH_2Cl_2$ (50 mL) at −40° C. is added DMSO (4.52 g, 57.9 mmol) drop-wise. The mixture is stirred at this temperature for 5 minutes. 5-Fluoro-3-iodo-1H-indole-2-carboxylic acid (3-hydroxy-propyl)-amide, prepared as in reference 12, (6.99 g, 19.3 mmol) is dissolved in $CH_2Cl_2$ (800 mL) with small amount of DMSO (10 mL) and added to the above-mentioned solution at −40° C. The reaction is stirred for additional 30 minutes before adding $Et_3N$ (11.7 g, 0.116 mol). The mixture is allowed to warm to room temperature and quenched with $H_2O$ (1 L). The organic layer is separated and washed with citric acid (10%, 500 mL), saturated $NaHCO_3$ (500 mL) and brine (500 mL). It is dried with $Na_2SO_4$ to give 5-fluoro-3-iodo-1H-indole-2-carboxylic acid (3-oxo-propyl)-amide; $^1$H NMR (DMSO-$d_6$) δ 2.75 (dt, 2H, $J_1$=1.2 Hz, $J_2$=6.0 Hz), 3.61 (q, 2H, J=5.2 Hz), 7.06-7.17 (m, 2H), 7.45 (dd, 1H, $J_1$=4.8 Hz, $J_2$=8.8 Hz), 8.11 (t, 1H, J=5.6 Hz), 9.74 (t, 1H, 1.2 Hz), 12.10 (s, 1H); m/z [M$^+$+1] 361.0.

Reference 14

5-[(5-Fluoro-3-iodo-1H-indole-2-carbonyl)-amino]-pent-2-enoic acid ethyl ester

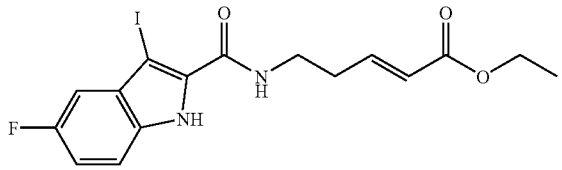

To a solution of 5-fluoro-3-iodo-1H-indole-2-carboxylic acid (3-oxo-propyl)-amide, prepared as in reference 13, (5.86 g, 16.3 mmol) in THF (200 mL) is added (carbethoxymethylene)triphenylphosphorane (18 g, 51.7 mmol) at 0° C. The reaction is stirred at room temperature overnight. It is washed with saturated $NH_4Cl$ (200 mL) and extracted with $Et_2O$ (200 mL×2). The combined organic layers are washed with brine and dried. It is concentrated and purified by silica gel column chromatography and eluted with EtOAc-Hexanes to give 5-[(5-fluoro-3-iodo-1H-indole-2-carbonyl)-amino]-pent-2-enoic acid ethyl ester as the trans isomer; $^1$H NMR (DMSO-$d_6$) δ 1.25 (t, 3H, J=6.8 Hz), 2.52 (t, 2H, J=6.8 Hz), 3.48 (q, 2H, J=5.6 Hz), 4.10 (q, 2H, 6.8 Hz), 5.96 (d, 1H, J=15.6 Hz), 6.96 (dt, 1H, $J_1$=5.8 Hz, $J_2$=15.6 Hz), 7.06-7.18 (m, 2H), 7.46 (dd, 1H, $J_1$=4.0 Hz, $J_2$=8.8 Hz), 8.11 (t, 1H, J=6.4 Hz), 12.10 (s, 1H); m/z [M$^+$+1] 431.0.

Reference 15

2-[tert-Butoxycarbonyl-(4-ethoxycarbonyl-but-3-enyl)-aminocarbonyl]-5-fluoro-3-iodo-indole-1-carboxylic acid tert-butyl ester

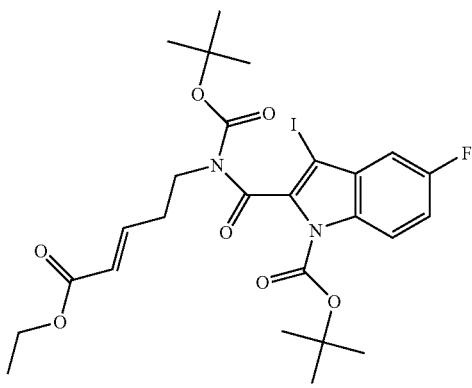

To a solution of 5-[(5-fluoro-3-iodo-1H-indole-2-carbonyl)-amino]-pent-2-enoic acid ethyl ester, prepared as in reference 14, (4.15 g, 9.65 mmol) in MeCN (100 mL) is added DMAP (2.59 g, 21.2 mmol) and di-tert-butyl dicarbonate (6.33 g, 28.9 mmol). The reaction is stirred at room temperature overnight. It is concentrated and EtOAc (100 mL) is added. It is washed with $NaHSO_4$ (2M, 100 mL) and brine (100 mL). The organic layer is dried, concentrated and purified by silica gel column chromatography and eluted with EtOAc-Hexanes to give 2-[tert-butoxycarbonyl-(4-ethoxycarbonyl-but-3-enyl)-aminocarbonyl]-5-fluoro-3-iodo-indole-1-carboxylic acid tert-butyl ester; $^1$H NMR (CDCl$_3$) δ

1.29 (t, 3H, J=7.2 Hz), 1.54 (s, 9H), 1.60 (s, 9H), 2.71 (q, 2H, J=7.2 Hz), 3.86-3.94 (m, 1H), 4.16-4.21 (m, 1H), 4.19 (q, 2H, J=7.2 Hz), 5.99 (d, 1H, J=15.6 Hz), 6.98-7.14 (m, 3H), 8.06 (dd, 1H, J$_1$=4.4 Hz, J$_2$=8.8 Hz); m/z [M$^+$+Na] 653.1.

Reference 16

(7-Fluoro-1-oxo-1,2,3,10-tetrahydro-azepino[3,4-b]indol-5-yl)-acetic acid

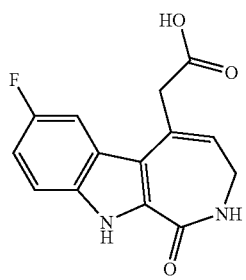

A suspension of triphenylphosphine (3.36 g, 12.8 mmol), Pd(OAc)$_2$ (1.44 g, 6.40 mmol) and Ag$_2$CO$_3$ (3.53 g, 12.8 mmol) in anhydrous THF (100 mL) is stirred at room temperature for 15 minutes. A solution of 2-[tert-butoxycarbonyl-(4-ethoxycarbonyl-but-3-enyl)-aminocarbonyl]-5-fluoro-3-iodo-indole-1-carboxylic acid tert-butyl ester (4.03 g, 6.40 mmol), prepared as in reference 15, in THF (10 mL) is added to the above prepared suspension. The mixture is heated at 60° C. for 16 hours. The inorganic precipitate is removed and the organic layer is concentrated. The residue is purified by silica gel column chromatography and eluted with EtOAc-Hexanes to give the 5-ethoxycarbonylmethylene-7-fluoro-1-oxo-1,3,4,5-tetrahydro-azepino[3,4-b]indole-2,10-dicarboxylic acid di-tert-butyl ester; $^1$H NMR (CDCl$_3$) δ 1.34 (t, 3H, J=7.6 Hz), 1.57 (s, 9H), 1.60 (s, 9H), 3.46-3.52 (m, 2H), 4.13 (t, 2H, J=4.8 Hz), 4.24 (q, 2H, J=7.6 Hz), 6.30 (t, 1H, J=2.8 Hz), 7.21 (td, 1H, J$_1$=2.8 Hz, J$_2$=9.2 Hz), 7.42 (dd, 1H, J$_1$=2.8 Hz, J$_2$=8.8 Hz), 8.10 (dd, 1H, J$_1$=4.0 Hz, J$_2$=9.2 Hz); m/z [M$^+$+Na] 525.0.

To a solution of 5-ethoxycarbonylmethylene-7-fluoro-1-oxo-1,3,4,5-tetrahydro-azepino[3,4-b]indole-2,10-dicarboxylic acid di-tert-butyl ester, (1.31 g, 2.6 mmol) in MeOH—H$_2$O (3:1 mixture, 150 mL) is added LiOH (0.312 g, 13 mmol). The mixture is stirred at room temperature for 2 days and concentrated. Water (100 mL) is added to the residue and it is acidified with 2M NaHSO$_4$. The precipitate is collected by filtration and dried to give (7-fluoro-1-oxo-1,2,3,10-tetrahydro-azepino[3,4-b]indol-5-yl)-acetic acid; $^1$H NMR (DMSO-d$_6$) δ 2.26 (d, 2H, J=5.2 Hz), 2.79 (s, 2H), 5.00 (t, 1H, 6.4 Hz), 6.22 (dt, 1H, J$_1$=2.4 Hz, J$_2$=10.8 Hz), 6.56 (dd, 1H, J$_1$=4.0 Hz, J$_2$=8.8 Hz), 6.66 (dd, 1H, J$_1$=2.4 Hz, J$_2$=10.8 Hz), 7.26 (t, 1H, J=5.6 Hz), 11.10 (s, 1H); m/z [M$^+$+1] 275.0.

Reference 17

(7-Fluoro-1-oxo-1,2,3,10-tetrahydro-azepino[3,4-b]indol-5-yl)-acetyl azide

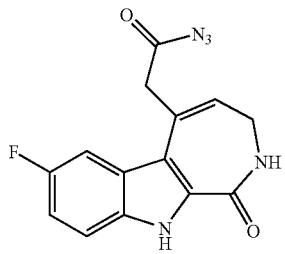

To an ice-cold solution of (7-fluoro-1-oxo-1,2,3,10-tetrahydro-azepino[3,4-b]indol-5-yl)-acetic acid (0.99 g, 3.6 mmol) and triethylamine (0.36 g, 3.6 mmol) in dry DMF (10 mL) was added in dropwise a solution of diphenylphosphoryl azide (0.99 g, 3.6 mmol), in DMF (5 mL) over a period of 2 h. After removal of the cooling bath, the mixture was stirred at room temperature for 12 h. It was poured into ice and the precipitate therefore formed was collected by vacuum filtration, which appeared to be the title compound (0.10 g). Extract the rest part of the mixture with ethyl acetate (20 mL×2). The organic layers were combined, washed with saturated aqueous NaHCO$_3$, brine, and dried over anhydrous Na$_2$SO$_4$. It was concentrated and the oil obtained was treated with diethyl ether to give additional title compound as a solid precipitate (0.23 g).

Example 1

4-(2-Amino-3H-imidazol-4-yl)-2,3-dichloro-4,5,6,7-tetrahydro-1H-pyrrolo[2,3-c]azepin-8-one

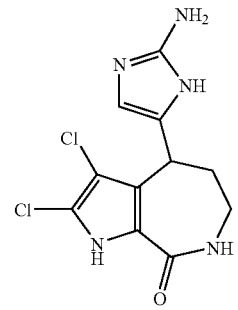

To a solution of 2,3-dichloro-4-hydroxy-4,5,6,7-tetrahydro-1H-pyrrolo[2,3-c]azepin-8-one (60 mg, 0.256 mmol), prepared as in reference 2, in methanesulfonic acid (0.5 mL) is added 2-aminoimidazole sulfate (40.5 mg, 0.153 mmol). The mixture is stirred at 45° C. overnight, cooled to room temperature and Et$_2$O (5 mL) is added resulting in brown oil. After discarding the supernatant, the oil is purified by silica gel column chromatography and eluted with MeOH—CH$_2$Cl$_2$ to give 4-(2-amino-3H-imidazol-4-yl)-2,3-dichloro-4,5,6,7-tetrahydro-1H-pyrrolo[2,3-c]azepin-8-one; $^1$H NMR (Methanol-d$_4$) δ 2.09-2.17 (m, 1H), 2.23-2.31 (m, 1H), 3.20-3.29 (m, 2H), 4.23 (t, 1H, J=3.6 Hz), 6.18 (s, 1H); m/z [M$^+$+1] 300.0.

Example 2

4-(2-Amino-5-oxo-3,5-dihydro-imidazol-4-ylidene)-2,3-dichloro-4,5,6,7-tetrahydro-1H-pyrrolo[2,3-c]azepin-8-one

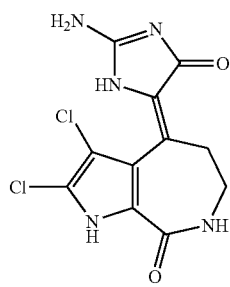

To a solution of 4-(2-amino-3H-imidazol-4-yl)-2,3-dichloro-4,5,6,7-tetrahydro-1H-pyrrolo[2,3-c]azepin-8-one, prepared as in reference 2, (38 mg, 0.13 mmol) in AcOH (3 mL) is added NaOAc trihydrate (86 mg, 0.63 mmol). A solution of $Br_2$ (40 mg, 0.25 mmol) in AcOH (1 mL) is added drop-wise, the mixture is stirred for an additional 30 minutes and concentrated. The residue is purified by HPLC ($C_{18}$ column, eluted with $CH_3CN-H_2O$ containing 0.05% TFA) to give 4-(2-amino-5-oxo-3,5-dihydro-imidazol-4-ylidene)-2,3-dichloro-4,5,6,7-tetrahydro-1H-pyrrolo[2,3-c]azepin-8-one; $^1$H NMR (DMSO-$d_6$) δ 3.18-3.26 (m, 2H), 3.26-3.32 (m, 2H), 8.09 (t, 1H, J=4.8 Hz), 8.68 (s, 1H), 9.37 (s, 2H), 11.11 (s, 1H), 13.46 (s, 1H); m/z [M$^+$+1] 314.0.

Example 3

2-[N'-(2,3-Dibromo-8-oxo-5,6,7,8-tetrahydro-1H-pyrrolo[2,3-c]azepin-4-ylidene)-hydrazino]-benzoic acid

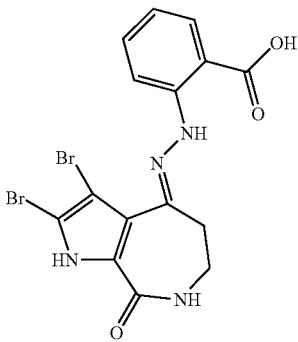

To a solution of 2,3-dibromo-6,7-dihydro-1H,5H-pyrrolo[2,3-c]azepine-4,8-dione (32.2 mg, 0.10 mmol) in EtOH (5 mL) is added 2-hydrazinobenzoic acid (22.6 mg, 0.12 mmol) and HCl in i-PrOH (6N, 0.3 mL). The mixture is refluxed for 2 hours and then concentrated under reduced pressure. The residue is purified by HPLC ($C_{18}$ column, eluted with $CH_3CN/H_2O$ with 0.05% TFA) to give 2-[N'-(2,3-dibromo-8-oxo-5,6,7,8-tetrahydro-1H-pyrrolo[2,3-c]azepin-4-ylidene)-hydrazino]-benzoic acid; $^1$H NMR (DMSO-$d_6$) δ 2.80-2.86 (m, 2H), 3.30-3.34 (m, 2H), 6.82 (t, 1H, J=8.0 Hz), 7.51 (d, 1H, J=7.2 Hz), 7.83-7.88 (m, 2H), 8.13 (t, 1H, J=6.0 Hz), 11.03 (s, 1H), 12.95 (s, 1H), 13.13 (s, 1H); m/z [M$^+$+1] 456.9.

Example 4

5-(2-Amino-5-oxo-3,5-dihydro-imidazol-4-ylidene)-3,4,5,10-tetrahydro-2H-azepino[3,4-b]indol-1-one

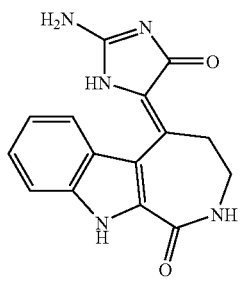

To a solution of 5-(2-amino-5-oxo-3,5-dihydro-imidazol-4-ylidene)-7-bromo-3,4,5,10-tetrahydro-2H-azepino[3,4-b]indol-1-one TFA salt (13 mg, 0.027 mmol), in MeOH (5 mL) is added sodium acetate trihydrate (24 mg, 0.18 mmol) and 10% Pd/C (4.5 mg). It is stirred at room temperature under a hydrogen atmosphere overnight and then the catalyst is removed by filtration. The solution is concentrated and the residue is purified by HPLC ($C_{18}$ column, eluted with $CH_3CN/H_2O$ with 0.05% TFA) to give 5-(2-amino-5-oxo-3,5-dihydro-imidazol-4-ylidene)-3,4,5,10-tetrahydro-2H-azepino[3,4-b]indol-1-one; $^1$H NMR (DMSO-$d_6$) δ 3.30-3.36 (m, 4H), 7.20 (t, 1H, J=7.6 Hz), 7.33 (t, 1H, J=7.2 Hz), 7.53 (t, 1H, J=7.6 Hz), 7.58 (d, 1H, J=7.2 Hz), 8.36 (t, 1H, J=2.4 Hz), 9.20 (bs, 1H), 10.37 (bs, 1H), 12.45 (s, 1H); m/z [M$^+$+1] 296.1.

Example 5

9-Amino-5-(2-amino-5-oxo-3,5-dihydro-imidazol-4-ylidene)-3,4,5,10-tetrahydro-2H-azepino[3,4-b]indol-1-one

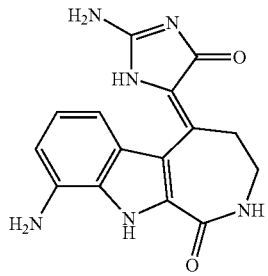

To a solution of 5-(2-amino-5-oxo-3,5-dihydro-imidazol-4-ylidene)-9-nitro-3,4,5,10-tetrahydro-2H-azepino[3,4-b]indol-1-one TFA salt (4 mg, 8.8 μmol) in MeOH (3 mL) is added 10% Pd/C (10 mg). The mixture is stirred at room temperature under hydrogen atmosphere overnight and then the catalyst is removed by filtration. The solution is concentrated and the residue purified by HPLC ($C_{18}$ column, eluted with $CH_3CN/H_2O$ with 0.05% TFA) to give 9-amino-5-(2-amino-5-oxo-3,5-dihydro-imidazol-4-ylidene)-3,4,5,10-tetrahydro-2H-azepino[3,4-b]indol-1-one; $^1$H NMR (MeOD-d$_4$) δ 3.48-3.53 (m, 4H), 7.358 (d, 1H, J=6.0 Hz), 7.362 (d, 1H, J=3.2 Hz), 7.63 (dd, 1H, J$_1$=3.2 Hz, J$_2$=6.0 Hz); m/z [M$^+$+1] 311.1.

Example 6

(1-Oxo-1,2,3,10-tetrahydro-azepino[3,4-b]indol-5-yl)-acetic acid

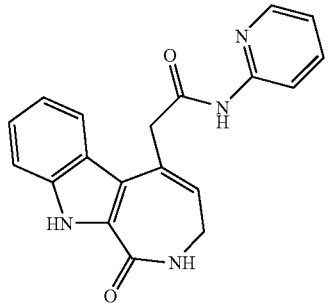

To a solution of (1-oxo-1,2,3,10-tetrahydro-azepino[3,4-b]indol-5-yl)-acetic acid, prepared as in reference 10, (15 mg, 0.062 mmol) in DMF (1 mL) is added DIEA (24 mg, 0.186 mmol), HATU (26 mg, 0.068 mmol) and 2-aminopyridine (17 mg, 0.186 mmol). The mixture is stirred at room temperature for 2 hours and concentrated. The residue is purified by HPLC (C$_{18}$ column, eluted with CH$_3$CN/H$_2$O with 0.05% TFA) to give (1-oxo-1,2,3,10-tetrahydro-azepino[3,4-b]indol-5-yl)-acetic acid; $^1$H NMR (DMSO-d$_6$) δ 3.40 (t, 2H, J=5.6 Hz), 3.94 (s, 2H), 5.94 (t, 1H, J=7.2 Hz), 7.06 (t, 2H, J=6.8 Hz), 7.23 (dd, 1H, J$_1$=6.8 Hz, J$_2$=14 Hz), 7.46 (d, 1H, J=8.0 Hz), 7.71 (t, 1H, J=8.0 Hz), 7.95 (d, 2H, J=8.0 Hz), 8.13 (t, 1H, J=5.2 Hz), 8.28 (d, 1H, J=3.6 Hz), 10.59 (s, 1H), 11.89 (s, 1H); m/z [M$^+$+1] 333.1.

Example 7

N-(6-Chloro-pyridin-3-yl)-2-(7-fluoro-1-oxo-1,2,3,10-tetrahydro-azepino[3,4-b]indol-5-yl)-acetamide

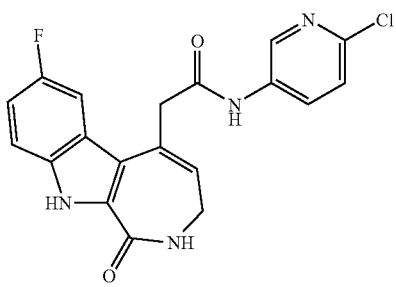

To a solution of (7-fluoro-1-oxo-1,2,3,10-tetrahydro-azepino[3,4-b]indol-5-yl)-acetic acid, prepared as in reference 16, (25 mg, 0.091 mmol) in DMF (1 mL) is added DIEA (35.4 mg, 0.274 mmol), HATU (38.2 mg, 0.100 mmol) and 6-chloro-pyridin-3-ylamine (35.2 mg, 0.274 mmol). The mixture is stirred at room temperature for 2 hours and concentrated. The residue is purified by HPLC (C$_{18}$ column, eluted with CH$_3$CN/H$_2$O with 0.05% TFA) to give N-(6-Chloro-pyridin-3-yl)-2-(7-fluoro-1-oxo-1,2,3,10-tetrahydro-azepino[3,4-b]indol-5-yl)-acetamide; $^1$H NMR (DMSO-d$_6$) δ 3.43 (t, 2H, J=5.6 Hz), 3.84 (s, 2H), 5.96 (t, 1H, J=7.2 Hz), 7.12 (dt, 1H, J$_1$=2.4 Hz, J$_2$=8.8 Hz), 7.43 (d, 1H, J=8.8 Hz), 7.46 (dd, 1H, J$_1$=4.4 Hz, J$_2$=8.8 Hz), 7.67 (dd, 1H, J$_1$=2.4 Hz, J$_2$=10.8 Hz), 8.01 (dd, 1H, J$_1$=2.8 Hz, J$_2$=8.0 Hz), 8.19 (t, 1H, J=5.2 Hz), 8.54 (d, 1H, J=3.2 Hz), 10.48 (s, 1H), 12.04 (s, 1H); m/z [M$^+$+1] 385.0.

Example 8

1-(7-Fluoro-1-oxo-1,3,4,10-tetrahydro-2H-azepino[3,4-b]indol-5-ylidenemethyl)-3-pyridin-3-yl-urea

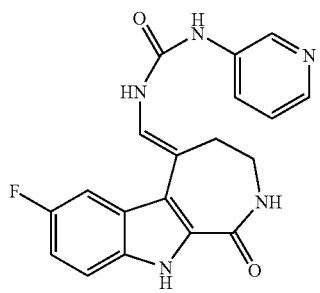

A suspension of (7-Fluoro-1-oxo-1,2,3,10-tetrahydro-azepino[3,4-b]indol-5-yl)-acetyl azide, prepared as in reference 17, (10 mg, 0.33 mmol) in dry toluene (1 mL) is heated at 110° C. for 15 minutes. To this mixture is added pyridin-3-ylamine (16 mg, 0.17 mmol) and it is heated at the same temperature for 1 hour. Toluene is removed in vacuum and the residue is purified by HPLC (C$_{18}$ column, eluted with CH$_3$CN/H$_2$O with 0.5% TFA) to afford 1-(7-Fluoro-1-oxo-1,3,4,10-tetrahydro-2H-azepino[3,4-b]indol-5-ylidenemethyl)-3-pyridin-3-yl-urea; $^1$H NMR (DMSO-d$_6$) δ 2.73-2.78 (m, 2H), 3.33-3.37 (m, 2H), 7.10-7.18 (m, 2H), 7.43-7.48 (m, 2H), 8.69 (d, 1H, J=10.8 Hz), 8.87 (s, 1H), 9.46 (s, 1H), 10.66 (s, 1H); m/z [M$^+$+1] 366.1.

Example 9

N-(2-Dimethylamino-ethyl)-2-(7-fluoro-1-oxo-1,3,4,10-tetrahydro-2H-azepino[3,4-b]indol-5-ylidene)-acetamide

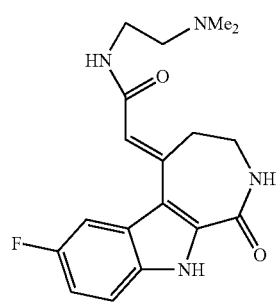

A suspension of (7-Fluoro-1-oxo-1,2,3,10-tetrahydro-azepino[3,4-b]indol-5-yl)-acetyl azide, prepared as in reference 17, (10 mg, 0.33 mmol) and N,N-dimethylethylene-diamine (15 mg, 0.17 mmol) in dry toluene (1 mL) is heated at 110° C.

for 1 hour. Toluene is removed in vacuum and the residue is purified by HPLC (C₁₈ column, eluted with CH₃CN/H₂O with 0.5% TFA) to afford N-(2-dimethylamino-ethyl)-2-(7-fluoro-1-oxo-1,3,4,10-tetrahydro-2H-azepino[3,4-b]indol-5-ylidene)-acetamide; ¹H NMR (DMSO-d₆) δ 2.85 (s, 6H), 3.19-3.22 (m, 2H), 3.25-3.30 (m, 2H), 3.44-3.48 (m, 2H), 3.49 (q, 2H, J=6.8 Hz), 6.34 (s, 1H), 7.18 (dt, 1H, J₁=2.8 Hz, J₂=8.8 Hz), 7.50 (dd, 1H, J₁=4.4 Hz, J₂=8.8 Hz), 7.74 (dd, 1H, J₁=2.8 Hz, J₂=10.4 Hz), 8.39-8.44 (m, 2H), 9.36 (bs, 1H), 12.12 (s, 1H); m/z [M⁺+1] 345.1.

The following examples of Table 1 are synthesized by similar procedures, as outlined in the above examples, using appropriate starting materials:

TABLE 1

| Compound | Structure | Physical Data |
|---|---|---|
| 3 | 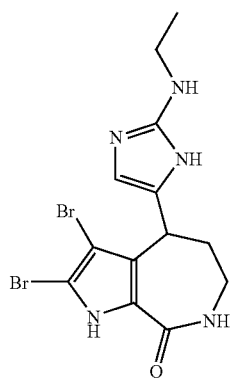 | ¹H NMR (Methanol-d₄) δ 1.28 (t, 3H, J = 7.2 Hz), 2.12-2.22 (m, 1H), 2.28-2.36 (m,1H), 3.26-3.34 (m, 4H), 4.24 (t, 1H, J = 4.4 Hz), 6.20 (s, 1H); m/z [M⁺ + 1] 417.9. |
| 4 | 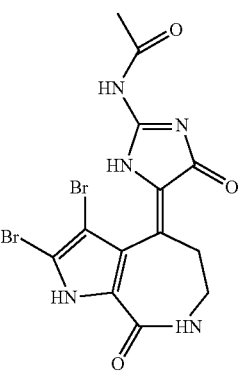 | ¹H NMR (DMSO-d₆) δ 2.08 (s, 3H), 3.22-3.30 (m, 4H), 7.99 (t, 1H, J = 4.4 Hz), 13.15 (s, 1H); m/z [M⁺+ 1] 445.9. |
| 5 | 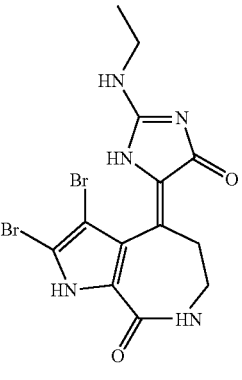 | ¹H NMR (DMSO-d₆) δ 1.15 (t, 3H, J = 7.2 Hz), 3.20-3.40 (m, 4H), 3.71 (q, 2H, J = 7.2 Hz), 8.09 (t, 1H, J = 2.4 Hz), 13.44 (s, 1H); m/z [M⁺ + 1] 431.9. |

TABLE 1-continued

| Compound | Structure | Physical Data |
|---|---|---|
| 6 | 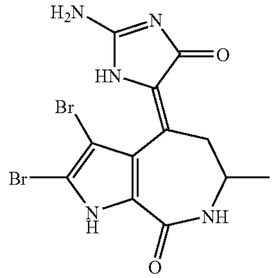 | $^1$H NMR (DMSO-d$_6$) δ 1.21 (d, 3H, J = 6.8 Hz), 2.90-3.00 (m, 1H), 3.64-3.72 (m, 2H), 7.91 (t, 1H, J = 4.4 Hz), 8.62 (bs, 1H), 9.40 (bs, 1H), 11.01 (bs, 1H), 13.37 (s, 1H); m/z [M$^+$ + 1] 417.9. |
| 7 | 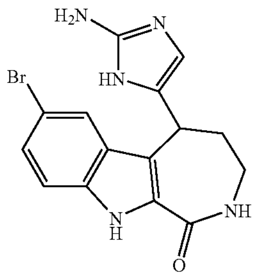 | $^1$H NMR (MeOD-d$_4$) δ 2.23-2.28 (m, 2H), 3.23-3.24 (m, 2H), 4.55 (t, 1H, J = 5.2 Hz), 6.12 (s, 1H), 7.27 (dd, 1H, J$_1$ = 1.4 Hz, J$_2$ = 8.8 Hz), 7.35 (d, 1H, J = 8.8 Hz), 7.46 (d, 1H, J = 1.4 Hz); m/z [M$^+$ + 1] 360.0. |
| 8 | 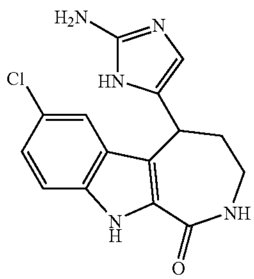 | $^1$H NMR (MeOD-d$_4$) δ 2.27-2.33 (m, 2H), 3.32-3.37 (m, 2H), 4.59 (t, 1H, J = 4.8 Hz), 6.20 (s, 1H), 7.14 (d, 1H, J = 8.8 Hz), 7.30 (s, 1H), 7.41 (d, 1H, J = 8.8 Hz); m/z [M$^+$ + 1] 316.1. |
| 9 | 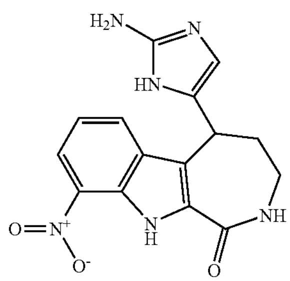 | $^1$H NMR (MeOD-d$_4$) δ 2.37-2.43 (m, 2H), 3.44 (q, 2H, J = 5.4 Hz), 4.77 (t, 1H, J = 5.4 Hz), 6.30 (s, 1H), 7.24 (t, 1H, J = 8.0 Hz), 7.89 (d, 1H, J = 8.0 Hz), 8.25 (d, 1H, J = 8.0 Hz); m/z [M$^+$ + 1] 327.1. |
| 10 | 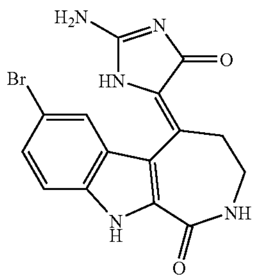 | $^1$H NMR (MeOD-d$_4$) δ 3.45-3.50 (m, 4H), 7.46-7.54 (m, 2H), 7.78 (d, 1H, J = 1.2 Hz); m/z [M$^+$ + 1] 374.0. |

TABLE 1-continued

| Compound | Structure | Physical Data |
|---|---|---|
| 11 | (structure) | $^1$H NMR (MeOD-d$_4$) δ 3.44-3.52 (m, 4H), 7.36 (dd, 1H, J$_1$ = 2.8 Hz, J$_2$ = 8.8 Hz), 7.57 (d, 1H, J = 8.8 Hz), 7.63 (d, 1H, J = 1.2 Hz); m/z [M$^+$ + 1] 330.0. |
| 12 | (structure) | $^1$H NMR (DMSO-d$_6$) δ 3.20-3.50 (m, 4H), 7.17 (dt, 1H, J$_1$ = 2.0 Hz, J$_2$ = 9.6 Hz), 7.41 (dd, 1H, J$_1$ = 2.4 Hz, J$_2$ = 9.6 Hz), 7.52 (dd, 1H, J$_1$ = 2.8 Hz, J$_2$ = 8.8 Hz), 8.37 (bs, 2H), 9.18 (bs, 1H), 10.49 (bs, 1H), 12.51 (bs, 1H); m/z [M$^+$ + 1] 314.1. |
| 13 | (structure) | $^1$H NMR (MeOD-d$_4$) δ 3.49-3.54 (m, 4H), 7.48 (t, 1H, J = 8.0 Hz), 8.10 (d, 1H, J = 8.0 Hz), 8.38 (d, 1H, J = 8.0 Hz); m/z [M$^+$ + 1] 341.1. |
| 14 | (structure) | $^1$H NMR (MeOD-d$_4$) δ 2.17 (s, 3H), 3.46-3.51 (m, 2H), 3.52-3.58 (m, 2H), 7.40-7.50 (m, 2H), 7.78 (s, 1H); m/z [M$^+$ + 1] 416.0. |
| 15 | (structure) | $^1$H NMR (DMSO-d$_6$) δ 1.25 (d, 3H, J = 6.8 Hz), 3.00-3.20 (m, 1H), 3.30-3.55 (m, 2H), 7.38-7.50 (m, 2H), 7.83 (s, 1H), 8.26 (d, 1H, J = 2.8 Hz), 8.47 (s, 2H), 9.30 (s, 1H), 10.57 (s, 1H), 12.56 (s, 1H); m/z [M$^+$ + 1] 388.0. |

TABLE 1-continued

| Compound | Structure | Physical Data |
|---|---|---|
| 16 | 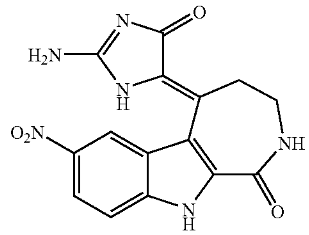 | $^1$H NMR (DMSO-d$_6$) δ 3.33-3.40 (m, 4H), 7.67 (d, 1H, J = 8.8 Hz), 8.17 (dd, 1H, J$_1$ = 2.4 Hz, J$_2$ = 8.8 Hz), 8.52 (t, 1H, J = 5.2 Hz), 8.50-8.54 (bs, 1H), 8.60 (d, 1H, J = 2.4 Hz), 9.18 (bs, 1H), 10.80 (bs, 1H), 13.04 (bs, 1H); m/z [M$^+$ + 1] 341.0. |
| 17 | 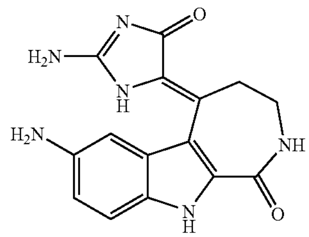 | $^1$H NMR (DMSO-d$_6$) δ 3.30-3.36 (m, 4H), 7.26 (d, 1H, J = 8.0 Hz), 7.44 (s, 1H), 7.56 (d, 1H, J = 8.0 Hz), 8.42 (t, 1H, J = 5.2 Hz), 8.80 (bs, 1H), 10.60 (bs, 2H), 12.59 (bs, 1H); m/z [M$^+$ + 1] 311.1. |
| 18 | 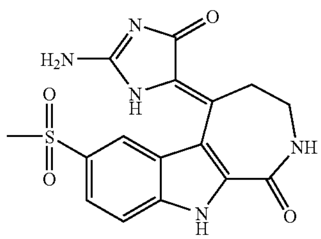 | $^1$H NMR (DMSO-d$_6$) δ 3.20 (s, 2H), 3.34-3.40 (m, 4H), 7.70 (d, 1H, J = 8.8 Hz), 7.81 (dd, 1H, J$_1$ = 2.4 Hz, J$_2$ = 8.8 Hz), 8.19 (d, 1H, J = 2.4 Hz), 8.40 (bs, 1H), 8.48 (t, 1H, J = 5.2 Hz) 9.10 (bs, 1H), 10.70 (bs, 1H), 12.88 (bs, 1H); m/z [M$^+$ + 1] 374.1. |
| 19 | 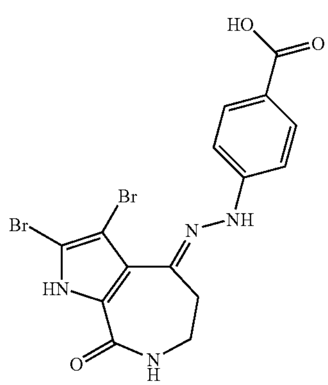 | $^1$H NMR (DMSO-d$_6$) δ 2.80-2.86 (m, 2H), 3.30-3.34 (m, 2H), 7.33 (d, 2H, J = 8.0 Hz), 7.79 (d, 2H, J = 8.0 Hz), 8.10 (t, 1H, J = 5.2 Hz), 9.57 (s, 1H), 12.28 (bs, 1H), 12.89 (s, 1H); m/z [M$^+$ + 1] 456.9. |
| 20 | 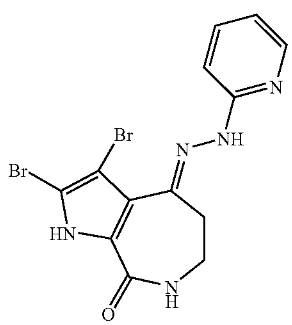 | $^1$H NMR (DMSO-d$_6$) δ 2.92-2.96 (m, 2H), 3.40-3.28 (m, 2H), 7.03 (t, 1H, J = 6.8 Hz), 7.50 (d, 1H, J = 8.7 Hz), 8.00 (t, 1H, J = 8.0 Hz), 8.15, (d, 1H, J = 5.2 Hz), 8.20 (t, 1H, J = 5.4 Hz), 10.91 (bs, 1H), 13.14 (s, 1H); m/z [M$^+$ + 1] 413.9. |

TABLE 1-continued

| Compound | Structure | Physical Data |
|---|---|---|
| 21 | 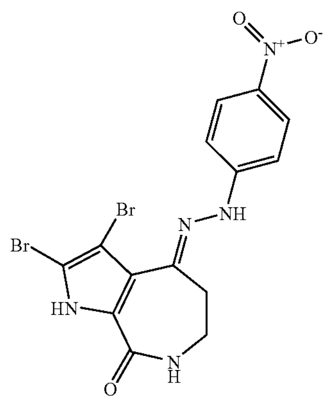 | $^1$H NMR (DMSO-d$_6$) δ 2.84-2.90 (m, 2H), 3.31-3.36 (m, 2H), 7.42 (d, 2H, J = 8.8 Hz), 8.10-8.18 (m, 3H), 10.07 (s, 1H), 12.98 (s, 1H); m/z [M$^+$ + 1] 457.9. |
| 22 | 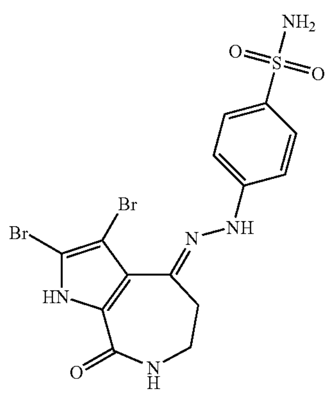 | $^1$H NMR (DMSO-d$_6$) δ 2.80-2.86 (m, 2H), 3.30-3.36 (m, 2H), 7.04 (bs, 2H), 7.37 (d, 2H, J = 8.8 Hz), 7.65 (d, 2H, J = 8.8 Hz), 8.10 (t, 1H, J = 5.6 Hz), 9.57 (s, 1H), 12.90 (s, 1H); m/z [M$^+$ + 1] 491.9. |
| 23 | 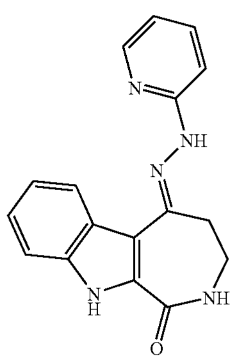 | $^1$H NMR (DMSO-d$_6$) δ 3.06-3.12 (m, 2H), 3.40-3.46 (m, 2H), 7.02 (t, 1H, J = 6.0 Hz), 7.21 (t, 1H, J = 7.2 Hz), 7.31 (t, 1H, J = 7.2 Hz), 7.43 (d, 1H, J = 8.8 Hz), 7.49 (d, 1H, J = 8.0 Hz), 8.02 (t, 1H, J = 7.2 Hz), 8.12 (d, 1H, J = 5.6 Hz), 8.35 (d, 1H, J = 8.0 Hz), 8.46 (t, 1H, J = 4.8 Hz), 10.92 (bs, 1H), 12.07 (s, 1H); m/z [M$^+$ +1] 306.1. |
| 24 | 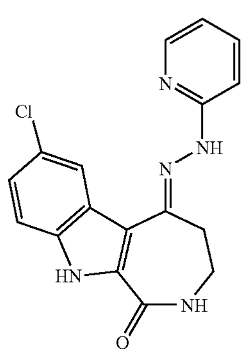 | $^1$H NMR(DMSO-d$_6$) δ 3.06-3.11 (m, 2H), 3.40-3.46 (m, 2H), 7.03 (t, 1H, J = 6.4 Hz), 7.33 (dd, 1H, J$_1$ = 6.1 Hz, J$_2$ = 8.8 Hz), 7.38 (d, 1H, J = 8.8 Hz), 7.50 (d, 1H, J = 8.8 Hz), 8.02 (t, 1H, J = 7.6 Hz), 8.13 (d, 1H, J = 5.2 Hz), 8.33 (d, 1H, J = 1.6 Hz), 8.54 (t, 1H, J = 5.2 Hz), 10.99 (bs, 1H), 12.27 (s, 1H); m/z [M$^+$ + 1] 340.0. |

TABLE 1-continued
| Compound | Structure | Physical Data |
|---|---|---|
| 25 | 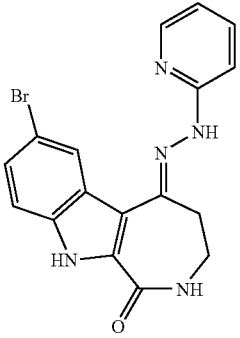 | $^1$H NMR(DMSO-d$_6$) δ 3.04-3.10 (m, 2H), 3.40-3.46 (m, 2H), 7.01 (t, 1H, J = 6.4 Hz), 7.37 (d, 1H, J = 8.8 Hz), 7.45 (s, 2H), 7.99 (t, 1H, J = 7.6 Hz), 8.14 (d, 1H, J = 5.2 Hz), 8.50 (s, 1H), 8.53 (t, 1H, J = 5.2 Hz), 10.84 (bs, 1H), 12.26 (s, 1H); m/z [M$^+$ + 1] 384.0. |
| 26 | 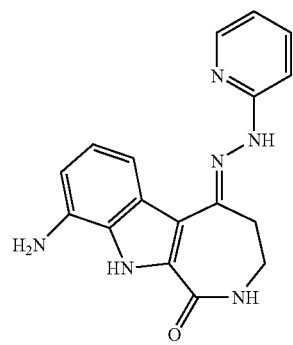 | $^1$H NMR (DMSO-d$_6$) δ 3.04-3.10 (m, 2H), 3.39-3.44 (m, 2H), 6.53 (d, 1H, J = 7.5 Hz), 6.93-7.01 (m, 2H), 7.41 (d, 1H, J = 8.4 Hz), 7.64 (d, 1H, J = 8.0 Hz), 7.98 (t, 1H, J = 8.0 Hz), 8.12 (d, 1H, J = 5.2 Hz), 8.44 (t, 1H, J = 5.2 Hz), 10.75 (bs, 1H), 11.69 (s, 1H); m/z [M$^+$ + 1] 321.1. |
| 27 | 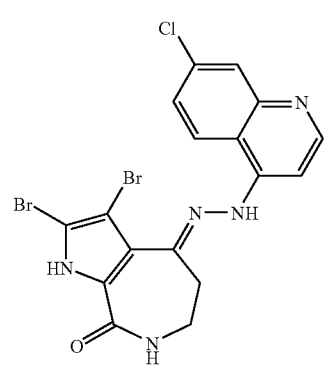 | $^1$H NMR (DMSO-d$_6$) δ 3.28-3.36 (m, 4H), 7.70 (d, 1H, J = 5.2 Hz), 7.84 (d, 1H, J = 5.2 Hz), 7.99 (s, 1H), 8.38 (t, 1H, J = 5.2 Hz), 8.64-8.76 (m, 2H), 11.20 (bs, 1H), 13.30 (s, 1H); m/z [M$^+$ + 1] 497.9. |
| 28 | 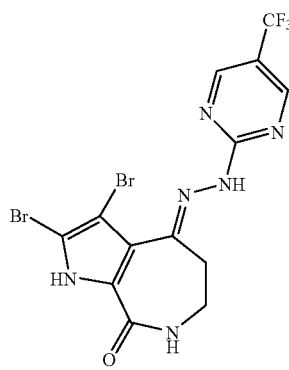 | $^1$H NMR (DMSO-d$_6$) δ 2.91-2.98 (m, 2H), 3.32-3.25 (m, 2H), 7.26 (d, 1H, J = 4.8 Hz), 8.14 (t, 1H, J = 4.8 Hz), 8.79 (d, 1H, J = 4.8 Hz), 10.53 (s, 1H), 12.99 (s, 1H); m/z [M$^+$ + 1] 482.9. |

TABLE 1-continued

| Compound | Structure | Physical Data |
|---|---|---|
| 29 | 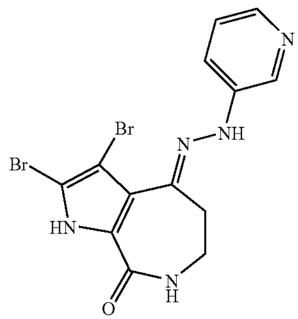 | $^1$H NMR (DMSO-d$_6$) δ 2.84-2.88 (m, 2H), 3.32-3.40 (m, 2H), 8.84 (dd, 1H, J$_1$ = 5.6 Hz, J$_2$ = 8.4 Hz), 8.18-8.23 (m, 2H), 8.27 (d, 1H, J = 4.8 Hz), 8.60 (s, 1H), 13.05 (s, 1H); m/z [M$^+$ + 1] 413.9. |
| 30 | 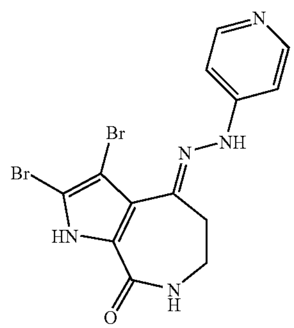 | $^1$H NMR (DMSO-d$_6$) δ 2.93-2.99 (m, 2H), 3.32-3.35 (m, 2H), 7.26-7.44 (m, 1H), 7.65-7.82 (m, 1H), 8.27 (t, 1H, J = 5.6 Hz), 8.32-8.44 (m, 2H), 11.10 (s, 1H), 13.19 (s, 1H), 13.76 (s, 1H); m/z [M$^+$ + 1] 413.9. |
| 31 | 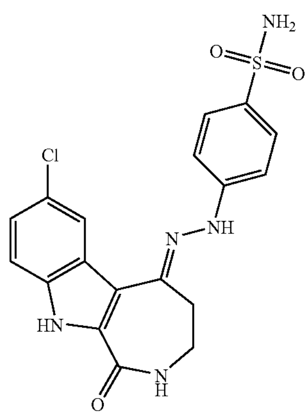 | $^1$H NMR (DMSO-d$_6$) δ 2.95-3.02 (m, 2H), 3.40-3.46 (m, 2H), 7.07 (s, 2H), 7.29 (d, 2H, J = 8.7 Hz), 7.31 (d, 1H, J = 1.6 Hz), 7.48 (d, 1H, J = 8.7 Hz), 7.71 (d, 2H, J = 8.7 Hz), 8.41 (t, 1H, J = 5.3 Hz), 8.45 (d, 1H, J = 1.6 Hz), 9.68 (s, 1H), 11.99 (s, 1H); m/z [M$^+$ + 1] 418.0. |
| 32 | 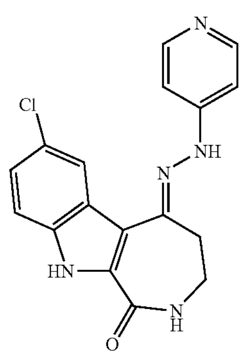 | $^1$H NMR (DMSO-d$_6$) δ 3.07-3.12 (m, 2H), 3.42-3.48 (m, 2H), 7.36 (dd, 1H, J$_1$ = 2.4 Hz, J$_2$ = 8.8 Hz), 7.39 (d, 1H, J = 5.6 Hz), 7.53 (d, 1H, J = 8.8 Hz), 8.32 (d, 1H, J = 1.6 Hz), 8.44 (bs, 1H), 8.57 (t, 1H, J = 5.2 Hz), 11.15 (s, 1H), 12.33 (s, 1H), 13.72 (s, 1H); m/z [M$^+$ + 1] 340.1. |

TABLE 1-continued

| Compound | Structure | Physical Data |
|---|---|---|
| 33 | 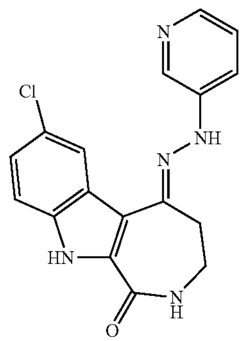 | $^1$H NMR (DMSO-d$_6$) δ 2.98-3.04 (m, 2H), 3.40-3.44 (m, 2H), 7.32 (dd, 1H, J$_1$ = 1.6 Hz, J$_2$ = 8.8 Hz), 7.50 (d, 1H, J = 8.8 Hz), 7.55 (dd, 1H, J$_1$ = 5.2 Hz, J$_2$ = 8.8 Hz), 7.98 (d, 1H, J = 8.0 Hz), 8.22 (d, 1H, J = 5.2 Hz), 8.35 (d, 1H, J = 1.6 Hz), 8.46 (t, 1H, J = 5.2 Hz), 8.51 (d, 2H, J = 2.0 Hz), 9.97 (s, 1H), 12.10 (s, 1H); m/z [M$^+$ + 1] 340.1. |
| 34 | 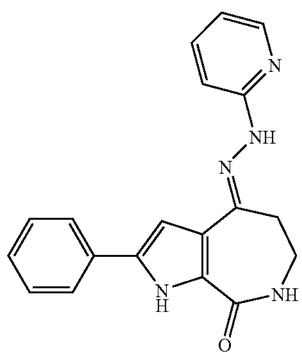 | $^1$H NMR (DMSO-d$_6$) δ 2.90-2.96 (m, 2H), 3.35-3.39 (m, 2H), 7.08 (t, 1H, J = 6.8 Hz), 7.30 (t, 1H, J = 7.2 Hz), 7.40-7.46 (m, 4H), 7.91 (d, 2H, J = 8.0 Hz), 8.06 (t, 1H, J = 8.0 Hz), 8.11 (t, 1H, J = 5.2 Hz), 8.14 (d, 2H, J = 6.0 Hz), 11.32 (bs, 1H), 12.05 (s, 1H); m/z [M$^+$ + 1] 332.1. |
| 35 | 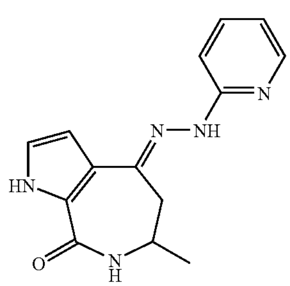 | $^1$H NMR (DMSO-d$_6$) δ 1.29 (d, 3H, J = 6.4 Hz), 2.67 (dd, 1H, J$_1$ = 10.4 Hz, J$_2$ = 17.6 Hz), 3.09 (d, 1H, J = 17.6 Hz), 3.70-3.80 (m, 1H), 7.01 (t, 1H, J = 2.4 Hz), 7.07 (t, 2H, J = 6.8 Hz), 7.38 (d, 1H, J = 8.8 Hz), 7.88 (s, 1H), 8.02-8.12 (m, 2H), 11.39 (bs, 1H), 11.79 (s, 1H); m/z [M$^+$ + 1] 270.1. |
| 36 | 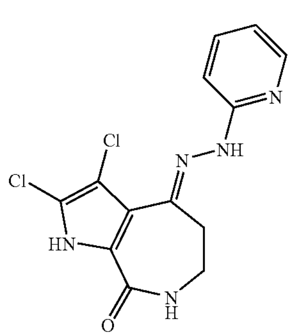 | $^1$H NMR (DMSO-d$_6$) δ 2.90-2.96 (m, 2H), 3.32-3.10 (m, 2H), 7.01 (t, 1H, J = 6.8 Hz), 7.45 (d, 1H, J = 8.8 Hz), 7.97 (t, 1H, J = 7.2 Hz), 8.14 (d, 1H, J = 6.0 Hz), 8.21 (t, 1H, J = 5.2 Hz), 10.82 (bs, 1H), 13.14 (s, 1H); m/z [M$^+$ + 1] 324.0. |

TABLE 1-continued

| Compound | Structure | Physical Data |
|---|---|---|
| 37 | 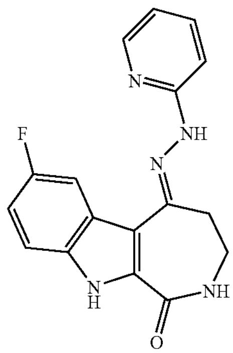 | $^1$H NMR (DMSO-d$_6$) δ 3.104-3.13 (m, 2H), 3.40-3.48 (m, 2H), 7.03 (t, 1H, J = 6.4 Hz), 7.19 (dt, 1H, J$_1$ = 2.8 Hz, J$_2$ = 8.8 Hz)), 7.40 (d, 1H, J = 8.8 Hz), 7.50 (dd, 1H, J$_1$ = 5.2 Hz, J$_2$ = 8.8 Hz)), 8.00-8.06 (m, 2H), 8.13 (d, 1H, J = 6.0 Hz), 8.50 (t, 1H, J = 6.0 Hz), 11.00 (bs, 1H), 12.19 (s, 1H); m/z [M$^+$ + 1] 324.1. |
| 38 | 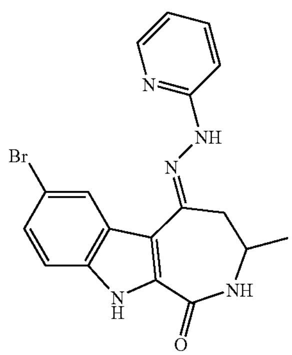 | $^1$H NMR (DMSO-d$_6$) δ 1.32 (d, 3H, J = 6.4 Hz), 2.84 (dd, 1H, J$_1$ = 10.0 Hz, J$_2$ = 17.6 Hz), 3.24 (d, 1H, J =17.6 Hz), 3.80-3.86 (m, 1H), 7.01 (t, 1H, J = 6.8 Hz), 7.36 (d, 1H, J = 8.0 Hz), 7.40-7.48 (m, 2H), 7.99 (t, 1H, J = 7.2 Hz), 8.13 (d, 1H, J = 5.8 Hz), 8.37 (d, 1H, J = 3.6 Hz), 8.49 (s, 1H), 10.84 (bs, 1H), 12.22 (s, 1H); m/z [M$^+$ + 1] 398.0. |
| 39 | 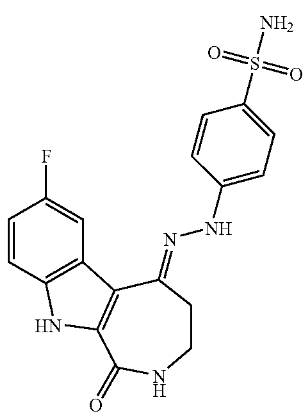 | $^1$H NMR (DMSO-d$_6$) δ 2.90-3.02 (m, 2H), 3.41-3.43 (m, 2H), 7.05 (s, 1H), 7.17 (t, 1H, J = 8.0 Hz), 7.28 (d, 2H, J = 8.4 Hz), 7.44-7.50 (m, 1H), 7.71 (d, 2H, J = 8.4 Hz), 8.09 (t, 1H, J = 8.8 Hz), 8.39 (s, 1H), 9.62 (s, 1H), 11.90 (s, 1H); m/z [M$^+$ + 1] 402.1. |
| 40 | 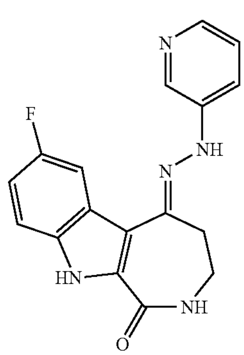 | $^1$H NMR (DMSO-d$_6$) δ 2.98-3.02 (m, 2H), 3.42-3.47 (m, 2H), 7.19 (t, 1H, J = 2.6 Hz), 7.49 (dd, 1H, J$_1$ = 4.8 Hz, J$_2$ = 8.9 Hz), 7.82 (dd, 1H, J$_1$ = 5.3 Hz, J$_2$ = 8.6 Hz), 8.01 (d, 1H, J = 2.5 Hz), 8.04 (dd, 1H, J$_1$ = 2.5 Hz, J$_2$ = 6.9 Hz), 8.24 (d, 1H, J = 5.1 Hz), 8.45 (t, 1H, J = 5.6 Hz), 8.53 (d, 1H, J = 2.5 Hz), 10.03 (s, 1H), 12.04 (s, 1H); m/z [M$^+$+ 1] 324.1. |

TABLE 1-continued

| Compound | Structure | Physical Data |
|---|---|---|
| 41 | 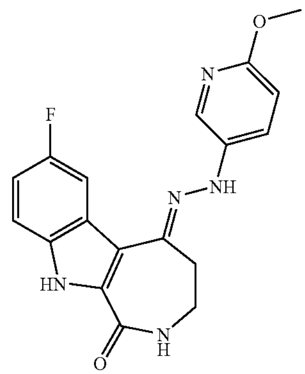 | $^1$H NMR (DMSO-d$_6$) δ 2.89-2.96 (m, 2H), 3.38-3.45 (m, 2H), 6.82 (d, 1H, J = 8.8 Hz), 7.16 (dt, 1H, J$_1$ = 2.4 Hz, J$_1$ = 9.2 Hz), 7.46 (dd, 1H, J = 4.8 Hz, J$_2$ = 8.8 Hz), 7.58 (dd, 1H, J$_1$ = 2.8 Hz, J$_2$ = 8.8 Hz), 8.07 (dd, 1H, J$_1$ = 2.0 Hz, J$_2$ = 10.4 Hz), 8.10 (d, 1H, J = 2.8 Hz), 8.37 (t, 1H, J = 5.6 Hz), 9.04 (s, 1H), 11.84 (s, 1H); m/z [M$^+$ + 1] 354.1. |
| 42 | 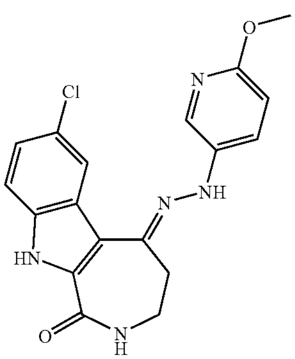 | $^1$H NMR (DMSO-d$_6$) δ 2.90-2.97 (m, 2H), 3.37-3.47 (m, 2H), 6.80 (d, 1H, J = 8.8 Hz), 7.29 (d, 1H, J = 8.8 Hz), 7.46 (d, 1H, J = 8.8 Hz), 7.57 (dd, 1H, J$_1$ = 2.8 Hz, J$_2$ = 8.8 Hz), 8.09 (s, 1H), 8.39 (t, 1H, J = 5.6 Hz), 8.40 (s, 1H), 9.07 (s, 1H), 11.92 (s, 1H); m/z [M$^+$ + 1] 370.0. |
| 43 | 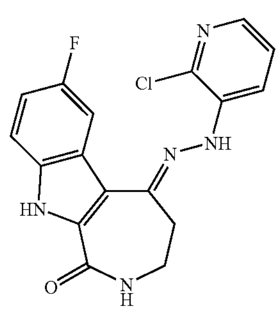 | $^1$H NMR (DMSO-d$_6$) δ 3.08-3.14 (m, 2H), 3.40-3.47 (m, 2H), 7.24-7.16 (m, 1H), 7.44-7.52 (m, 2H), 7.83 (d, 1H, J = 8.0 Hz), 7.89 (d, 1H, J = 4.0 Hz), 8.05 (dd, 1H, J$_1$ = 2.4 Hz, J$_2$ = 10.8 Hz), 8.26 (s, 1H), 8.47 (t, 1H, J = 4.8 Hz), 12.02 (s, 1H); m/z [M$^+$ + 1] 358.0. |
| 44 | 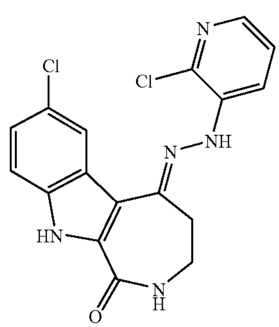 | $^1$H NMR (DMSO-d$_6$) δ 3.06-3.16 (m, 2H), 3.40-3.46 (m, 2H), 7.32 (dd, 1H, J$_1$ = 2.0 Hz, J$_2$ = 8.8 Hz), 7.46 (dd, 1H, J$_1$ = 4.8 Hz, J$_2$ = 8.4 Hz), 7.50 (d, 1H, J = 8.4 Hz), 7.80 (dd, 1H, J$_1$ = 1.2 Hz, J$_2$ = 6.4 Hz), 7.90 (dd, 1H, J$_1$ = 1.2 Hz, J$_2$ = 4.4 Hz), 8.30 (s, 1H), 8.39 (d, 1H, J = 2 Hz), 8.49 (t, 1H, J = 5.6 Hz), 12.10 (s, 1H); m/z [M$^+$ + 1] 374.0. |

TABLE 1-continued

| Compound | Structure | Physical Data |
|---|---|---|
| 45 | 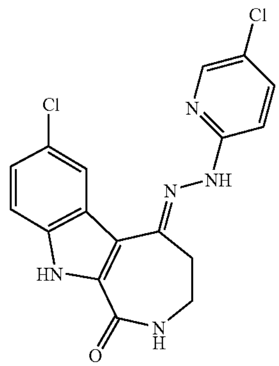 | $^1$H NMR (DMSO-d$_6$) δ 3.29-3.34 (m, 2H), 3.36-3.44 (m, 2H), 7.19 (d, 1H, J = 8.8 Hz), 7.30 (dd, 1H, J$_1$ = 2.4 Hz, J$_2$ = 8.8 Hz), 7.48 (d, 1H, J = 8.0 Hz), 7.83 (dd, 1H, J$_1$ = 2.4 Hz, J$_2$ = 8.8 Hz), 8.20 (d, 1H, J = 2.4 Hz), 8.42 (t, 1H, J = 5.6 Hz), 8.43 (s, 1H), 9.89 (s, 1H), 12.00 (s, 1H); m/z [M$^+$ + 1] 374.0. |
| 46 | 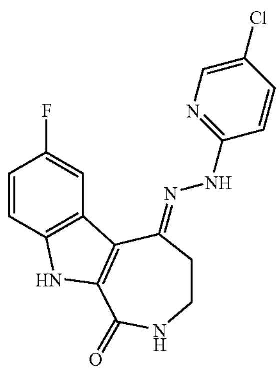 | $^1$H NMR (DMSO-d$_6$) δ 2.98-3.03 (m, 2H), 3.36-3.42 (m, 2H), 7.17 (dt, 1H, J$_1$ = 2.4 Hz, J$_2$ = 9.2 Hz), 7.21 (d, 1H, J = 8.8 Hz), 7.48 (dd, 1H, J$_1$ = 4.8 Hz, J$_2$ = 9.2 Hz), 7.84 (dd, 1H, J$_1$ = 2.8 Hz, J$_2$ = 8.8 Hz), 8.09 (dd, 1H, J$_1$ = 2.0 Hz, J$_2$ = 10.4 Hz), 8.20 (d, 1H, J = 2.0 Hz), 8.40 (t, 1H, J = 5.6 Hz), 9.85 (s, 1H), 11.92 (s, 1H); m/z [M$^+$ + 1] 358.1. |
| 47 | 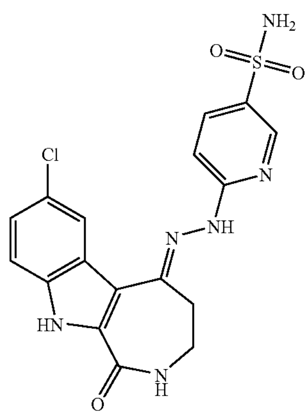 | $^1$H NMR (DMSO-d$_6$) δ 3.02-3.07 (m, 2H), 3.40-3.44 (m, 2H), 7.25 (d, 1H, J = 8.8 Hz), 7.27 (s, 1H), 7.31 (dd, 1H, J$_1$ = 2.0 Hz, J$_2$ = 9.2 Hz), 7.49 (d, 1H, J = 8.8 Hz), 8.06 (dd, 1H, J$_1$ = 2.0 Hz, J$_2$ = 9.2 Hz), 8.44 (t, 1H, J = 5.6 Hz), 8.48 (s, 1H), 8.56 (d, 1H, J = 2.0 Hz), 10.34 (s, 1H), 12.06 (s, 1H); m/z [M$^+$ + 1] 419.1. |
| 48 | 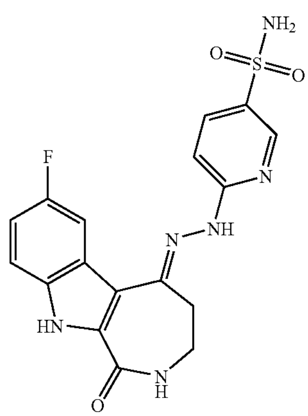 | $^1$H NMR (DMSO-d$_6$) δ 3.02-3.07 (m, 2H), 3.41-3.44 (m, 2H), 7.17 (dt, 1H, J$_1$ = 2.8 Hz, J$_2$ = 9.2 Hz), 7.25-7.30 (m, 3H), 7.49 (dd, 1H, J$_1$ = 4.8 Hz, J$_2$ = 8.8 Hz), 8.07 (dd, 1H, J$_1$ = 2.0 Hz, J$_2$ = 8.8 Hz), 8.13 (dd, 1H, J$_1$ = 2.0 Hz, J$_2$ = 10.4 Hz), 8.42 (t, 1H, J = 5.6 Hz), 8.56 (d, 1H, J = 2.4 Hz), 10.27 (s, 1H), 11.89 (s, 1H); m/z [M$^+$ + 1] 403.1. |

TABLE 1-continued

| Compound | Structure | Physical Data |
|---|---|---|
| 49 | 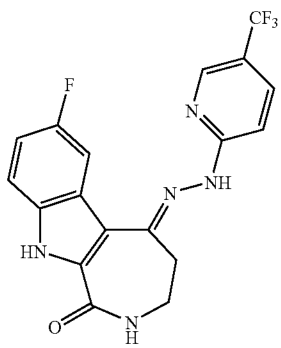 | $^1$H NMR (DMSO-d$_6$) δ 3.02-3.08 (m, 2H), 3.37-3.42 (m, 2H), 7.18 (dt, 1H, J$_1$ = 2.8 Hz, J$_2$ = 8.8 Hz), 7.30 (d, 1H, J = 8.8 Hz), 7.49 (dd, 1H, J$_1$ = 4.8 Hz, J$_2$ = 8.8 Hz), 8.06-8.13 (2H, m), 8.44 (t, 1H, J = 5.6 Hz), 8.52 (s, 1H), 10.27 (s, 1H), 12.00 (s, 1H); m/z [M$^+$ + 1] 392.1. |
| 50 | 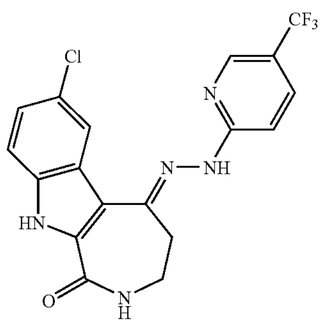 | $^1$H NMR (DMSO-d$_6$) δ 3.02-3.08 (m, 2H), 3.36-3.42 (m, 2H), 7.28 (d, 1H, J = 9.0 Hz), 7.31 (dd, 1H, J$_1$ = 2.0 Hz, J$_2$ = 9.0 Hz), 7.49 (d, 1H, J = 8.0 Hz), 8.07 (dd, 1H, J$_1$ = 2.8 Hz, J$_2$ = 9.0 Hz), 8.44-8.49 (m, 2H), 8.53 (s, 1H), 10.35 (s, 1H), 12.08 (s, 1H); m/z [M$^+$ + 1] 408.1. |
| 51 | 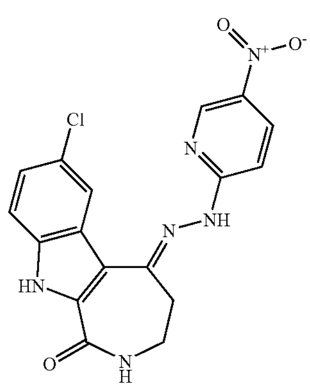 | $^1$H NMR (DMSO-d$_6$) δ 3.06-3.11 (m, 2H), 3.38-3.42 (m, 2H), 7.22 (d, 1H, J = 9.6 Hz), 7.33 (dd, 1H, J$_1$ = 2.0 Hz, J$_2$ = 8.8 Hz), 7.50 (d, 1H, J = 8.4 Hz), 8.43-8.53 (m, 3H), 9.07 (d, 1H, J = 2.8 Hz), 10.91 (s, 1H), 12.17 (s, 1H); m/z [M$^+$ + 1] 385.0. |
| 52 | 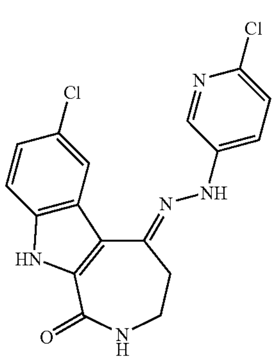 | $^1$H NMR (DMSO-d$_6$) δ 2.93-2.98 (m, 2H), 3.42-3.44 (m, 2H), 7.31 (dd, 1H, J$_1$ = 2.0 Hz, J$_2$ = 8.8 Hz), 7.39 (d, 1H, J = 8.8 Hz), 7.48 (d, 1H, J = 8.8 Hz), 7.57 (dd, 1H, J$_1$ = 3.2 Hz, J$_2$ = 8.8 Hz), 8.31 (d, 1H, J = 2.8 Hz), 8.36 (d, 1H, J = 1.6 Hz), 8.41 (t, 1H, J = 5.6 Hz), 9.52 (s, 1H), 12.00 (s, 1H); m/z [M$^+$ + 1] 374.0. |

TABLE 1-continued

| Compound | Structure | Physical Data |
|---|---|---|
| 53 | 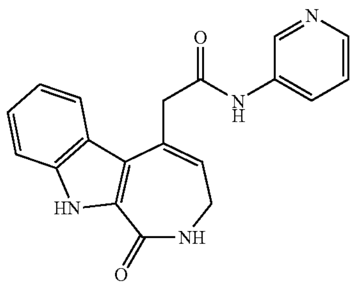 | $^1$H NMR (DMSO-d$_6$) δ 3.43 (t, 2H, J = 6.0 Hz), 3.91 (s, 2H), 5.97 (t, 1H, J = 7.6 Hz), 7.08 (t, 1H, J = 8.0 Hz), 7.24 (t, 2H, J = 7.2 Hz), 7.47(d, 1H, J = 8.0 Hz), 7.57 (dd, 1H, J$_1$ = 5.2 Hz, J$_2$ = 8.0 Hz), 7.90 (d, 1H, J = 8.0 Hz), 8.12-8.17 (m, 2H), 8.36 (d, 1H, J = 5.2 Hz), 8.88 (s, 1H), 10.62 (s, 1H), 11.92 (s, 1H); m/z [M$^+$ + 1] 333.1. |
| 54 | 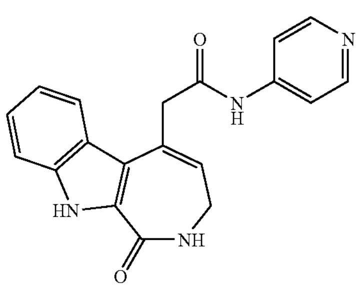 | $^1$H NMR (DMSO-d$_6$) δ 3.44 (t, 2H, J = 6.0 Hz), 4.02 (s, 2H), 5.97 (t, 1H, J = 7.2 Hz), 7.07 (t, 1H, J = 7.2 Hz), 7.24 (t, 2H, J = 7.2 Hz), 7.47(d, 1H, J = 8.0 Hz),7.84 (d, 1H, J = 8.0 Hz), 7.93 (d, 2H, J = 6.4 Hz), 8.16 (t, 1H, J = 5.2 Hz), 8.62 (d, 2H, J = 6.4 Hz), 11.40 (s, 1H), 11.95 (s, 1H); m/z [M$^+$ + 1] 333.1. |
| 55 | 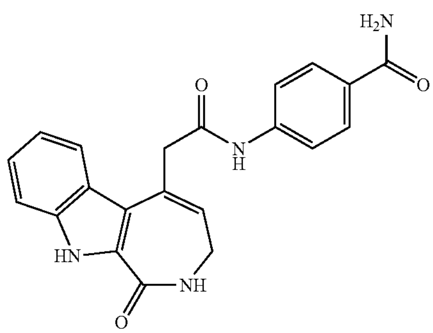 | $^1$H NMR (DMSO-d$_6$) δ 3.43 (t, 2H, J = 6.8 Hz), 3.87 (s, 2H), 5.97 (t, 1H, J = 7.6 Hz), 7.08 (t, 1H, J = 6.4 Hz), 7.16-7.21 (bs, 1H), 7.24 (t, 1H, J = 7.2 Hz), 7.47 (d, 1H, J = 8.8 Hz), 7.59 (d, 2H, J = 8.8 Hz), 7.79 (d, 2H, J = 8.8 Hz), 7.80-7.83 (m, 1H), 7.91 (d, 1H, J = 8.0 Hz), 8.13 (t, 1H, J = 5.2 Hz), 10.29 (s, 1H), 11.91 (s, 1H); m/z [M$^+$ + 1] 375.1. |
| 56 | 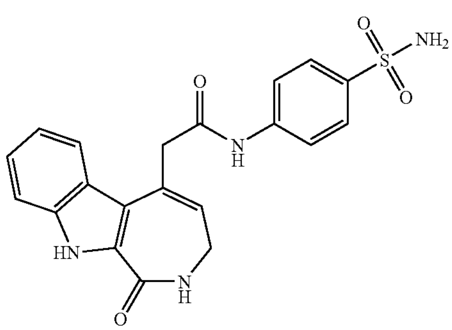 | $^1$H NMR (DMSO-d$_6$) δ 3.43 (t, 2H, J = 6.0 Hz), 3.88 (s, 2H), 5.97 (t, 1H, J = 6.8 Hz), 7.08 (t, 1H, J = 7.2 Hz), 7.19-7.26 (m, 3H), 7.47 (d, 1H, J = 8.0 Hz), 7.67-7.74 (m, 4H), 7.90 (d, 1H, J = 8.0 Hz), 8.13 (t, 1H, J = 4.8 Hz), 10.43 (s, 1H), 11.91 (s, 1H); m/z [M$^+$ + 1] 411.0. |
| 57 | 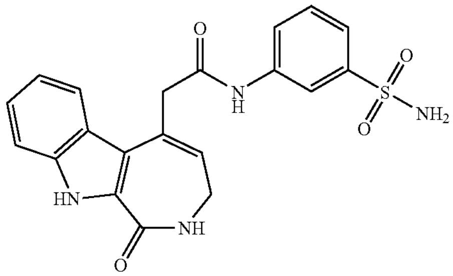 | $^1$H NMR (DMSO-d$_6$) δ 3.43 (t, 2H, J = 6.8 Hz), 3.87 (s, 2H), (m, 2H), 5.96 (t, 1H, J = 7.2 Hz), 7.08 (t, 1H, J = 6.4 Hz), 7.24 (t, 1H, J = 7.2 Hz), 7.31 (s, 2H), 7.45-7.49 (m, 3H), 7.66-7.72 (m, 1H), 7.92 (d, 1H, J = 8.0 Hz), 8.12-8.16 (m, 2H), 10.40 (s, 1H), 11.91 (s, 1H); m/z [M$^+$ + 1] 411.0. |

TABLE 1-continued

| Compound | Structure | Physical Data |
| --- | --- | --- |
| 58 | 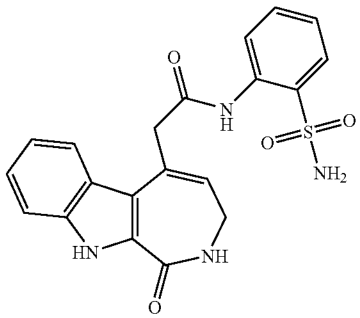 | $^1$H NMR (DMSO-d$_6$) δ 3.47 (t, 2H, J = 6.0 Hz), 3.89 (s, 2H), 6.09 (t, 1H, J = 7.6 Hz), 7.09 (t, 1H, J = 7.6 Hz), 7.25 (t, 2H, J = 7.6 Hz), 7.46-7.59 (m, 4H), 7.79-7.84 (m, 2H), 8.11-8.16 (m, 2H), 9.61 (s, 1H), 11.95 (s, 1H); m/z [M$^+$ + 1] 411.0. |
| 59 | 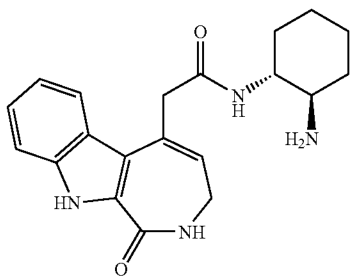 | $^1$H NMR (DMSO-d$_6$) δ 1.14-1.38 (m, 4H), 1.58-1.70 (m, 2H), 1.90-1.98 (m, 1H), 2.78-2.88 (m, 1H), 3.43 (t, 2H, J = 6.0 Hz), 3.54-3.72 (m, 4H), 5.89 (t, 1H, J = 6.4 Hz), 7.08 (t, 1H, J = 8.0 Hz), 7.25 (t, 2H, J = 7.2 Hz), 7.77 (bs, 3H), 7.86 (d, 1H, J = 8.0 Hz), 7.99 (d, 1H, J = 8.8 Hz), 8.13 (t, 1H, J = 4.8 Hz), 11.89 (s, 1H); m/z [M$^+$ + 1] 353.2. |
| 60 | 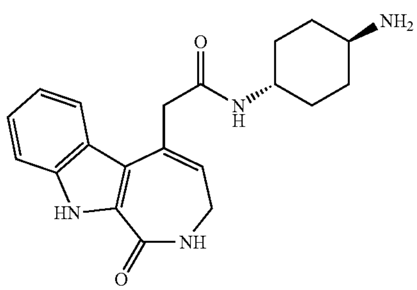 | $^1$H NMR (DMSO-d$_6$) δ 1.10-1.38 (m, 4H), 1.69-1.77 (m, 2H), 1.84-1.92 (m, 2H), 2.90-3.00 (m, 1H), 3.36 (t, 2H, J = 6.0 Hz), 3.38-3.42 (m, 1H), 3.55 (s, 2H), 5.85 (t, 1H, J = 6.4 Hz), 7.06 (t, 1H, J = 7.2 Hz), 7.24 (t, 1H, J = 8.0 Hz), 7.45 (d, 1H, J = 8.0 Hz), 7.76 (bs, 3H), 7.86 (d, 1H, J = 8.0 Hz), 8.11 (t, 1H, J = 5.2 Hz), 11.86 (s, 1H); m/z [M$^+$ + 1] 353.2. |
| 61 | 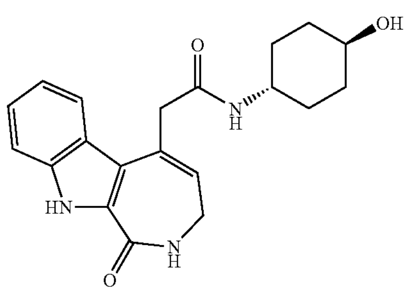 | $^1$H NMR (DMSO-d$_6$) δ 1.08-1.18 (m, 4H), 1.60-1.68 (m, 2H), 1.72-1.80 (m, 2H), 3.36-3.42 (m, 4H), 3.53 (s, 2H), 5.85 (t, 1H, J = 7.6 Hz), 7.06 (t, 1H, J = 7.2 Hz), 7.24 (t, 1H, J = 8.0 Hz), 7.73 (d, 1H, J = 8.4 Hz), 7.86 (d, 1H, J = 8.4 Hz), 8.10 (t, 1H, J = 5.2 Hz), 11.86 (s,1H); m/z [M$^+$ + 1] 354.1. |
| 62 | 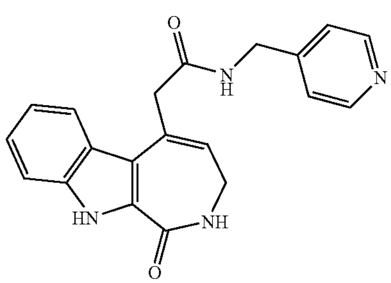 | $^1$H NMR (DMSO-d$_6$) δ 3.43 (t, 2H, J = 6.0 Hz), 3.73 (s, 2H), 4.38 (d, 2H, J = 5.6 Hz), 5.95 (t, 1H, J = 7.2 Hz), 7.07 (t, 1H, J = 8.0 Hz), 7.26 (t, 1H, J = 8.0 Hz), 7.38 (d, 2H, J = 6.0 Hz), 7.48 (d, 1H, J = 8.0 Hz), 7.88 (d, 1H, J = 8.0 Hz), 8.16 (t, 1H, J = 5.2 Hz), 8.57 (d, 2H, J = 6.0 Hz), 8.59 (t, 1H, J = 6.0 Hz), 11.91 (s, 1H); m/z [M$^+$ + 1] 347.1. |

TABLE 1-continued

| Compound | Structure | Physical Data |
|---|---|---|
| 63 | 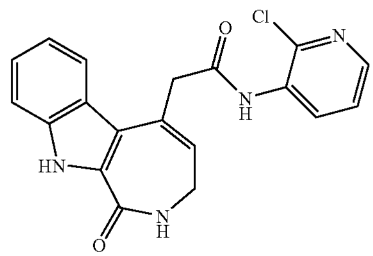 | $^1$H NMR (DMSO-d$_6$) δ 3.44 (t, 2H, J = 6.4 Hz), 3.99 (s, 2H), 6.02 (t, 1H, J = 6.4 Hz), 7.09 (t, 1H, J = 8.8 Hz), 7.25 (t, 1H, J = 7.2 Hz), 7.37 (dd, 1H, J$_1$ = 3.6 Hz, J$_2$ = 8.8 Hz), 7.47 (d, 1H, J = 8.8 Hz), 7.95 (d, 1H, J = 8.0 Hz), 8.08-8.18 (m, 3H), 9.58 (s, 1H), 11.93 (s, 1H); m/z [M$^+$ + 1] 367.0. |
| 64 | 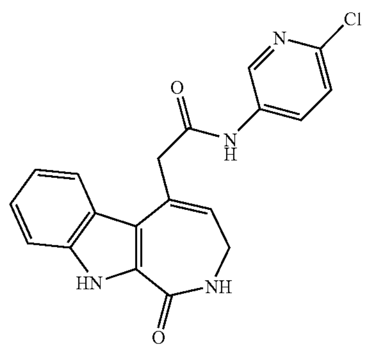 | $^1$H NMR (DMSO-d$_6$) δ 3.43 (t, 2H, J = 6.0 Hz), 3.84 (s, 2H), 5.95 (t, 1H, J = 7.6 Hz), 7.08 (t, 1H, J = 7.6 Hz), 7.24 (t, 1H, J = 6.4 Hz), 7.42 (d, 1H, J = 8.4 Hz), 7.47 (d, 1H, J = 8.8 Hz), 7.88 (d, 1H, J = 8.0 Hz), 8.01 (dd, 1H, J$_1$ = 2.0 Hz, J$_2$ = 8.8 Hz), 8.14 (t, 1H, J = 2.8 Hz), 8.54 (d, 1H, J = 2.8 Hz), 10.47 (s, 1H), 11.92 (s, 1H); m/z [M$^+$ + 1] 367.0. |
| 65 | 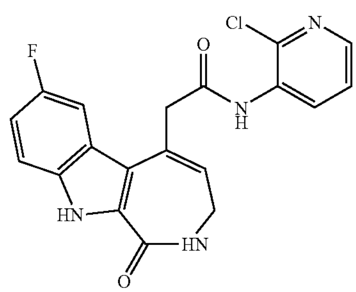 | $^1$H NMR (DMSO-d$_6$) δ 3.44 (t, 2H, J = 6.4 Hz), 3.96 (s, 2H), 6.01 (t, 1H, J = 6.4 Hz), 7.12 (dt, 1H, J$_1$ = 2.0 Hz, J$_2$ = 9.6 Hz), 7.37 (dd, 1H, J$_1$ = 4.2 Hz, J$_2$ = 8.0 Hz), 7.46 (dd, 1H, J$_1$ = 4.4 Hz, J$_2$ = 9.6 Hz), 7.75 (dd, 1H, J$_1$ = 2.4 Hz, J$_2$ = 10.0 Hz), 8.08 (dd, 1H, J$_1$ = 1.6 Hz, J$_2$ = 8.0 Hz), 8.14 (dd, 1H, J$_1$ = 2.0 Hz, J$_2$ = 4.4 Hz), 8.21 (t, 1H, J = 5.6 Hz), 9.63 (s, 1H), 12.04 (s, 1H); m/z [M$^+$ + 1] 385.0. |
| 66 | 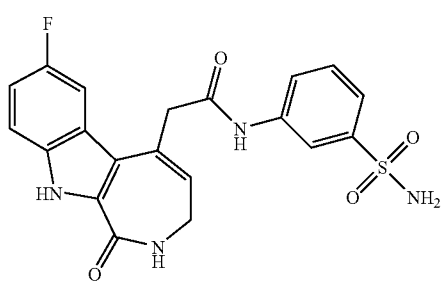 | $^1$H NMR (DMSO-d$_6$) δ 3.43 (t, 2H, J = 6.4 Hz), 3.83 (s, 2H), 5.97 (t, 1H, J = 6.4 Hz), 7.12 (dt, 1H, J$_1$ = 2.4 Hz, J$_2$ = 8.8 Hz), 7.30 (s, 2H), 7.44-7.50 (m, 3H), 7.66-7.74 (m, 2H), 8.14 (s, 1H), 8.19 (t, 1H, J = 5.6 Hz), 10.41 (s, 1H), 12.03 (s, 1H); m/z [M$^+$ + 1] 429.0. |
| 67 | 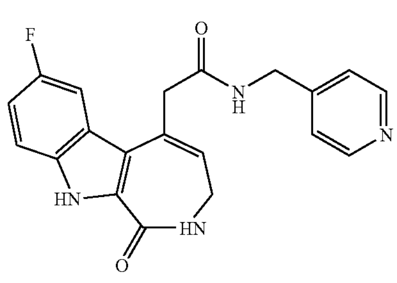 | $^1$H NMR (DMSO-d$_6$) δ 3.42 (t, 2H, J = 6.4 Hz), 3.69 (s, 2H), 4.39 (d, 2H, J = 5.6 Hz), 5.96 (t, 1H, J = 6.4 Hz), 7.13 (dt, 1H, J$_1$ = 2.4 Hz, J$_2$ = 8.8 Hz), 7.41 (d, 2H, J = 6.8 Hz), 7.47 (dd, 1H, J$_1$ = 5.2 Hz, J$_2$ = 8.8 Hz), 7.66 (dd, 1H, J$_1$ = 2.0 Hz, J$_2$ = 10.8 Hz), 8.21 (t, 1H, J = 6.0 Hz), 8.58 (d, 2H, J = 6.8 Hz), 8.63 (t, 1H, J = 5.6 Hz), 12.03 (s, 1H); m/z [M$^+$ + 1] 365.1. |

TABLE 1-continued

| Compound | Structure | Physical Data |
|---|---|---|
| 68 | 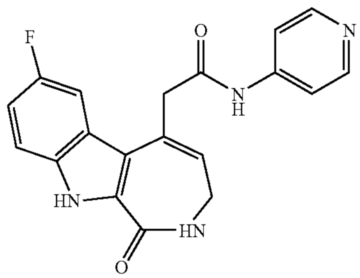 | $^1$H NMR (DMSO-d$_6$) δ 3.44 (t, 2H, J = 6.0 Hz), 3.99 (s, 2H), 5.97 (t, 1H, J = 6.0 Hz), 7.12 (dt, 1H, J$_1$ = 2.4 Hz, J$_2$ = 9.6 Hz), 7.47 (dd, 1H, J$_1$ = 5.2 Hz, J$_2$ = 8.4 Hz), 7.63 (dd, 1H, J$_1$ = 2.4 Hz, J$_2$ = 11.2 Hz), 7.93 (d, 2H, J = 6.8 Hz), 8.22 (t, 1H, J = 4.4 Hz), 8.62 (d, 2H, J = 6.8 Hz), 11.38 (s, 1H), 12.07 (s, 1H); m/z [M$^+$ + 1] 351.1. |
| 69 | 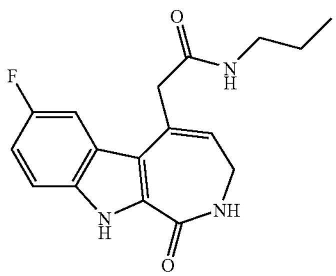 | $^1$H NMR (DMSO-d$_6$) δ 0.77 (t, 3H, J = 8.0 Hz), 1.34 (sextet, 2H, J = 7.6 Hz), 2.97 (q, 2H, J = 6.0 Hz), 3.39 (t, 2H, J = 6.0 Hz), 3.52 (s, 2H), 5.88 (t, 1H, J = 7.2 Hz), 7.11 (dt, 1H, J$_1$ = 6.0 Hz, J$_2$ = 8.8 Hz), 7.45 (dd, 1H, J$_1$ = 4.8 Hz, J$_2$ = 9.2 Hz), 7.66 (dd, 1H, J$_1$ = 2.8 Hz, J$_2$ = 10.8 Hz), 7.91 (t, 1H, J = 6.0 Hz), 8.16 (t, 1H, J = 5.2 Hz), 11.97 (s, 1H); m/z [M$^+$ + 1] 316.1. |
| 70 | 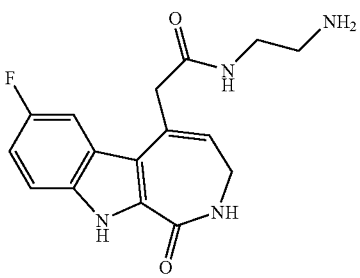 | $^1$H NMR (DMSO-d$_6$) δ 2.76-2.82 (m, 2H), 3.25 (q, 2H, J = 6.0 Hz), 3.41 (t, 2H, J = 6.8 Hz), 3.56 (s, 2H), 5.90 (t, 1H, J = 7.2 Hz), 7.13 (dt, 1H, J$_1$ = 2.4 Hz, J$_2$ = 8.8 Hz), 7.46 (dd, 1H, J$_1$ = 5.2 Hz, J$_2$ = 8.8 Hz), 7.62 (dd, 1H, J$_1$ = 2.4 Hz, J$_2$ = 11.2 Hz), 7.66-7.72 (bs, 3H), 8.16 (t, 1H, J = 5.2 Hz), 8.19 (t, 1H, J = 5.2 Hz), 12.01 (s, 1H); m/z [M$^+$ + 1] 317.0. |
| 71 | 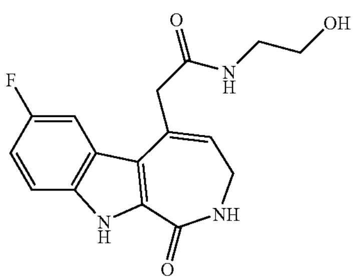 | $^1$H NMR (DMSO-d$_6$) δ 3.10 (q, 2H, J = 6.0 Hz), 3.35 (t, 2H, J = 6.0 Hz), 3.93 (t, 2H, J = 6.4 Hz), 3.53 (s, 2H), 5.89 (t, 1H, J = 6.8 Hz), 7.12 (dt, 1H, J$_1$ = 2.4 Hz, J$_2$ = 8.8 Hz), 7.46 (dd, 1H, J$_1$ = 5.2 Hz, J$_2$ = 9.6 Hz), 7.66 (dd, 1H, J$_1$ = 1.6 Hz, J$_2$ = 10.8 Hz), 7.96 (t, 1H, J = 5.6 Hz), 8.16 (t, 1H, J = 4.8 Hz), 11.98 (s, 1H); m/z [M$^+$ + 1] 318.1. |
| 72 | 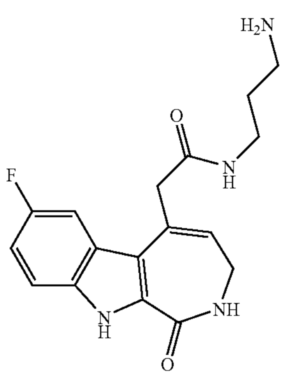 | $^1$H NMR (DMSO-d$_6$) δ 1.49 (quint, 2H, J = 6.8 Hz), 3.08 (q, 2H, J = 5.6 Hz), 3.35 (t, 2H, J = 6.4 Hz), 3.40 (t, 2H, J = 6.0 Hz), 3.51 (s, 2H), 5.88 (t, 1H, J = 6.8 Hz), 7.12 (dt, 1H, J$_1$ = 2.8 Hz, J$_2$ = 8.8 Hz), 7.45 (dd, 1H, J$_1$ = 5.2 Hz, J$_2$ = 8.8 Hz), 7.66 (dd, 1H, J$_1$ = 2.4 Hz, J$_2$ = 11.2 Hz), 7.93 (t, 1H, J = 5.6 Hz), 8.16 (t, 1H, J = 5.2 Hz), 11.98 (s, 1H); m/z [M$^+$ + 1] 332.1. |

TABLE 1-continued

| Compound | Structure | Physical Data |
|---|---|---|
| 73 | 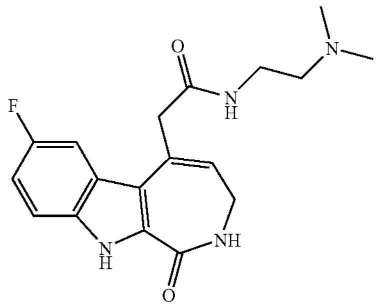 | $^1$H NMR (DMSO-d$_6$) δ 2.54 (s, 6H), 3.06 (t, 2H, J = 6.4 Hz), 3.37 (t, 2H, J = 7.2 Hz), 3.41 (t, 2H, J = 6.4 Hz), 3.58 (s, 2H), 5.91 (t, 1H, J = 7.2 Hz), 7.13 (dt, 1H, J$_1$ = 3.2 Hz, J$_2$ = 8.8 Hz), 7.46 (dd, 1H, J$_1$ = 5.2 Hz, J$_2$ = 9.6 Hz), 7.63 (dd, 1H, J$_1$ = 2.4 Hz, J$_2$ = 10.4 Hz), 8.19 (t, 1H, J = 5.2 Hz), 8.22 (t, 1H, J = 5.6 Hz) 9.34 (bs, 1H), 12.02 (s, 1H); m/z [M$^+$ + 1] 345.1. |
| 74 | 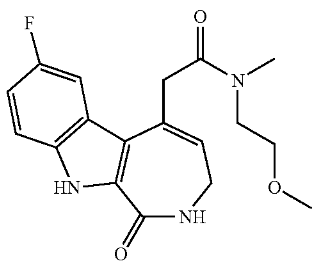 | $^1$H NMR (DMSO-d$_6$) δ 2.81 & 3.01 (s, 3H), 3.20 & 3.26 (s, 3H), 3.33-3.44 (m, 4H), 3.46-3.51 (m, 2H), 3.77 & 3.81(s, 2H), 5.74 & 5.76 (t, 1H, J = 6.4 Hz), 7.11 (d, 1H, J = 9.2 Hz), 7.44-7.52 (m, 2H), 8.15 & 8.16 (t, 1H, J = 5.6 Hz), 11.97 & 11.99 (s, 1H); m/z [M$^+$ + 1] 346.16. |
| 75 | 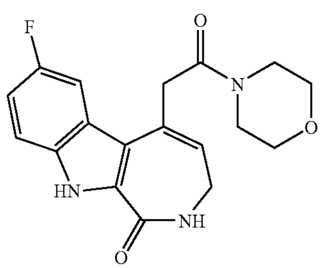 | $^1$H NMR (DMSO-d$_6$) δ 3.38-3.57 (m, 10H), 3.81 (s, 2H), 5.78 (t, 1H, J = 6.8 Hz), 7.12 (dt, 1H, J$_1$ = 2.0 Hz, J$_2$ = 8.8 Hz), 7.46 (dd, 1H, J$_1$ = 4.4 Hz, J$_2$ = 8.8 Hz), 7.56 (dd, 1H, J$_1$ = 2.4 Hz, J$_2$ = 10.8 Hz), 8.17 (t, 1H, J = 5.2 Hz), 12.00 (s, 1H); m/z [M$^+$+ 1] 344.1. |
| 76 | 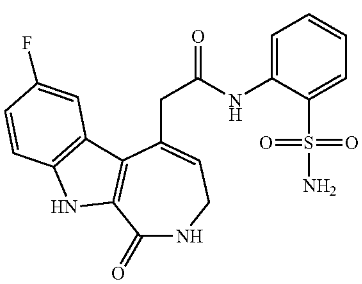 | $^1$H NMR (DMSO-d$_6$) δ 3.48 (t, 2H, J = 6.4 Hz), 3.88 (s, 2H), 6.08 (t, 1H, J = 6.4 Hz), 7.13 (tt, 1H, J$_1$ = 2.0 Hz, J$_2$ = 8.8 Hz), 7.26 (dt, 1H, J$_1$ = 2.4 Hz, J$_2$ = 7.2 Hz), 7.46-7.51 (m, 1H), 7.51-7.57 (m, 1H), 7.57 (s, 2H), 7.63 (dt, 1H, J$_1$ = 2.4 Hz, J$_2$ = 10.8 Hz), 7.82 (dt, 1H, J$_1$ = 2.0 Hz, J$_2$ = 8.0 Hz), 8.08 (dd, 1H, J$_1$ = 1.6 Hz, J$_2$ = 8.0 Hz), 8.19 (t, 1H, J = 6.0 Hz), 9.59 (s, 1H), 12.07 (s, 1H); m/z [M$^+$+ 1] 429.0. |
| 77 | 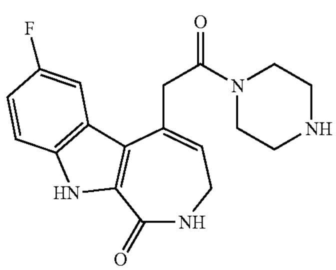 | $^1$H NMR (DMSO-d$_6$) δ 3.00-3.20 (m, 2H), 3.38-3.50 (m, 6H), 3.60-3.70 (m, 2H), 3.88 (s, 2H), 5.78 (t, 1H, J = 6.4 Hz), 7.13 (dt, 1H, J$_1$ = 1.6 Hz, J$_2$ = 8.8 Hz), 7.46 (dd, 1H, J$_1$ = 5.2 Hz, J$_2$ = 9.2 Hz), 7.57 (dd, 1H, J$_1$ = 2.4 Hz, J$_2$ = 10.0 Hz), 8.18 (t, 1H, J = 5.2 Hz), 12.02 (s, 1H); m/z [M$^+$ + 1] 343.1. |

TABLE 1-continued

| Compound | Structure | Physical Data |
|---|---|---|
| 78 | 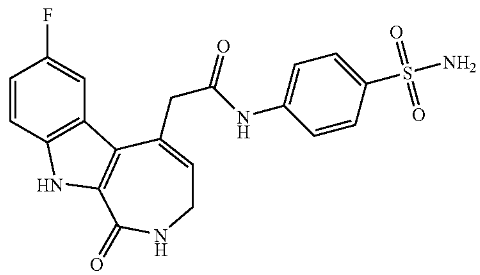 | $^1$H NMR (DMSO-d$_6$) δ 3.43 (t, 2H, J = 6.8 Hz), 3.84 (s, 2H), 5.96 (t, 1H, J = 6.4 Hz), 7.12 (dt, 1H, J$_1$ = 2.8 Hz, J$_2$ = 8.4 Hz), 7.20 (s, 2H), 7.44-7.50 (m, 1H), 7.68-7.76 (m, 5H), 8.18 (t, 1H, J = 5.2 Hz), 10.44 (s, 1H), 12.02 (s, 1H); m/z [M$^+$ + 1] 429.0. |
| 79 | 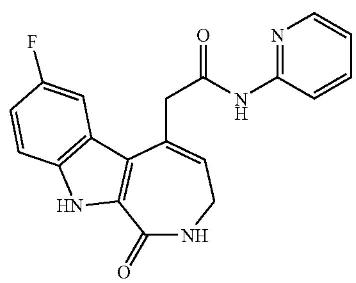 | $^1$H NMR (DMSO-d$_6$) δ 3.42 (t, 2H, J = 6.0 Hz), 3.91 (s, 2H), 5.96 (t, 1H, J = 7.6 Hz), 7.07-7.13 (m, 2H), 7.45 (dt, 1H, J$_1$ = 4.4 Hz, J$_2$ = 8.8 Hz), 7.72-7.78 (m, 2H), 7.94 (d, 1H, J = 8.8 Hz), 8.18 (t, 1H, J = 5.2 Hz), 8.29 (d, 1H, J = 5.2 Hz), 10.70 (s, 1H), 12.01 (s, 1H); m/z [M$^+$+ 1] 351.1. |
| 80 | 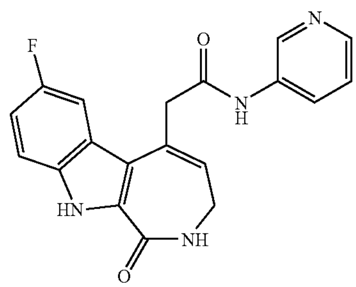 | $^1$H NMR (DMSO-d$_6$) δ 3.44 (t, 2H, J = 6.0 Hz), 3.88 (s, 2H), 5.98 (t, 1H, J = 6.4 Hz), 7.12 (dt, 1H, J$_1$ = 2.4 Hz, J$_2$ = 9.6 Hz), 7.47 (dd, 1H, J$_1$ = 5.2 Hz, J$_2$ = 8.8 Hz), 7.60 (dd, 1H, J$_1$ = 4.4 Hz, J$_2$ = 8.4 Hz), 7.68 (d, 1H, J = 8.8 Hz), 8.16 (d, 1H, J = 9.6 Hz), 8.19 (t, 1H, J = 5.2 Hz), 8.39 (d, 1H, J = 5.2 Hz), 8.91 (s, 1H), 10.64 (s, 1H), 12.04 (s, 1H); m/z [M$^+$ + 1] 351.1. |
| 81 | 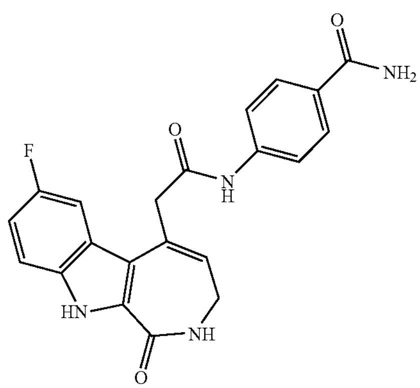 | $^1$H NMR (DMSO-d$_6$) δ 3.43 (t, 2H, J = 6.4 Hz), 3.83 (s, 2H), 5.96 (t, 1H, J = 6.4 Hz), 7.12 (dt, 1H, J$_1$ = 2.0 Hz, J$_2$ = 8.8 Hz), 7.18 (bs, 1H), 7.46 (dd, 1H, J$_1$ = 4.4 Hz, J$_2$ = 8.8 Hz), 7.59 (d, 2H, J = 8.8 Hz), 7.70 (d, 1H, J = 10.8 Hz), 7.80 (d, 2H, J = 8.8 Hz), 8.18 (t, 1H, J = 5.2 Hz), 10.30 (s, 1H), 12.02 (s, 1H); m/z [M$^+$ + 1] 393.1. |
| 82 | 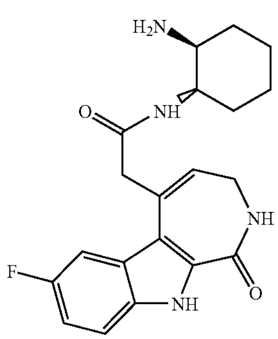 | $^1$H NMR (DMSO-d$_6$) δ 1.13-1.38 (m, 4H), 1.57-1.70 (m, 2H), 1.92-1.98 (m, 1H), 2.80-2.90 (m, 1H), 3.41 (t, 2H, J = 6.4 Hz), 3.50-3.68 (m, 4H), 5.89 (t, 1H, J = 7.2 Hz), 7.12 (dt, 1H, J$_1$ = 2.0 Hz, J$_2$ = 8.8 Hz), 7.46 (dd, 1H, J$_1$ = 4.4 Hz, J$_2$ = 8.8 Hz), 7.66 (dd, 1H, J$_1$ = 2.0 Hz, J$_2$ = 11.2 Hz), 7.79 (bs, 3H), 8.02 (d, 1H, J = 8.8 Hz), 8.18 (t, 1H, J = 5.2 Hz), 11.99 (s, 1H); m/z [M$^+$ + 1] 371.1. |

TABLE 1-continued

| Compound | Structure | Physical Data |
|---|---|---|
| 83 | 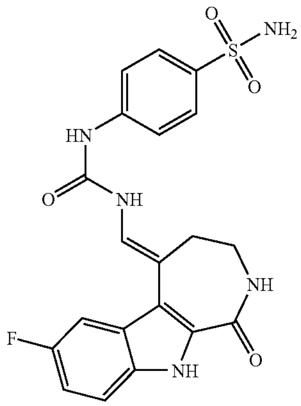 | ¹H NMR (DMSO-d₆) δ 2.72-2.79 (m, 2H), 3.33-3.37 (m, 2H), 7.07-7.19 (m, 2H), 7.22 (s, 2H), 7.42-7.48 (s, 2H), 7.63 (d, 2H, J = 8.8 Hz), 7.73 (d, 2H, J = 8.8 Hz), 8.19 (t, 1H, J = 4.8 Hz), 8.47 (d, 1H, J = 11.2 Hz), 9.23 (s, 1H), 11.66 (s, 1H); m/z [M⁺ + 1] 440.0. |
| 84 | 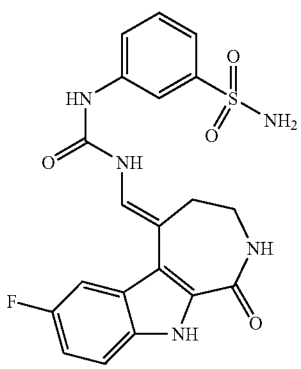 | ¹H NMR (DMSO-d₆) δ 2.72-2.79 (m, 2H), 3.32-3.38 (m, 2H), 7.13 (dt, 1H, J₁ = 2.8 Hz, J₂ = 8.8 Hz), 7.18 (d, 1H, J = 10.0 Hz), 7.35 (s, 2H), 7.42-7.49 (m, 4H), 7.54 (d, 1H, J = 8.4 Hz), 8.10 (s, 1H), 8.18 (t, 1H, J = 5.2 Hz), 8.39 (d, 1H, J = 10.0 Hz), 9.18 (s, 1H), 11.65 (s, 1H); m/z [M⁺ + 1] 444.0. |
| 85 | 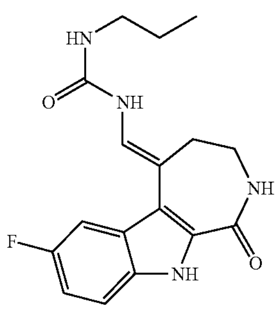 | ¹H NMR (DMSO-d₆) δ 0.88 (t, 3H, J = 6.8 Hz), 1.44 (q, 2H, J = 6.8 Hz), 2.64-2.68 (m, 2H), 3.06 (q, 2H, J = 6.4 Hz), 3.27-3.33 (m, 2H), 6.37 (t, 1H, J = 5.2 Hz), 7.09 (dd, 1H, J₁ = 2.8 Hz, J₂ = 9.6 Hz), 7.13 (d, 1H, J = 10.4 Hz), 7.37-7.43 (m, 2H), 8.06 (d, 1H, J = 11.2 Hz), 8.11 (t, 1H, J = 5.2 Hz), 11.54 (s, 1H); m/z [M⁺ + 1] 331.1. |
| 86 | 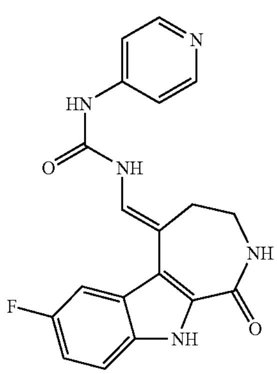 | ¹H NMR (DMSO-d₆) δ 2.75-2.80 (m, 2H), 3.30-3.34 (m, 2H), 7.10-7.17 (m, 2H), 7.44-7.49 (m, 2H), 7.90-7.96 (bs, 2H), 8.22 (t, 1H, J = 5.2 Hz), 8.59-8.68 (bs, 2H), 9.11 (d, 1H, J = 10.4 Hz), 10.62 (s, 1H), 11.74 (s, 1H); m/z [M⁺ + 1] 366.1. |

TABLE 1-continued

| Compound | Structure | Physical Data |
|---|---|---|
| 87 | 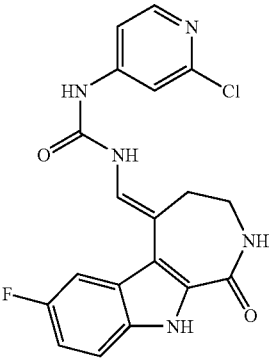 | $^1$H NMR (DMSO-d$_6$) δ 2.73-2.78 (m, 2H), 3.32-3.36 (m, 2H), 7.10-7.16 (m, 2H), 7.31 (dd, 1H, J$_1$ = 1.6 Hz, J$_2$ = 5.2 Hz), 7.42-7.47 (m, 2H), 7.70 (s, 1H), 8.19 (d, 2H, J = 6.0 Hz), 8.65 (d, 1H, J = 10.8 Hz), 9.54 (s, 1H), 11.69 (s, 1H); m/z [M$^+$ + 1] 400.0. |
| 88 | 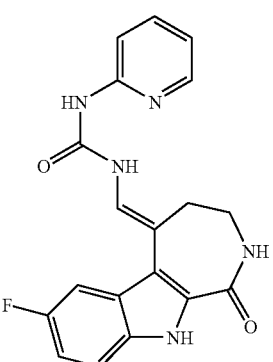 | $^1$H NMR (DMSO-d$_6$) δ 2.78-2.82 (m, 2H), 3.35-3.40 (m, 2H), 7.03 (dd, 1H, J$_1$ = 5.6 Hz, J$_2$ = 7.2 Hz), 7.13 (dt, 1H, J$_1$ = 2.8 Hz, J$_2$ = 9.6 Hz), 7.23 (d, 1H, J = 10.8 Hz), 7.43-7.48 (m, 3H), 7.77 (dt, 1H, J$_1$ = 2.0 Hz, J$_2$ = 7.8 Hz), 8.21 (t, 1H, J = 5.2 Hz), 8.31 (d, 1H, J = 5.2 Hz), 9.73 (s, 1H), 10.39 (bs, 1H), 11.67 (s, 1H); m/z [M$^+$ + 1] 366.1. |
| 89 | 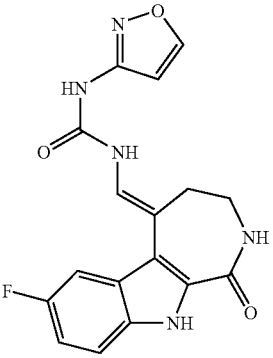 | $^1$H NMR (DMSO-d$_6$) δ 2.70-2.75 (m, 2H), 3.30-3.36 (m, 2H), 6.84 (d, 1H, J = 2.8 Hz), 7.10-7.15 (m, 2H), 7.43-7.46 (m, 2H), 8.19 (t, 1H, J = 5.6 Hz), 8.54 (d, 1H, J = 10.8 Hz), 8.75 (d, 1H, J = 2.0 Hz), 9.74 (s, 1H), 11.68 (s, 1H); m/z [M$^+$ + 1] 356.1. |
| 90 | 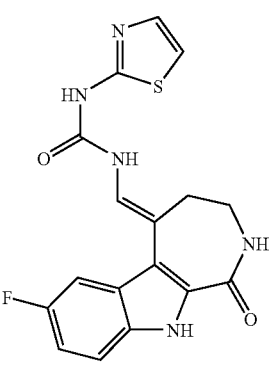 | $^1$H NMR (DMSO-d$_6$) δ 2.73-2.76 (m, 2H), 3.33-3.37 (m, 2H), 7.11-7.16 (m, 3H), 7.38 (d, 1H, J = 3.6 Hz), 7.43-7.48 (m, 2H), 8.19 (t, 1H, J = 5.2 Hz), 8.67 (d, 1H, J = 10.4 Hz), 10.60 (bs, 1H), 11.69 (s, 1H); m/z [M$^+$ + 1] 372.0. |

TABLE 1-continued

| Compound | Structure | Physical Data |
|---|---|---|
| 91 | 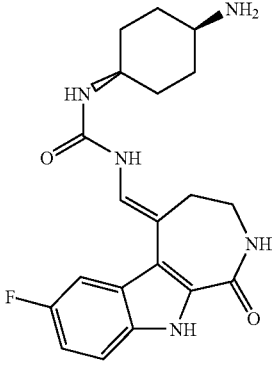 | $^1$H NMR (DMSO-d$_6$) δ 1.18-1.28 (m, 2H), 1.34-1.44 (m, 2H), 1.88-1.98 (m, 4H), 2.52-2.54 (m, 1H), 2.62-2.68 (m, 2H), 2.97-3.04 (m, 1H), 3.28-3.32 (m, 2H), 6.39 (d, 1H, J = 7.2 Hz), 7.07-7.14 (m, 2H), 7.36-7.43 (m, 2H), 7.80 (s, 3H), 8.07 (d, 1H, J = 10.4 Hz), 8.11 (t, 1H, J = 5.2 Hz), 11.54 (s, 1H); m/z [M$^+$ + 1] 386.3. |
| 92 | 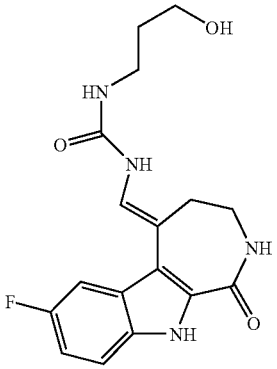 | $^1$H NMR (DMSO-d$_6$) δ 1.58 (quint, 2H, J = 6.4 Hz), 2.63-2.68 (m, 2H), 3.17 (q, 2H, J = 6.4 Hz), 3.28-3.33 (m, 2H), 3.45 (t, 2H, J = 6.4 Hz), 6.37 (t, 1H, J = 8.8 Hz), 7.09 (dd, 1H, J$_1$ = 2.0 Hz, J$_2$ = 8.8 Hz), 7.13 (d, 1H, J = 9.6 Hz), 7.38-7.43 (m, 2H), 8.10 (d, 1H, J = 3.6 Hz), 8.13 (s, 1H), 11.53 (s, 1H; m/z [M$^+$ + 1] 347.1. |
| 93 | 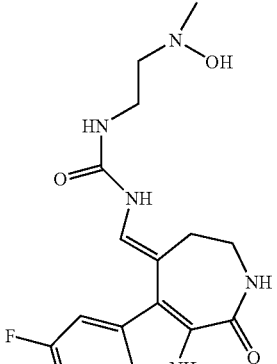 | $^1$H NMR (DMSO-d$_6$) δ 2.67-2.70 (m, 2H), 2.83 (d, 6H, J = 5.2 Hz), 3.18 (q, 2H, J = 5.2 Hz), 3.28-3.33 (m, 2H), 3.47 (q, 2H, J = 5.2 Hz), 6.71 (t, 1H, J = 5.6 Hz), 7.08-7.15 (m, 2H), 7.38-7.44 (m, 2H), 8.15 (t, 1H, J = 5.2 Hz), 8.45 (d, 1H, J = 10.4 Hz), 9.34 (bs, 1H), 11.59 (s, 1H); m/z [M$^+$ + 1] 360.2 |
| 94 | 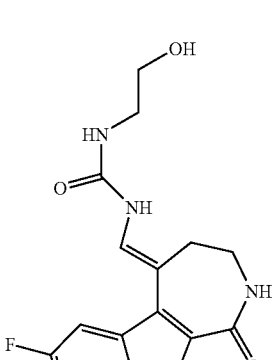 | $^1$H NMR (DMSO-d$_6$) δ 2.64-2.68 (m, 2H), 3.17 (q, 2H, J = 6.0 Hz), 3.28-3.33 (m, 2H), 3.45 (t, 2H, J = 5.4 Hz), 6.49 (t, 1H, J = 5.6 Hz), 7.10 (dt, 1H, J$_1$ = 2.8 Hz, J$_2$ = 8.8 Hz), 7.13 (d, 1H, J = 9.6 Hz), 7.37-7.43 (m, 2H), 8.12 (t, 1H, J = 5.6 Hz), 8.21 (d, 1H, J = 10.8 Hz), 11.54 (s, 1H); m/z [M$^+$ + 1] 333.1. |

TABLE 1-continued

| Compound | Structure | Physical Data |
|---|---|---|
| 95 | 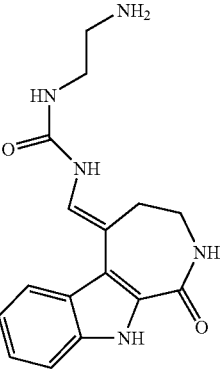 | $^1$H NMR (DMSO-d$_6$) δ 2.66-2.70 (m, 2H), 2.91 (q, 2H, J = 6.0 Hz), 3.28-3.32 (m, 2H), 3.34 (t, 2H, J = 6.0 Hz), 6.65 (t, 1H, J = 5.2 Hz), 7.08-7.15 (m, 2H), 7.39-7.44 (m, 2H), 7.76 (bs, 3H), 8.14 (t, 1H, J = 5.2 Hz), 8.40 (d, 1H, J = 10.8 Hz), 11.59 (s, 1H); m/z [M$^+$ + 1] 332.0. |
| 96 | 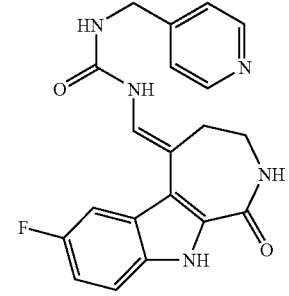 | $^1$H NMR (DMSO-d$_6$) δ 2.71-2.73 (m, 2H), 3.30-3.34 (m, 2H), 4.55 (d, 2H, J = 6.0 Hz), 7.07-7.19 (m, 3H), 7.37-7.44 (m, 2H), 7.77 (d, 2H, J = 6.4 Hz), 8.14 (t, 1H, J = 5.2 Hz), 8.54 (d, 1H, J = 10.0 Hz), 8.77 (d, 2H, J = 5.2 Hz), 11.57 (s, 1H); m/z [M$^+$ + 1] 380.0. |
| 97 | 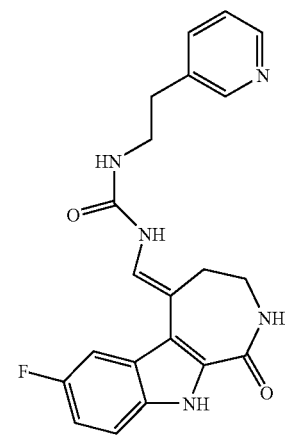 | $^1$H NMR (DMSO-d$_6$) δ 2.62-2.67 (m, 2H), 2.92 (t, 2H, J = 6.4 Hz), 3.27-3.31 (m, 2H), 3.44 (q, 2H, J = 6.4 Hz), 6.49 (t, 1H, J = 5.2 Hz), 7.07-7.13 (m, 2H), 7.38 (dd, 1H, J$_1$ = 2.0 Hz, J$_2$ = 10.0 Hz), 7.41 (dd, 1H, J$_1$ = 4.4 Hz, J$_2$ = 8.8 Hz), 7.80 (dd, 1H, J$_1$ = 5.2 Hz, J$_2$ = 8.8 Hz), 8.12 (t, 1H, J = 4.4 Hz), 8.17 (d, 1H, J = 10.8 Hz), 8.21 (d, 1H, J = 8.0 Hz), 8.68 (d, 1H, J = 5.2 Hz), 8.71 (s, 1H), 11.56 (s, 1H); m/z [M$^+$ + 1] 394.2. |
| 98 | 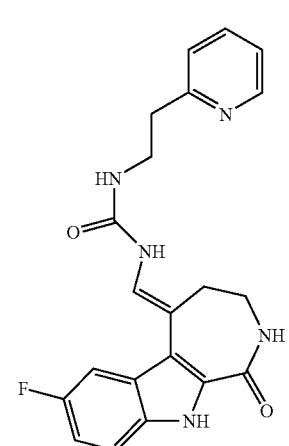 | $^1$H NMR (DMSO-d$_6$) δ 2.60-2.66 (m, 2H), 3.10 (t, 2H, J = 6.4 Hz), 3.26-3.31 (m, 2H), 3.55 (q, 2H), J = 6.4 Hz), 6.55 (t, 1H, J = 5.2 Hz), 7.06 (d, 1H, J = 10.8 Hz), 7.10 (dt, 1H, J$_1$ = 1.6 Hz, J$_2$ = 8.8 Hz), 7.37 (dd, 1H, J$_1$ = 2.4 Hz, J$_2$ = 10.8 Hz), 7.41 (dd, 1H, J$_1$ = 4.8 Hz, J$_2$ = 8.8 Hz), 7.70 (t, 1H, J = 6.8 Hz), 7.75 (d, 1H, J = 7.6 Hz), 8.12 (t, 1H, J = 5.2 Hz), 8.19 (d, 1H, J = 10.8 Hz), 8.27 (t, 1H, J = 7.6 Hz), 8.75 (d, 1H, J = 5.2 Hz), 11.56 (s, 1H); m/z [M$^+$ + 1] 394.2. |

TABLE 1-continued

| Compound | Structure | Physical Data |
|---|---|---|
| 99 | 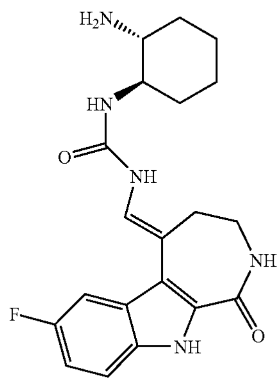 | $^1$H NMR (DMSO-d$_6$) δ 1.20-1.40 (m, 4H), 1.66-1.72 (m, 2H), 1.82-1.88 (m, 1H), 1.92-2.00 (m, 1H), 2.65-2.70 (m, 2H), 2.84-2.92 (m, 1H), 3.29-3.33 (m, 2H), 3.52-3.58 (m, 1H), 6.63 (d, 1H, J = 8.0 Hz), 7.10 (dt, 1H, J$_1$ = 2.0 Hz, J$_2$ = 9.6 Hz), 7.15 (d, 1H, J = 10.8 Hz), 7.40-7.45 (m, 2H), 7.81 (bs, 3H), 8.14 (t, 1H, J = 4.8 Hz), 8.34 (d, 1H, J = 11.2 Hz), 11.58 (s, 1H); m/z [M$^+$ + 1] 386.2. |
| 100 | 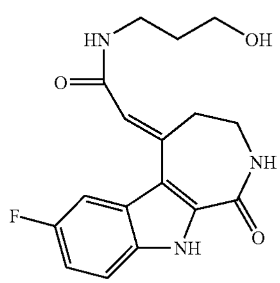 | $^1$H NMR (DMSO-d$_6$) δ 1.61 (quint, 2H, J = 6.4 Hz), 3.18 (q, 2H, J = 6.4 Hz), 3.23-3.28 (m, 2H), 3.42-3.48 (m, 2H), 3.45 (t, 2H, J = 6.4 Hz), 6.35 (s, 1H), 7.16 (dt, 1H, J$_1$ = 2.0 Hz, J$_2$ = 8.8 Hz), 7.48 (dd, 1H, J$_1$ = 4.2 Hz, J$_2$ = 8.8 Hz), 7.76 (dd, 1H, J$_1$ = 2.0 Hz, J$_2$ = 10.0 Hz), 8.16 (t, 1H, J = 4.8 Hz), 8.36 (t, 1H, J = 5.2 Hz), 12.03 (s, 1H); m/z [M$^+$ + 1] 332.1. |
| 101 | 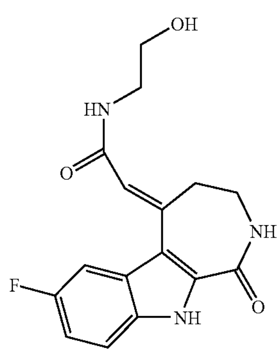 | $^1$H NMR (DMSO-d$_6$) δ 3.21 (q, 2H, J = 6.0 Hz), 3.24-3.28 (m, 2H), 3.43-3.45 (m, 2H), 3.46 (t, 2H, J = 6.0 Hz), 6.39 (s, 1H), 7.16 (dt, 1H, J$_1$ = 2.0 Hz, J$_2$ = 9.6 Hz), 7.49 (dd, 1H, J$_1$ = 5.2 Hz, J$_2$ = 8.8 Hz), 7.79 (dd, 1H, J$_1$ = 2.0 Hz, J$_2$ = 10.8 Hz), 8.25 (t, 1H, J = 5.6 Hz), 8.36 (t, 1H, J = 4.8 Hz), 12.02 (s, 1H); m/z [M$^+$ + 1] 318.1. |
| 102 | 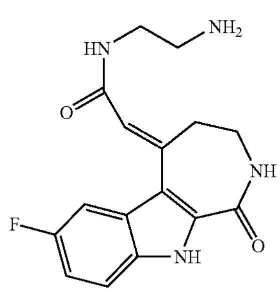 | $^1$H NMR (DMSO-d$_6$) δ 2.88-2.96 (m, 2H), 3.24-3.29 (m, 2H), 3.37 (q, 2H, J = 6.0 Hz), 3.43-3.47 (m, 2H), 6.34 (s, 1H), 7.17 (dt, 1H, J$_1$ = 2.0 Hz, J$_2$ = 9.2 Hz), 7.50 (dd, 1H, J$_1$ = 4.4 Hz, J$_2$ = 10.0 Hz), 7.75 (dd, 1H, J$_1$ = 2.0 Hz, J$_2$ = 10.0 Hz), 7.82 (bs, 3H), 8.36 (t, 1H, J = 5.6 Hz), 8.39 (t, 1H, J = 6.0 Hz), 12.09 (s, 1H); m/z [M$^+$ + 1] 317.1. |

TABLE 1-continued

| Compound | Structure | Physical Data |
|---|---|---|
| 103 | 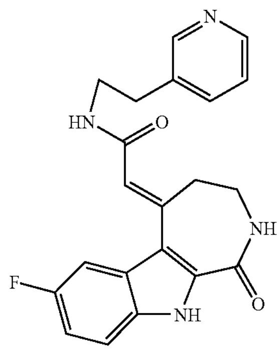 | $^1$H NMR (DMSO-d$_6$) δ 2.93 (t, 2H, J = 6.0 Hz), 3.22-3.26 (m, 2H), 3.37-3.41 (m, 2H), 3.46 (q, 2H, J = 6.0 Hz), 6.30 (s, 1H), 7.16 (dt, 1H, J$_1$ = 2.0 Hz, J$_2$ = 8.8 Hz), 7.49 (dd, 1H, J$_1$ = 4.4 Hz, J$_2$ = 8.8 Hz), 7.70 (dd, 1H, J$_1$ = 2.0 Hz, J$_2$ = 10.8 Hz), 7.78 (dd, 1H, J$_1$ = 5.6 Hz, J$_2$ = 8.0 Hz), 8.21 (d, 1H, J = 8.4 Hz), 8.29 (t, 1H, J = 5.2 Hz), 8.37 (t, 1H, J = 5.2 Hz), 8.67 (d, 1H, J = 4.4 Hz), 8.72 (s, 1H), 12.06 (s, 1H); m/z [M$^+$ + 1] 379.1. |
| 104 | 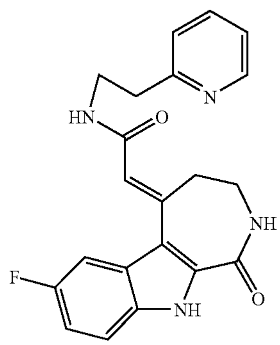 | $^1$H NMR (DMSO-d$_6$) δ 3.09 (t, 2H, J = 7.2 Hz), 3.21-3.26 (m, 2H), 3.36-3.39 (m, 2H), 3.55 (q, 2H, J = 7.2 Hz), 6.28 (s, 1H), 7.16 (dt, 1H, J$_1$ = 2.4 Hz, J$_2$ = 8.8 Hz), 7.49 (dd, 1H, J$_1$ = 4.8 Hz, J$_2$ = 10.2 Hz), 7.65 (t, 1H, J = 6.4 Hz), 7.69 (s, 1H), 7.72 (d, 1H), 8.21 (t, 1H, J = 7.2 Hz), 8.32 (t, 1H, J = 6.0 Hz), 8.37 (t, 1H, J = 4.4 Hz), 8.72 (d, 1H, J = 4.0 Hz), 12.05 (s, 1H); m/z [M$^+$ + 1] 379.1. |
| 105 | 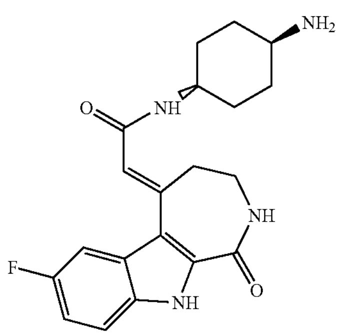 | $^1$H NMR (DMSO-d$_6$) δ 1.20-1.32 (m, 2H), 1.36-1.43 (m, 2H), 1.88-2.00 (m, 4H), 2.50-2.53 (m, 1H), 2.96-3.08 (m, 1H), 3.21-3.28 (m, 2H), 346-3.48 (m, 2H), 6.31 (s, 1H), 7.16 (dt, 1H, J$_1$ = 2.4 Hz, J$_2$ = 9.2 Hz), 7.48 (dd, 1H, J$_1$ = 4.4 Hz, J$_2$ = 9.2 Hz), 7.73 (dd, 1H, J$_1$ = 2.8 Hz, J$_2$ = 10.0 Hz), 7.82 (bs, 3H), 8.09 (d, 1H, J = 8.0 Hz), 8.39 (t, 1H, J = 5.2 Hz), 12.04 (s, 1H); m/z [M$^+$ + 1] 371.3. |
| 106 | 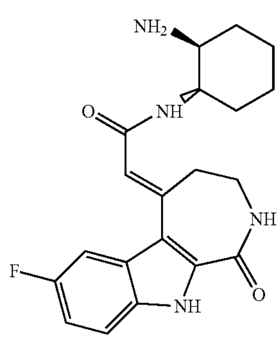 | $^1$H NMR (DMSO-d$_6$) δ 1.20-1.44 (m, 4H), 1.68-1.76 (m, 2H), 1.81-1.88 (m, 1H), 1.96-2.04 (m, 1H), 2.80-2.92 (m, 1H), 3.24-3.30 (m, 2H), 3.44-3.48 (m, 2H), 3.72-3.80 (m, 1H), 6.35 (s, 1H), 7.18 (dt, 1H, J$_1$ = 2.4 Hz, J$_2$ = 8.8 Hz), 7.50 (dd, 1H, J$_1$ = 5.2 Hz, J$_2$ = 8.8 Hz), 7.79 (dd, 1H, J$_1$ = 2.0 Hz, J$_2$ = 10.0 Hz), 7.82 (bs, 3H), 8.17 (d, 1H, J = 8.8 Hz), 8.39 (t, 1H, J = 4.8 Hz), 12.09 (s, 1H); m/z [M$^+$ + 1] 371.2. |

TABLE 1-continued

| Compound | Structure | Physical Data |
|---|---|---|
| 107 | 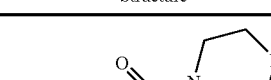 | $^1$H NMR (DMSO-$d_6$) δ 3.05-3.08 (m, 2H), 3.14 (t, 4H, J = 4.4 Hz), 3.26-3.31 (m, 2H), 3.72 (t, 4H, J = 4.4 Hz), 6.55 (s, 1H), 7.16 (dt, 1H, $J_1$ = 2.0 Hz, $J_2$ = 10.8 Hz), 7.50 (dd, 1H, $J_1$ = 5.2 Hz, $J_2$ = 8.8 Hz), 7.64 (dd, 1H, $J_1$ = 2.8 Hz, $J_2$ = 10.8 Hz), 8.36 (t, 1H, J = 5.2 Hz), 8.83 (bs, 2H), 12.04 (s, 1H); m/z [M$^+$ + 1] 343.1. |

Example 10

Compounds of Formula I Exhibit Biological Activity

Compounds of Formula I exhibit inhibitory activity against CDK1, CDK2, CDK4, CDK5, GSK3β, Bcr-abl, Flt-3, c-Kit, PDGFRβ, Mek1, CK1, c-Abl, KDR, IGF-1R, Flt-1, Tek, c-src, FGFR-1 and c-Met kinases. The specific activity of compounds of Formula I can be determined to inhibit the above kinases using biological assays known to those of ordinary skill in the art, for example the CDK5 and GSK3β assays described below:

CDK5/p25 Assay

Solutions of test compounds in various concentrations (33 μM to 0.6 nM) were prepared in assay buffer (50 mM MOPS, pH7.2, 5 mM MgCl$_2$). Recombinant CDK5 (in 5 μl of assay buffer) is added to the wells of a 384 well ProxiPlate™. A solution (10 μl) containing 1.5 μM ATP, 1.5 μM of biotinylated CDK5 substrate peptide (LCB-AGAKKAVKKTP-KKAKKP), 0.01 mCi/ml of [γ-$^{33}$P]-ATP in assay buffer is added to the wells. The reaction is incubated for 60 minutes at room temperature before the addition of stop solution (10 μl of 50 mM ATP, 5 mM of EDTA, 0.1% Triton X-100 and 5 mg/ml streptavadin-PVT beads in PBS). The plates are centrifuged for 2 minutes at 2000 rpm and the scintillation signal is quantified using the TopCount (Packard). IC$_{50}$s are calculated using XLfit software.

GSK35 Assay

Solutions of test compounds in various concentrations (33 μM to 0.6 nM) were prepared in assay buffer (50 mM MOPS, pH7.2, 5 mM MgCl$_2$). Recombinant GSK3β (in 5 μl of assay buffer) is added to the wells of a 384 well ProxiPlate™. A solution (10 μl) containing 1.5 μM ATP, 1.5 μM of biotinylated CDK5 substrate peptide (biotin-YR-RAAVPPSPSLSRHSSPHQ(pS)EDEEE) for 60 minutes at room temperature before the addition of stop solution (10 μl of 50 mM ATP, 5 mM of EDTA, 0.1% Triton X-100 and 5 mg/ml streptavadin-PVT beads in PBS). The plates are centrifuged for 2 minutes at 2000 rpm and the scintillation signal is quantified using the TopCount (Packard). IC$_{50}$s are calculated using XLfit software.

TABLE 2

Percentage Inhibition of Various Kinases at 10 μM of Compound

| | Compound 12 | Compound 31 | Compound 33 |
|---|---|---|---|
| c-Abl | — | — | — |
| KDR | 70 | — | — |
| Flt-3 | — | — | — |
| IGF-1R | — | — | — |
| PDGFR-β | — | — | 97 |
| c-Kit | 86 | — | — |
| Flt-1 | — | — | — |
| Tek | — | — | 70 |
| c-src | 89 | — | 78 |
| CDK1 | 99 | 95 | 97 |

TABLE 2-continued

Percentage Inhibition of Various Kinases at 10 μM of Compound

| FGFR-1 | 89 | — | — |
|---|---|---|---|
| c-Met | 74 | — | — |

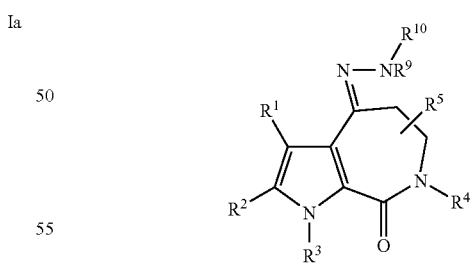

| | | Compound 24 | Compound 37 |
|---|---|---|---|
| | c-Abl | 91 | 86 |
| | KDR | — | — |
| | Flt-3 | 72 | 75 |
| | IGF-1R | 82 | 76 |
| | PDGFR-β | — | — |
| | c-Kit | 79 | — |
| | Flt-1 | 85 | 79 |
| | Tek | 73 | 81 |
| | c-src | 92 | 90 |
| | CDK1 | 88 | 98 |
| | FGFR-1 | — | — |
| | c-Met | — | — |

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

We claim:

1. A compound of Formula Ia:

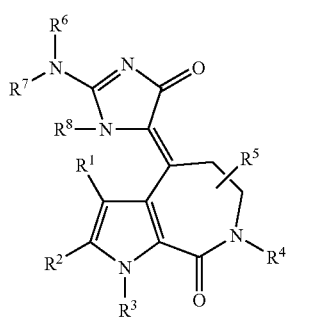

in which:
R$^1$ and R$^2$ are independently selected from halo;
R$^3$, R$^4$, R$^5$, R$^6$ and R$^8$ are independently selected from hydrogen and C$_{1-6}$alkyl; and
R$^7$ is selected from C$_{1-6}$alkyl and —C(O)R$^{11}$; wherein R$^{11}$ is hydrogen or C$_{1-6}$alkyl.

2. The compound of claim 1 in which R$^1$ and R$^2$ are independently selected from halo; R$^3$, R$^4$, R$^6$ and R$^8$ are hydrogen; R$_5$ is selected from hydrogen and methyl; and R$^7$ is selected from ethyl and —C(O)CH$_3$.

3. The compound of claim 2 selected from the group consisting of: N-[5-(2,3-dibromo-8-oxo-5,6,7,8-tetrahydro-1H-pyrrolo[2,3-c]azepin-4-ylidene)-4-oxo-4,5-dihydro-1H-imidazol-2-yl]-acetamide; and 2,3-dibromo-4-(2-ethylamino-5-oxo-3,5-dihydro-imidazol-4-ylidene)-4,5,6,7-tetrahydro-1H-pyrrolo[2,3-c]azepin-8-one.

4. A compound of Formula Ib:

in which R$^1$ and R$^2$ are independently selected from halo and phenyl; R$^3$, R$^4$ and R$^5$ are independently selected from hydrogen and C$_{1-6}$alkyl; R$^9$ is hydrogen; and R$^{10}$ is selected from C$_{1-6}$alkyl, C$_{6-10}$aryl-C$_{0-4}$alkyl, pyridinyl-C$_{0-4}$alkyl, pyrimidinyl, quinolinyl, isoxazolyl and thiazolyl; wherein any aryl or heteroaryl is optionally substituted by 1 to 3 substituents selected from halo, nitro, —C(O)OH, —S(O)$_2$NH$_2$, C$_{1-6}$alkoxy and halo-substituted-C$_{1-6}$alkyl.

5. The compound of claim 4 in which $R^1$ and $R^2$ are independently selected from halo and phenyl; $R^3$ and $R^4$ are hydrogen and $R^5$ is methyl; $R^9$ is hydrogen; $R^{10}$ is selected from $C_{6-10}$aryl-$C_{0-4}$alkyl, pyridinyl-$C_{0-4}$alkyl, pyrimidinyl, quinolinyl, isoxazolyl and thiazolyl; wherein any aryl or heteroaryl is optionally substituted by halo, nitro, —C(O)OH and halo-substituted-$C_{1-6}$alkyl.

6. The compound of claim 5 selected from the group consisting of: 2-[N'-(2,3-dibromo-8-oxo-5,6,7,8-tetrahydro-1H-pyrrolo[2,3-c]azepin-4-ylidene)-hydrazino]-benzoic acid; 4-[N'-(2,3-dibromo-8-oxo-5,6,7,8-tetrahydro-1H-pyrrolo[2,3-c]azepin-4-ylidene)-hydrazino]-benzoic acid; 2,3-dibromo-4-(pyridin-2-yl-hydrazono)-4,5,6,7-tetrahydro-1H-pyrrolo[2,3-c]azepin-8-one; 2,3-dibromo-4-[(4-nitro-phenyl)-hydrazono]-4,5,6,7-tetrahydro-1H-pyrrolo[2,3-c]azepin-8-one; 4-[N'-(2,3-dibromo-8-oxo-5,6,7,8-tetrahydro-1H-pyrrolo[2,3-c]azepin-4-ylidene)-hydrazino]-benzenesulfonamide; 2,3-dibromo-4-[(7-chloro-quinolin-4-yl)-hydrazono]-4,5,6,7-tetrahydro-1H-pyrrolo[2,3-c]azepin-8-one; 2,3-dibromo-4-[(5-trifluoromethyl-pyrimidin-2-yl)-hydrazono]-4,5,6,7-tetrahydro-1H-pyrrolo[2,3-c]azepin-8-one; 2,3-dibromo-4-(pyridin-3-yl-hydrazono)-4,5,6,7-tetrahydro-1H-pyrrolo[2,3-c]azepin-8-one; 2,3-dibromo-4-(pyridin-4-yl-hydrazono)-4,5,6,7-tetrahydro-1H-pyrrolo[2,3-c]azepin-8-one; 2-phenyl-4-(pyridin-2-yl-hydrazono)-4,5,6,7-tetrahydro-1H-pyrrolo[2,3-c]azepin-8-one; 6-methyl-4-(pyridin-2-yl-hydrazono)-4,5,6,7-tetrahydro-1H-pyrrolo[2,3-c]azepin-8-one; and 2,3-dichloro-4-(pyridin-2-yl-hydrazono)-4,5,6,7-tetrahydro-1H-pyrrolo[2,3-c]azepin-8-one.

7. A compound selected from the group consisting of: 4-[N'-(7-chloro-1-oxo-1,3,4,10-tetrahydro-2H-azepino[3,4-b]indol-5-ylidene)-hydrazino]-benzenesulfonamide; 7-bromo-3-methyl-5-(pyridin-2-yl-hydrazono)-3,4,5,10-tetrahydro-2H-azepino[3,4-b]indol-1-one; 4-[N'-(7-fluoro-1-oxo-1,3,4,10-tetrahydro-2H-azepino[3,4-b]indol-5-ylidene)-hydrazino]-benzenesulfonamide; 6-[N'-(7-chloro-1-oxo-1,3,4,10-tetrahydro-2H-azepino[3,4-b]indol-5-ylidene)-hydrazino]-pyridine-3-sulfonic acid amide; 6-[N'-(7-fluoro-1-oxo-1,3,4,10-tetrahydro-2H-azepino[3,4-b]indol-5-ylidene)-hydrazino]-pyridine-3-sulfonic acid amide; 7-fluoro-5-[(5-trifluoromethyl-pyridin-2-yl)-hydrazono]-3,4,5,10-tetrahydro-2H-azepino[3,4-b]indol-1-one; and 7-chloro-5-[(5-trifluoromethyl-pyridin-2-yl)-hydrazono]-3,4,5,10-tetrahydro-2H-azepino[3,4-b]indol-1-one.

8. A compound selected from the group consisting of: 2,3-dibromo-4-(2-ethylamino-3H-imidazol-4-yl)-4,5,6,7-tetrahydro-1H-pyrrolo[2,3-c]azepin-8-one; 5-(2-amino-3H-imidazol-4-yl)-7-bromo-3,4,5,10-tetrahydro-2H-azepino[3,4-b]indol-1-one; 5-(2-amino-3H-imidazol-4-yl)-7-chloro-3,4,5,10-tetrahydro-2H-azepino[3,4-b]indol-1-one; and 5-(2-amino-3H-imidazol-4-yl)-9-nitro-3,4,5,10-tetrahydro-2H-azepino[3,4-b]indol-1-one.

9. A pharmaceutical composition comprising a therapeutically effective amount of a compound of claims 1, 4 or 8 in combination with a pharmaceutically acceptable excipient.

10. A compound selected from 4-(2-amino-5-oxo-3,5-dihydro-imidazol-4-ylidene)-2,3-dibromo-6-methyl-4,5,6,7-tetrahydro-1H-pyrrolo[2,3-c]azepin-8-one and the pharmaceutically acceptable salts thereof.

* * * * *